(12) United States Patent
Qiu et al.

(10) Patent No.: US 12,331,290 B2
(45) Date of Patent: Jun. 17, 2025

(54) RECOMBINANT NUCLEIC ACID MOLECULE AND APPLICATION THEREOF IN PREPARATION OF CIRCULAR RNA

(71) Applicant: Purecodon (Hong Kong) Biopharma Ltd., Hong Kong (CN)

(72) Inventors: Zonghao Qiu, Suzhou (CN); Qiangbo Hou, Suzhou (CN); Yang Zhao, Suzhou (CN); Chijian Zuo, Suzhou (CN); Zhenhua Sun, Suzhou (CN)

(73) Assignee: Purecodon (Hong Kong) Biopharma Ltd., Hong Kong (HK)

( * ) Notice: Subject to any disclaimer, the term of this patent is extended or adjusted under 35 U.S.C. 154(b) by 0 days.

(21) Appl. No.: 17/871,420

(22) Filed: Jul. 22, 2022

(65) Prior Publication Data

US 2023/0279389 A1 Sep. 7, 2023

(30) Foreign Application Priority Data

Mar. 2, 2022 (CN) .......................... 202210200112.6

(51) Int. Cl.
| | | |
|---|---|---|
| *C12N 15/11* | (2006.01) | |
| *A61K 48/00* | (2006.01) | |
| *G16B 30/10* | (2019.01) | |

(52) U.S. Cl.
CPC .......... *C12N 15/11* (2013.01); *A61K 48/0058* (2013.01); *G16B 30/10* (2019.02); *C12N 2310/532* (2013.01)

(58) Field of Classification Search
CPC .............. C12N 15/11; C12N 2310/532; A61K 48/0058; G16B 30/10
See application file for complete search history.

(56) References Cited

U.S. PATENT DOCUMENTS

| | | | |
|---|---|---|---|
| 5,773,244 A | 6/1998 | Ares et al. | |
| 2020/0080106 A1* | 3/2020 | Anderson | ............... C12N 15/79 |
| 2021/0371494 A1* | 12/2021 | Wesselhoeft | ....... C07K 14/7051 |
| 2023/0279407 A1 | 9/2023 | Hou et al. | |

FOREIGN PATENT DOCUMENTS

| | | | |
|---|---|---|---|
| CN | 105985978 A | 10/2016 | |
| CN | 111378686 | 7/2020 | |
| CN | 111836825 A | 10/2020 | |
| CN | 112266418 A | 1/2021 | |
| CN | 112399860 | 2/2021 | |
| CN | 112481289 A | 3/2021 | |
| CN | 114438127 | 5/2022 | |
| CN | 114574473 A | 6/2022 | |
| CN | 114574483 A | 6/2022 | |
| WO | WO2010084371 | 7/2010 | |
| WO | WO 2016011222 A2 | 1/2016 | |
| WO | WO2017222911 | * 12/2017 | ........... C07K 14/435 |
| WO | WO 2018/237372 | 12/2018 | |
| WO | WO 2019236673 A1 | 12/2019 | |
| WO | WO2021189059 | 9/2021 | |
| WO | WO 2021189059 A3 | 9/2021 | |
| WO | WO 2022006399 A1 | 1/2022 | |

OTHER PUBLICATIONS

Rausch et al. (Nucleic Acids Research, Jan. 6, 2021, vol. 49, No. 6 e35, 18 pages).*
Mauro et. al "A Critical Analysis of Codon Optimization in Human Therapeutics", Trends in Molecular Medicine, vol. 20, Issue 11, pp. 604-613, published Nov. 2014. (Year: 2014).*
Burke et al., "Structural conventions for group I introns," Nucleic acids research, Sep. 25, 1987, 15(18):7217-7221.
Chen et al., "Initiation of protein synthesis by the eukaryotic translational apparatus on circular RNAs," Science, Apr. 21, 1995, 268(5209):415-417.
Djebali et al., "Landscape of transcription in human cells," Nature, Sep. 2012, 489(7414):101-108.
Gaglione et al., "Current Methods in Synthesis of Cyclic Oligonucleotides and Analogues," Current Organic Chemistry, Jun. 1, 2012, 16(11):1371-1389.
Guttman et al., "Ab initio reconstruction of cell type-specific transcriptomes in mouse reveals the conserved multi-exonic structure of lincRNAs," Nature biotechnology, May 2010, 28(5):503-510.
Jeck et al., "Detecting and characterizing circular RNAs," Nature biotechnology, May 2014, 32(5):453-461.
Kantoff et al., "Correction of adenosine deaminase deficiency in cultured human T and B cells by retrovirus-mediated gene transfer," Proceedings of the National Academy of Sciences, Sep. 1986, 83(17):6563-6567.

(Continued)

*Primary Examiner* — Nancy J Leith
*Assistant Examiner* — Jessica D Parisi
(74) *Attorney, Agent, or Firm* — Fish & Richardson P.C.

(57) ABSTRACT

The present disclosure relates to a recombinant nucleic acid molecule and an application thereof in preparation of a circular RNA, and in particular, to a recombinant nucleic acid molecule for preparing a circular RNA, a recombinant expression vector, a circular RNA, a composition, a method for preparing a circular RNA, a method for expressing a target polypeptide in a cell, a method for screening a target coding region sequence, a system for screening a target coding region sequence, and a method for screening a ribozyme recognition site sequence. The recombinant nucleic acid molecule provided by the present disclosure provides a Clean PIE system with a novel structure for preparing a circRNA in vitro, which can avoid introducing additional exon sequences into the circular RNA, improve the sequence accuracy of circular RNA molecules, reduce changes in a secondary structure of the circular RNA, and further reduce the immunogenicity of the circular RNA, and has a good application prospects in the fields of nucleic acid vaccines, expression of therapeutic proteins, gene therapy, and the like.

14 Claims, 36 Drawing Sheets

Specification includes a Sequence Listing.

(56) References Cited

OTHER PUBLICATIONS

Kelly et al., "Exon skipping is correlated with exon circularization," Journal of molecular biology, Jul. 31, 2015, 427(15):2414-2417.

Kohn et al., "Establishment and characterization of adenosine deaminase-deficient human T cell lines," The Journal of Immunology, Jun. 1, 1989, 142 (11): 3971-3977, Abstract only.

Leppek et al., "An optimized streptavidin-binding RNA aptamer for purification of ribonucleoprotein complexes identifies novel ARE-binding proteins," Nucleic acids research, Jan. 1, 2014, 42(2):e13, 15 pages.

Liu et al., "RNA circles with minimized immunogenicity as potent PKR inhibitors," Molecular Cell, Jan. 20, 2022, 82(2): 22 pages.

Mortazavi et al., "Mapping and quantifying mammalian transcriptomes by RNA-Seq," Nature methods, Jul. 2008, 5(7):621-628.

Obi et al., "The design and synthesis of circular RNAs," Methods, Dec. 1, 2021, 196: 19 pages.

Wang et al., "Alternative isoform regulation in human tissue transcriptomes," Nature, Nov. 2008, 456(7221):470-476.

Wang et al., "Efficient backsplicing produces translatable circular mRNAs," Rna, Feb. 1, 2015, 21(2): 8 pages.

Wilusz et al., "Long noncoding RNAs: functional surprises from the RNA world," Genes & development, Jul. 1, 2009, 23(13):1494-1504.

Wilusz, "A 360 view of circular RNAs: From biogenesis to functions," Wiley Interdisciplinary Reviews: RNA, Jul. 2018, 9(4):e1478, 17 pages.

Chen et al., "Sensing self and foreign circular RNAs by intron identity, " Molecular Cell, Jul. 20, 2017, 67(2):228-38.

Wesselhoeft et al., "Engineering circular RNA for potent and stable translation in eukaryotic cells," Nature Communications, Jul. 6, 2018, 9(1):2629.

Chen et al., "Circular RNA: Biosynthesis in vitro," Frontiers in Bioengineering and Biotechnology, Nov. 30, 2021, 9:787881, 11 pages.

Li, "CircIRAK3 sponges miR-3607 to facilitate breast cancer metastasis," Master's thesis of Nanjing Medical University, Dec. 2015, 86 pages (with English abstract).

Li, "The protective role and mechanisms of circRNAs in BPA induced spermatocyte toxicity," Huazhong University of Science & Technology, May 2019, 221 pages (with English abstract).

Qiu et al., "Clean-PIE: a novel strategy for efficiently constructing precise circRNA with thoroughly minimized immunogenicity to direct potent and durable protein expression," bioRxiv, Jun. 2022, 30 pages.

Chen et al., "Study of circular RNA translation using reporter systems in living cells," Methods, Dec. 2021, 196:113-20.

Costello et al., "Reinventing the wheel: synthetic circular RNAs for mammalian cell engineering," Trends in Biotechnology, Feb. 2020, 38(2):217-30.

EP Extended European Search Report in European Appln. No. 22186592.6, mailed on Jul. 13, 2023, 8 pages.

Liu et al., "RNA circles with minimized immunogenicity as potent PKR inhibitors," Molecular Cell, Jan. 2022, 82(2):420-34.

Petkovic et al., "RNA circularization strategies in vivo and in vitro," Nucleic Acids Research, Feb. 2015, 43(4):2454-65.

Prats et al., "Circular RNA, the key for translation," International Journal of Molecular Sciences, Nov. 2020, 21(22):8591.

Qiu et al., Clean-PIE: a novel strategy for efficiently constructing precise circRNA with thoroughly minimized immunogenicity to direct potent and durable protein expression, bioRxiv, Jun. 2022.

Qu et al., "Circular RNA vaccines against SARS-CoV-2 and emerging variants," Cell, May 2022, 185(10):1728-44.

\* cited by examiner

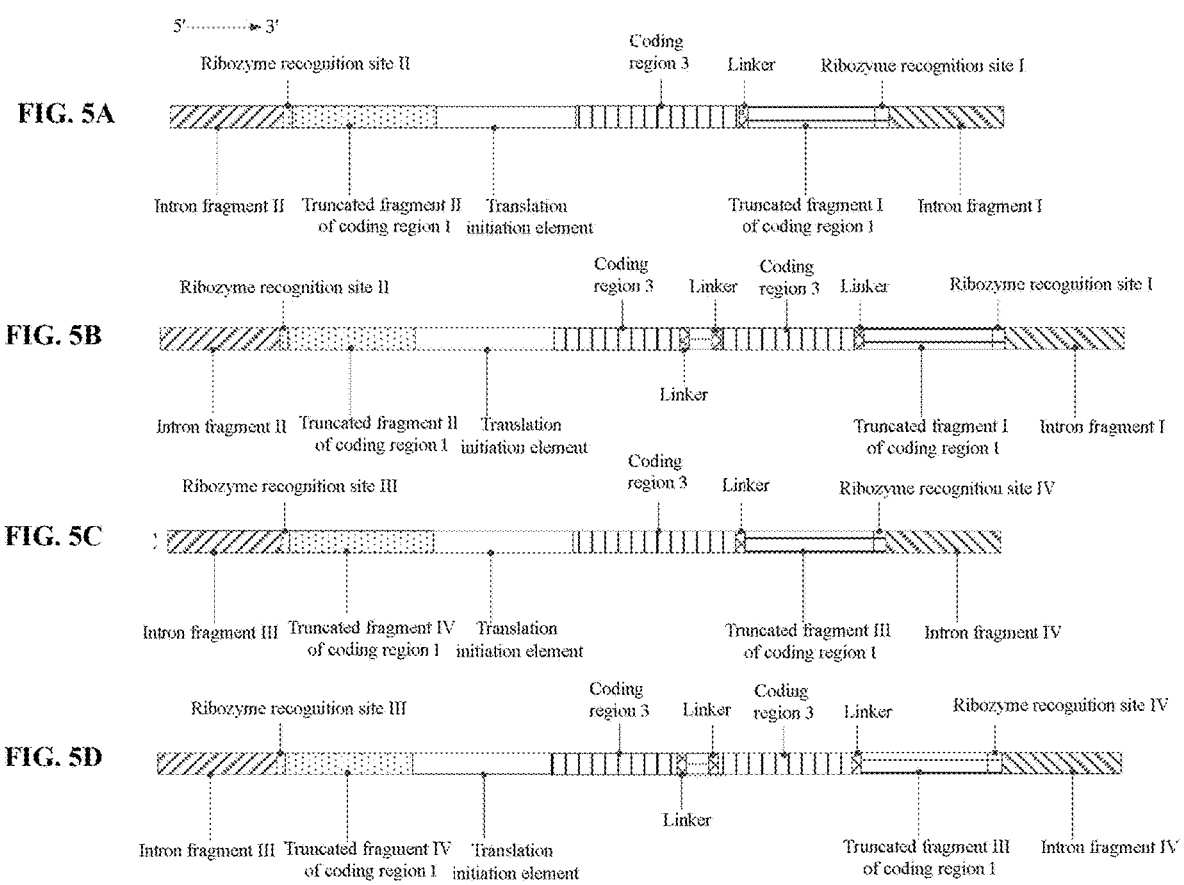

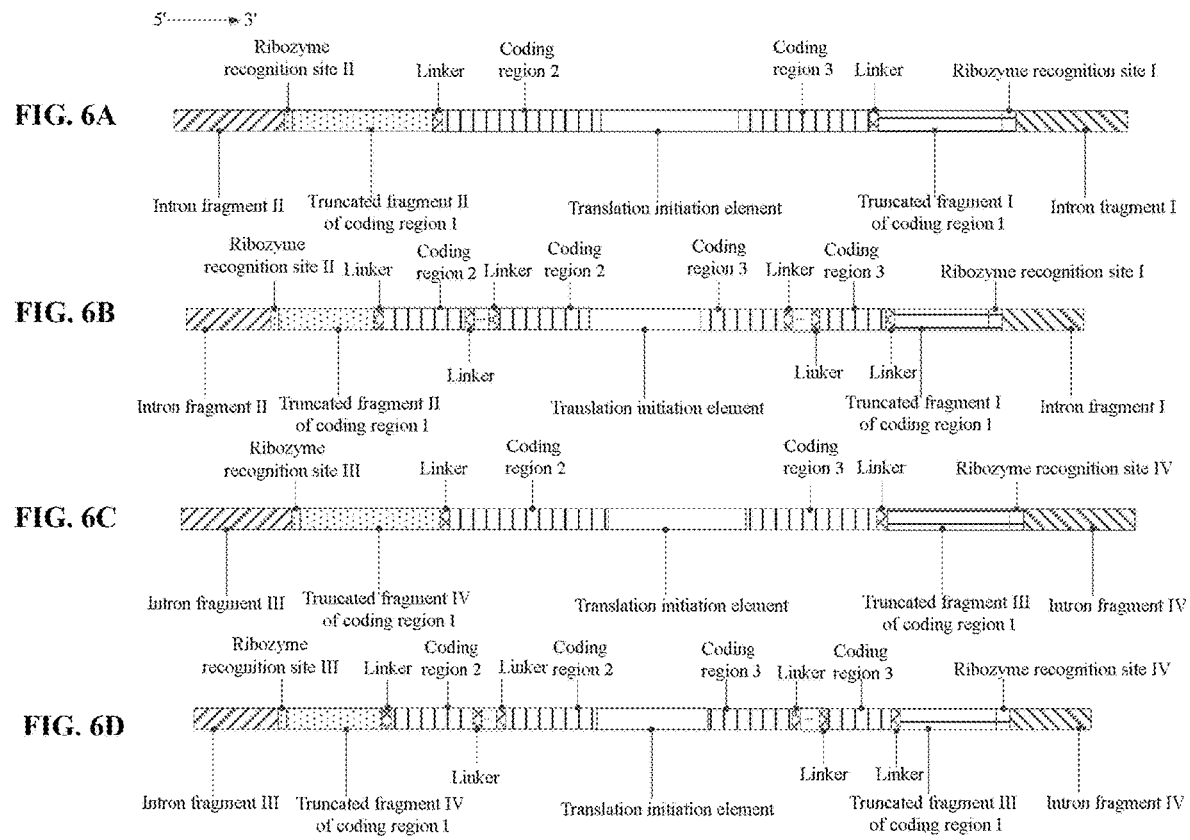

FIG.19A
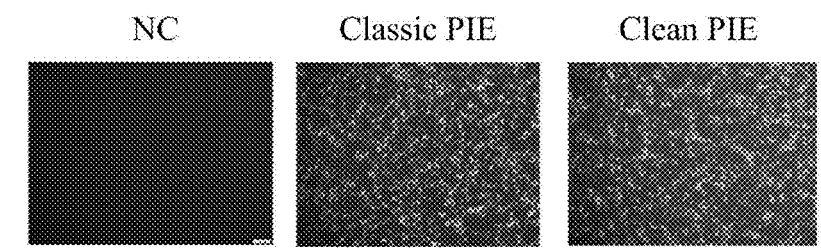
FIG.19B
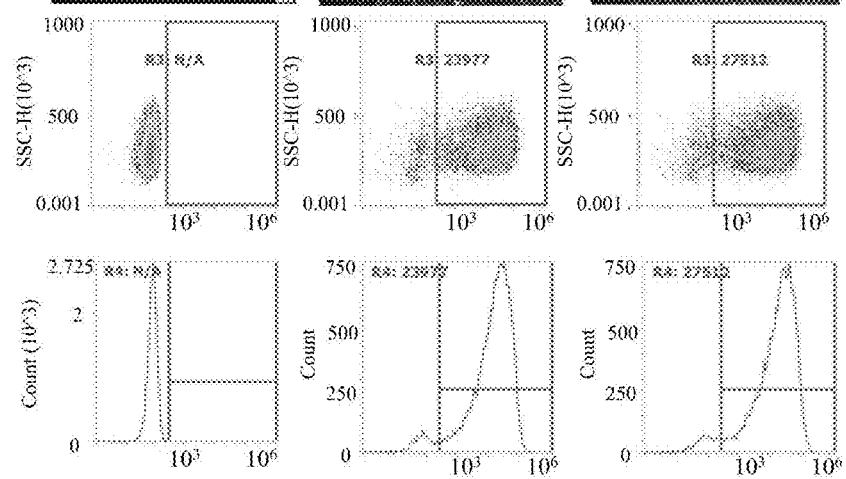
FIG.19

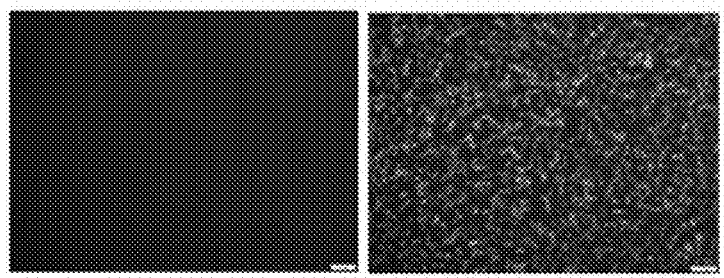
FIG. 32A
FIG. 32B
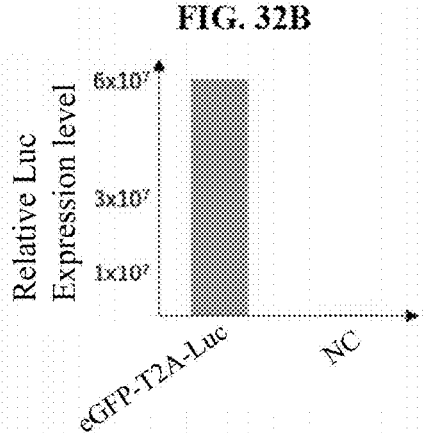
FIG. 32C
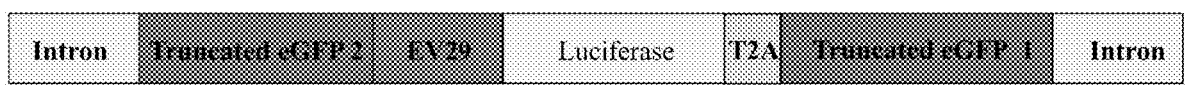

RECOMBINANT NUCLEIC ACID MOLECULE AND APPLICATION THEREOF IN PREPARATION OF CIRCULAR RNA

CROSS-REFERENCE TO RELATED APPLICATION

The present application is based upon and claims the benefit of a priority of Chinese Patent Application No. 202210200112.6, filed on Mar. 2, 2022, the entire contents of which are incorporated herein by reference.

TECHNICAL FIELD

The present disclosure relates to the fields of molecular biology and bioengineering, and in particular, to a recombinant nucleic acid molecule for preparing a circular RNA, a recombinant expression vector, a circular RNA, a composition, a method for preparing a circular RNA, a method for expressing a target polypeptide in a cell, a method for preventing or treating diseases, a method for screening a target coding region sequence, a system for screening a target coding region sequence, and a method for screening a ribozyme recognition site sequence.

BACKGROUND

A clinical experiment by the National Institutes of Health (NIH) observed that symptoms of adenosine deaminase (ADA)-deficient severe combined immunodeficiency (ADA-SCID) were significantly improved by delivering normal ADA enzyme into children with ADA-SCID[1-2], which has greatly facilitated the clinical research development of gene therapy. With the emergence of gene therapy technology, it is expected to fundamentally cure some diseases that cannot be solved by the existing traditional therapies, and make up for the deficiencies of traditional therapies. However, in the early study of gene therapy, retroviruses were typically used as delivery vectors of target genes to integrate a target fragment in the genome of a target cell through random insertion, presenting great uncertainty and danger. In recent years, with the improvement of viral vectors (lentiviral vectors, adenoviral vectors, recombinant adeno-associated virus vectors, and the like) and the development of non-viral vectors (liposome technology, lipid nanoparticles technology, microsphere technology, dendrimer technology, exosomes, and the like), gene therapy has gained interest again.

Messenger ribonucleic acid (mRNA) is transcribed from DNA and provides necessary genetic information for the next step of protein translation, with important application value in protein production, gene therapy approaches such as serving as nucleic acid vaccines, and the like. As compared with traditional vaccines, nucleic acid vaccines have various advantages such as long-lasting immune response, simple manufacturing process, and applications in tumor prevention, thus showing broad prospects in the fields of preventing acute infectious diseases, HIV, cancer, and others. Particularly, since the outbreak of the novel corona virus disease 2019 (COVID-19), research and development on nucleic acid vaccines has been significantly accelerated.

Circular RNAs (circRNAs) have been proved to synthesize protein mediated by internal ribosome entry sites (IRES) in a cap-independent manner in vitro[15]. However, most researchers still have long believed that ribosomes of eukaryotes are unable to translate circRNAs in vivo. With the emergence of RNA sequencing technology (RNA-seq), many more circRNAs have been identified[3-8], leading to increasingly more attention on their study. In addition, with the deepening of research, researchers have found that in eukaryotes, circRNAs are not only widely abundant, but also highly conserved[9]. The 5' and 3' ends in a circRNA are ligated to each other to form a closed ring, which allows circRNA to show a higher resistance to RNase and thus to enable a longer-acting and lasting expression compared to a linear mRNA [10]. In addition, circRNAs may be prepared more efficiently, rapidly, and cost effectively compared to the preparation of linear mRNAs featuring fussy capping, tailing and nucleotide modification. Because of these characteristics, although circRNA is a bran-new gene therapy method, it has been used as a vector for gene therapy for business development.

RNA circularization is a key step in preparation of circRNA. In prior art, in vivo circularization and in vitro circularization are two common methods for circularization. In eukaryotes, a spliceosome splices introns out of an immature mRNA by a method including two steps: attacking, by a 2'-hydroxy group on a specific adenosine (branch point Adenosine, bpA) in an intron, the 5' splice site to form a 3'-hydroxy group at an exon at the 5' end; and then, further attacking, by the newly formed 3'-hydroxy end, a 3' splice site with the assistance of a spliceosome, to form a linear RNA with two exons ligated together and a lariat structure. In this process, a natural circRNA is produced by back-splicing or exon skipping[3,10-11] Although in vivo circularization may ensure the sequence accuracy of the circularized circRNAs, it is still necessary to introduce plasmids into the body as therapeutics, which greatly increases the risk of integration into the genome.

In vitro circularization of RNA mainly depends on formation of a phosphodiester bond, and the most common in vitro RNA circularization methods include mainly a chemical method and an enzymatic method. In case of the chemical circularization method, a natural phosphodiester bond is mainly formed and circularized through a condensation reaction between 5'-monophosphate and 3'-hydroxyl of RNA, catalyzed by cyanogen bromide or ethyl-3-(3'-dimethylaminopropyl)-carbodiimide. However, the chemical circularization method is less efficient in ligating, and is only suitable for ligating small fragments of circRNAs[12]. In addition, the chemical groups have great potential safety hazards in gene therapy as well. Therefore, it is difficult for the chemical circularization method to be widely used.

The enzymatic method may be further divided into protease catalyzation and ribozyme catalyzation, where the protease catalyzation mainly includes catalyzing formation of the phosphodiester bond through a splint chain by T4 DNA ligase, T4 RNA ligase 1, T4 RNA ligase 2, and RtcB[13]. However, the current protease catalyzation ligation methods are less efficient in ligating large fragments of circRNAs, and it is also difficult to obtain circular messenger ribonucleotides with accurate nucleic acid sequences.

Ribozymes are a class of RNAs capable of acting as catalysts similar to proteases. There are usually three methods for preparing circRNAs by ribozyme in vitro: self-splicing of Group I intron, self-splicing of group II intron, and circularization by some subviral genomes. In case of the group II intron, a circle is typically ligated and formed via a 2'-5'diphosphate bond, whose impacts on the expression of circRNAs still needs further study. In case of ligating a circRNA through the genome of a subvirus, ribozymes in the genome of the subvirus are typically required to be introduced. As a result, some RNAs in vivo may usually become potential targets of splicing by these ribozymes. In the industry, it is a common circularization strategy to circularize circular ribonucleotides through the catalysis of the Group I introns, where *Anabaena* PIE (prematured intron exon) and T4td (thymidylate synthase of T4) PIE are the most widely used ribozyme-catalyzed self-splicing circularization systems. In the presence of guanine and divalent cations, the intron sequences of *Anabaena* PIE and T4td PIE form a specific structure to be spliced by self-catalyzation, thus allowing the ribonucleotide sequence in the middle of the intron to form a circle.

In the prior art, circRNAs show important application prospects in the fields of gene therapy vectors, in vivo expression of therapeutic proteins, and nucleic acid vaccines, but many unsolved or undiscovered problems still exist. The accuracy of the circRNA sequence is the key to its clinical application, and an important guarantee for the efficacy and safety of subsequent therapy. It has been studied of the effects of ligating and forming circRNAs with the T4 ligase, T4 td PIE system, and *Anabaena* PIE system on the RNA secondary structure. As shown in FIG. 1, compared with circularization with T4 ligase, circularization through the self-splicing of the T4 td PIE system and the *Anabaena* PIE system may result in introduction of additional exon sequences (E1, E2) into the circRNAs, which may result in substantial change in structural conformation of the circularized RNAs. Furthermore, due to the introduction of additional E1 and E2 sequences, the circRNAs obtained by using the T4 td PIE and the *Anabaena* PIE may trigger immune response in cells, resulting in degradation of the circRNA molecules in cells[14].

Chinese Patent No. CN 112399860 A discloses a vector for making circRNA, wherein the vector comprises the following elements operably connected to each other and arranged in the following sequence: a.) a 5' homology arm, b.) a 3' Group I intron fragment containing a 3' splice site dinucleotide, c.) optionally, a 5' spacer sequence, d.) a protein coding or non-coding region, e.) optionally, a 3' spacer sequence, f.) a 5' Group I intron fragments containing a 5' splice site dinucleotide, and g.) a 3' homology arm. The vector allows production of a circRNA that is translatable or biologically active inside eukaryotic cells. Although the vector may be used to prepare a circular RNA through self-splicing characteristic of PIE system, it is necessary to insert specific exon sequences into the vector to guide the splicing of intron fragments. In addition, introduction of additional exon sequences into the finally obtained circular RNAs may reduce the sequence accuracy of the circular RNAs, resulting in substantial changes in the structural conformation of the circularized RNAs, triggering immune response in cells, inducing degradation of circular RNA molecules in cells, posing potential safety hazards for circular RNAs in nucleic acid vaccines and gene therapy, thereby limiting application of circular RNAs in clinical disease treatment.

REFERENCES

[1] Kantoff P W, Kohn D B, Mitsuya H, et al. Correction of adenosine deaminase deficiency in cultured human T and B cells by retrovirus-mediated gene transfer [J]. Proceedings of the National Academy of Sciences, 1986, 83(17): 6563-6567.

[2] Kohn D B, Mitsuya H, Ballow M, et al. Establishment and characterization of adenosine deaminase-deficient human T cell lines [J]. The Journal of Immunology, 1989, 142(11): 3971-3977.

[3] Kelly S, Greenman C, Cook P R, et al. Exon skipping is correlated with exon circularization [J]. Journal of molecular biology, 2015, 427(15): 2414-2417.

[4] Djebali S, Davis C A, Merkel A, et al. Landscape of transcription in human cells [J]. Nature, 2012, 489(7414): 101-108.

[5] Guttman M, Garber M, Levin J Z, et al. Ab initio reconstruction of cell type-specific transcriptomes in mouse reveals the conserved multi-exonic structure of lincRNAs [J]. Nature biotechnology, 2010, 28(5): 503-510.

[6] Mortazavi A, Williams B A, McCue K, et al. Mapping and quantifying mammalian transcriptomes by RNA-Seq [J]. Nature methods, 2008, 5(7): 621-628.

[7] Wang E T, Sandberg R, Luo S, et al. Alternative isoform regulation in human tissue transcriptomes[J]. Nature, 2008, 456(7221): 470-476.

[8] Wilusz J E, Sunwoo H, Spector D L. Long noncoding RNAs: functional surprises from the RNA world [J]. Genes & development, 2009, 23(13): 1494-1504.

[9] Wilusz J E. A 360 view of circular RNAs: from biogenesis to functions [J]. Wiley Interdisciplinary Reviews: RNA, 2018, 9(4): e1478.

[10] Jeck W R, Sharpless N E. Detecting and characterizing circular RNAs [J]. Nature biotechnology, 2014, 32(5): 453-461.

[11] Wang Y, Wang Z. Efficient backsplicing produces translatable circular mRNAs [J]. RNA, 2015, 21(2): 172-179.

[12] Gaglione M, Di Fabio G, Messere A. Current Methods in Synthesis of Cyclic Oligonucleotides and Analogues [J]. Current Organic Chemistry, 2012, 16(11): 1371-1389.

[13] Obi P, Chen Y G. The Design and Synthesis of Circular RNAs [J]. Methods, 2021.

[14] Liu C X, Guo S K, Nan F, et al. RNA circles with minimized immunogenicity as potent PKR inhibitors [J]. Molecular Cell, 2021.

[15] Chen C, Sarnow P. Initiation of protein synthesis by the eukaryotic translational apparatus on circular RNAs [J]. Science, 1995, 268(5209): 415-417.

SEQUENCE LISTING

This application contains a sequence listing that has been submitted electronically as an XML file named "53596-0005001.XML." The XML file, created on Jul. 19, 2022, s 145,622 bytes in size. The material in the XML file is hereby incorporated by reference in its entirety.

SUMMARY

Problems to be Solved by the Disclosure

In view of the problems existing in the prior art, such as inclusion of additional exon sequences in circular RNAs caused by using PIE system to prepare circular RNAs in vitro in the prior art method, resulting in changes in structural conformation of the circular RNAs, which leads to cellular immune response and reduction of the circular RNA molecules in vivo, posing potential safety hazards in nucleic acid vaccines and gene therapy, the present disclosure provides a recombinant nucleic acid molecule for preparing a circular RNA in vitro. The circular RNA prepared using it can avoid introduction of additional exon sequences, improve sequence accuracy of circular RNA molecules, reduce changes in secondary structure of circular RNAs, and further reduce immunogenicity of circular RNAs, improve stability of circular RNAs in cells, and reduce safety risks of circular RNAs in clinical application, thus showing wide application prospects in fields of mRNA infectious disease vaccines, therapeutic mRNA tumor vaccines, mRNA-based dendritic cell (DC) tumor vaccines, mRNA-based gene therapy, protein supplement therapy, and the like.

Means for Solving the Problems (1) A recombinant nucleic acid molecule for preparing a circular RNA, the recombinant nucleic acid molecule being selected from any one of (i) to (ii):
  (i) the recombinant nucleic acid molecule including elements arranged in the following order in the 5' to 3' direction:
  an intron fragment II, a truncated fragment II of a coding element, a translation initiation element, a truncated fragment I of a coding element, and an intron fragment I;
  where, a 3' end of the truncated fragment I of the coding element includes a ribozyme recognition site I that consists of a first predetermined number of nucleotides located at the 3' end of the truncated fragment I of the coding element;
  a 5' end of the truncated fragment II of the coding element includes a ribozyme recognition site II that consists of a second predetermined number of nucleotides located at the 5' end of the truncated fragment II of the coding element;
  the nucleotide sequence of the truncated fragment I of the coding element and the nucleotide sequence of the truncated fragment II of the coding element form a coding element sequence encoding at least one target polypeptide in the 5' to 3' direction; the nucleotide sequence of the truncated fragment I of the coding element corresponds to a partial sequence close to the 5' direction in the coding element sequence, and the nucleotide sequence of the truncated fragment II of the coding element corresponds to a remaining partial sequence close to the 3' direction in the coding element sequence;
  the nucleotide sequence of the intron fragment I and the nucleotide sequence of the intron fragment II form an intron sequence in the 5' to 3' direction; the nucleotide sequence of the intron fragment I includes a partial sequence close to the 5' direction in the intron sequence, and the nucleotide sequence of the intron fragment II includes a remaining partial sequence close to the 3' direction in the intron sequence;
  alternatively, (ii) the recombinant nucleic acid molecule including elements arranged in the following order in the 5' to 3' direction:
  an intron fragment III, a truncated fragment IV of a coding element, a translation initiation element, a truncated fragment III of a coding element, and an intron fragment IV;
  where, a 3' end of the truncated fragment III of the coding element includes a ribozyme recognition site IV that consists of a second predetermined number of nucleotides located at the 3' end of the truncated fragment III of coding element;
  a 5' end of the truncated fragment IV of the coding element includes a ribozyme recognition site III that consists of a first predetermined number of nucleotides located at the 5' end of the truncated fragment IV of coding element;
  the nucleotide sequence of the truncated fragment III of the coding element and the nucleotide sequence of the truncated fragment IV of the coding element form a coding element sequence encoding at least one target polypeptide in the 5' to 3' direction; the nucleotide sequence of the truncated fragment III of the coding element corresponds to a partial sequence close to the 5' direction in the coding element sequence, and the nucleotide sequence of the truncated fragment IV of the coding element corresponds to a remaining partial sequence close to the 3' direction in the coding element sequence;
  where, the sequence of the intron fragment III is a reverse sequence or a reverse complementary sequence of the nucleotide sequence of the intron fragment I, and the sequence of intron fragment IV is a reverse sequence or a reverse complementary sequence of the nucleotide sequence of the intron fragment II; the sequence of the ribozyme recognition site III is a reverse sequence of the nucleotide sequence of the ribozyme recognition site I, and the sequence of the ribozyme recognition site IV is a reverse sequence of the nucleotide sequence of the ribozyme recognition site II.

(2) The recombinant nucleic acid molecule according to (1), where the intron fragment I and the intron fragment II are derived from Group I intron, the ribozyme recognition site I is derived from a natural exon sequence ligated to the 5' end of the intron fragment I, and the ribozyme recognition site II is derived from a natural exon sequence ligated to the 3' end of the intron fragment II; and
  optionally, the Group I intron is derived from any one of the following Group I introns: phage T4 td gene, *Anabaena* tRNA$^{Leu}$, TpaCOX2, and Ptu.

(3) The recombinant nucleic acid molecule according to (1) or (2), where the first predetermined number of nucleotides is selected from 3 to 100 nucleotides, preferably 3 to 50 nucleotides, and more preferably 3 to 10 nucleotides.

(4) The recombinant nucleic acid molecule according to any one of (1) to (3), where the second predetermined number of nucleotides is selected from 1 to 100 nucleotides, preferably 1 to 50 nucleotides, and more preferably 1 to 10 nucleotides.

(5) The recombinant nucleic acid molecule according to any one of (1) to (4), where a sum of the first predetermined number and the second predetermined number is not equal to 3y, where y≥1 and y is an integer.

(6) The recombinant nucleic acid molecule according to any one of (1) to (5), where the translation initiation element includes a sequence with an activity of initiating translation of an editing region; and
  optionally, the sequence with the activity of initiating translation of an editing region is selected from one of or a combination of two or more of: an IRES sequence, a 5' UTR sequence, a Kozak sequence, a sequence with m$^6$A modification, and a complementary sequence of ribosome 18S rRNA.

(7) The recombinant nucleic acid molecule according to any one of (1) to (6), where the recombinant nucleic acid molecule is used for preparing a circular RNA including a coding element, where the coding element in the circular RNA includes a coding region 1, optionally (a) at least one coding region 2, and optionally (b) at least one coding region 3;
  the truncated fragment I of the coding element and the truncated fragment II of the coding element form the coding region 1, optionally (a) the at least one coding region 2, and optionally (b) the at least one coding region 3; the recombinant nucleic acid molecule includes elements arranged in the order shown in any one of (i) to (iv) in the 5' to 3' direction:
(i) the intron fragment II, the truncated fragment II of the coding region 1, the at least one coding region 2, the translation initiation element, the truncated fragment I of the coding region 1, and the intron fragment II;
(ii) the intron fragment II, the truncated fragment II of the coding region 1, the translation initiation element, the at least one coding region 3, the truncated fragment I of coding region 1, and the intron fragment I;
(iii) the intron fragment II, the truncated fragment II of the coding region 1, the at least one coding region 2, the translation initiation element, the at least one coding region 3, the truncated fragment I of the coding region 1, and the intron fragment I;
(iv) the intron fragment II, the truncated fragment II of the coding region 1, the translation initiation element, the truncated fragment I of the coding region 1, and the intron fragment I;
alternatively, the truncated fragment III of the coding element and the truncated fragment IV of the coding element form the coding region 1, optionally (a) the at least one coding region 2, and optionally (b) the at least one coding region 3; the recombinant nucleic acid molecule includes elements arranged in the order shown in any one of (v) to (viii) in the 5' to 3' direction:
(v) the intron fragment III, the truncated fragment IV of the coding region 1, the at least one coding region 2, the translation initiation element, the truncated fragment III of the coding region 1, and the intron fragment IV;
(vi) the intron fragment III, the truncated fragment IV of the coding region 1, the translation initiation element, the at least one coding region 3, the truncated fragment III of the coding region 1, and the intron fragment IV;
(vii) the intron fragment III, the truncated fragment IV of the coding region 1, the at least one coding region 2, the translation initiation element, the at least one coding region 3, the truncated fragment III of the coding region 1, and the intron fragment IV;
(viii) the intron fragment III, the truncated fragment IV of the coding region 1, the translation initiation element, the truncated fragment III of the coding region 1, and the intron fragment IV;
where, the coding region 1, each coding region 2 and each coding region 3 encode any type of target polypeptides independently of one another.
(8) The recombinant nucleic acid molecule according to (7), where the recombinant nucleic acid molecule includes one or both elements of (i) to (ii):
(i) a linker located between the truncated fragment II of the coding region 1, and the coding region 2;
(ii) a linker located between the coding region 3 and the truncated fragment I of the coding region 1;
alternatively, the recombinant nucleic acid molecule includes one or both elements of (iii) to (iv):
(iii) a linker located between the truncated fragment IV of the coding region 1, and the coding region 2;
(iv) a linker located between the coding region 3 and the truncated fragment III of the coding region 1;
optionally, the coding region 2 has a quantity of at least 2, and the recombinant nucleic acid molecule includes a linker located between any two coding regions 2;
optionally, the coding region 3 has a quantity of at least 2, and the recombinant nucleic acid molecule includes a linker located between any two coding regions 3; and preferably, the linker is a 2A peptide-encoding polynucleotide.
(9) The recombinant nucleic acid molecule according to any one of (1) to (6), where the recombinant nucleic acid molecule is used for preparing a circular RNA including a coding element; where the coding element in the circular RNA includes a coding region 1, at least one coding region 4, and a translation initiation element located between any two adjacent coding regions;
the truncated fragment I of the coding element and the truncated fragment II of the coding element form the coding region 1, the at least one coding region 4, and the translation initiation element located between any two adjacent coding regions; or,
the truncated fragment III of the coding element and the truncated fragment IV of the coding element form the coding region 1, the at least one coding region 4, and the translation initiation element located between any two adjacent coding regions.
(10) The recombinant nucleic acid molecule according to any one of (1) to (9), where the target polypeptide is a human-derived protein or non-human derived protein; and
optionally, the target polypeptide is selected from one of or a combination of two or more of: an antigen, an antibody, an antigen-binding fragment, a fluorescent protein, a protein with therapeutic activity, and a protein with gene-editing activity.
(11) The recombinant nucleic acid molecule according to any one of (1) to (10), where the recombinant nucleic acid molecule further includes an insertion element between the truncated fragment II and the translation initiation element, or an insertion element between the truncated fragment IV and the translation initiation element; the insertion element is at least one selected from the group consisting of (i) to (iii):
(i) a transcriptional regulatory element, (ii) a translational regulatory element, and (iii) a purification element;
preferably, the insertion element is ligated to the 5' end of any translation initiation element;
optionally, the insertion element comprises a sequence selected from one of or a combination of two or more of:
an untranslated region sequence, a polyA sequence, an aptamer sequence, a riboswitch sequence, and a transcriptional regulator-binding sequence.
(12) The recombinant nucleic acid molecule according to any one of (1) to (11), where the recombinant nucleic acid molecule further includes a 5' homologous arm and a 3' homologous arm, and the nucleotide sequence of the 5' homologous arm is hybridized with the nucleotide sequence of the 3' homologous arm;
the 5' homologous arm is ligated to the 5' end of the intron fragment II, and the 3' homologous arm is ligated to the 3' end of the intron fragment I; or, the 5' homologous arm is ligated to the 5' end of the intron fragment III, and the 3' homologous arm is ligated to the 3' end of the 3' intron fragment IV.
(13) The recombinant nucleic acid molecule according to any one of (1) to (12), where a nucleotide sequence derived from an exon is not included in any one of the intron fragment I, the translation initiation element, or the intron fragment II, or between any two of the intron fragment I, the truncated fragment II of the coding element, the translation initiation element, the truncated fragment I of the coding element, and the intron fragment II; or,
a reverse sequence or reverse complementary sequence of a nucleotide sequence derived from an exon is not included in any one of the intron fragment III, the translation initiation element, and the intron fragment IV, or between any two of the intron fragment III, the truncated fragment IV of the coding element, the translation initiation element, the truncated fragment III of the coding element, and the intron fragment IV.

(14) A recombinant expression vector, including the recombinant nucleic acid molecule according to any one of (1) to (13).

(15) Use of the recombinant nucleic acid molecule according to any one of (1) to (13) or the recombinant expression vector according to (14) for preparing a circular RNA in vitro.

(16) A method for preparing a circular RNA in vitro, including the steps of:
  transcribing the recombinant nucleic acid molecule according to any one of (1) to (13) or the recombinant expression vector according to (14) to form a cyclization precursor nucleic acid molecule;
  cyclizing the cyclization precursor nucleic acid to obtain the circular RNA; and
  optionally, further including the step of purifying the circular RNA.

(17) A circular RNA prepared by the recombinant nucleic acid molecule according to any one of (1) to (13), the recombinant expression vector according to (14), or the method according to (16).

(18) A circular RNA, including elements arranged in the following order in the 5' to 3' direction:
  a translation initiation element, a coding element for encoding at least one target polypeptide;
  optionally, the circular RNA includes an insertion element located between the 5' end of the translation initiation element and the 3' end of the coding element;
  optionally, the translation initiation element, the target polypeptide or the insertion element are defined according to any one of (6) and (10) to (11).

(19) The circular RNA according to (18), where the coding element of the circular RNA includes a coding region 1, and at least one in the group consisting of (i) to (ii):
  (i) at least one coding region 2, and (ii) at least one coding region 3; where each coding region encodes any type of target polypeptide independently of one another;
  preferably, any two adjacent coding regions are linked by a linker.

(20) The circular RNA according to (18), where the coding element of the circular RNA includes the coding region 1 and at least one coding region 4, and the 5' end of any coding region is ligated to a translation initiation element.

(21) The circular RNA according to any one of (18) to (20), where the insertion element is ligated to the 5' end of any translation initiation element.

(22) A composition including the recombinant nucleic acid molecule according to any one of (1) to (13), the recombinant expression vector according to (14), or the circular RNA according to any one of (17) to (21); preferably the circular RNA according to any one of (17) to (21);
  optionally, the composition further includes one or more pharmaceutically acceptable carriers; and
  optionally, the pharmaceutically acceptable carrier is selected from a lipid, a polymer or a lipid-polymer complex.

(23) A method for expressing a target polypeptide in a cell, where the method includes the step of delivering the circular RNA according to any one of (17) to (21) or the composition according to (18) into the cell.

(24) A method for preventing or treating diseases, where the method includes administering the circular RNA according to any one of (17) to (21) or the composition according to (22) to a subject.

(25) A method for screening a target coding region sequence including a ribozyme recognition site, where the coding region sequence is a coding sequence of a target polypeptide; the method includes the following steps:
  S1, extracting m amino acid units from the target polypeptide including q amino acids in the N-terminal-to-C-terminal direction, with each of the amino acid units including n amino acids; where at least one repeated amino acid is included between any two adjacent amino acid units, n is an integer and n≥2, m is an integer and m≥1; preferably, m=q+1−n;
  S2, determining m codon sequence sets, where each of the codon sequence sets includes codon sequences corresponding to each of the amino acid units;
  S3, traversing the m codon sequence sets to obtain a matching value of each codon sequence in each of the codon sequence sets with a target motif;
  S4, determining a target codon sequence in the codon sequence sets based on the matching value, where the position of the target codon sequence corresponding to the coding region sequence is the implantation position of the ribozyme recognition site, and the coding region sequence including the target codon sequence at the implantation position is the target coding region sequence including the ribozyme recognition site.

(26) The method according to (25), where the target motif includes a ribozyme recognition site sequence that is formed by ligating the nucleotide sequence of a ribozyme recognition site I to the nucleotide sequence of a ribozyme recognition site II; or is formed by ligating the nucleotide sequence of a ribozyme recognition site III to the nucleotide sequence of a ribozyme recognition site IV;
  at least one of the 5' end and the 3' end of the ribozyme recognition site sequence is ligated to x nucleotide to obtain a target motif with 3n nucleotide; where each x is an integer ≥0 independently of one another, and each ligated nucleotide is selected from any type of nucleotide independently of one another.

(27) The method according to (25) or (26), where the target motif includes an effective base pair that includes two bases at the linking position of ribozyme recognition site I and ribozyme recognition site II; the obtaining a matching value of each codon sequence in each of the codon sequence sets with a target motif includes:
  determining whether the base at a position corresponding to the effective base pair in the codon sequence is an effective base, and if the codon sequence does not include an effective base pair, disabling output of an alignment value of the codon sequence;
  if the codon sequence includes an effective base pair, determining the alignment value between each base in each codon sequence with the corresponding base in the target motif in the 5' to 3' direction; and
  obtaining the matching value of each codon sequence with the target motif based on the alignment value of each base in each codon sequence.

(28) The method according to (27), where the obtaining a matching value of each codon sequence in each of the codon sequence sets with a target motif further includes:
  determining whether each codon sequence in each of the codon sequence sets is hybridized with an intron sequence to obtain a complementary value of each codon sequence in each of the codon sequence sets;

determining the matching value of each codon sequence in each of the codon sequence sets with the target motif based on the alignment value and the complementary value.

(29) A screening system for screening a target coding region sequence including a ribozyme recognition site, where the coding region sequence is a nucleotide sequence encoding a target polypeptide;

the screening system includes:
a target motif constructing module configured to ligate x nucleotide to at least one of the 5' end and the 3' end of the ribozyme recognition site sequence to obtain a target motif with 3n nucleotide; where each x is an integer ≥0 independently of one another, and each ligated nucleotide is selected from any type of nucleotide independently of one another;
an amino acid unit extraction module configured to extract m amino acid units from the target polypeptide including q amino acids in the N-terminal-to-C-terminal direction, with each of the amino acid units including n amino acids; where at least one repeated amino acid is included between any two adjacent amino acid units, n is an integer and n≥2, m is an integer and m≥1; preferably, m=q+1−n;
a codon sequence set extraction module configured to determine m codon sequence sets, where each of the codon sequence sets includes codon sequences corresponding to each of the amino acid units;
a matching value calculation module configured to traverse the m codon sequence sets to obtain a matching value of each codon sequence in each of the codon sequence sets with a target motif;
a target codon sequence screening module configured to determine a target codon sequence in the codon sequence sets based on the matching value, where the position of the target codon sequence corresponding to the coding region sequence is the implantation position of the ribozyme recognition site, and the coding region sequence including the target codon sequence at the implantation position is the target coding region sequence comprising the ribozyme recognition site;
preferably, the target motif includes a ribozyme recognition site sequence that is formed by ligating the nucleotide sequence of a ribozyme recognition site I to the nucleotide sequence of a ribozyme recognition site II; or is formed by ligating the nucleotide sequence of a ribozyme recognition site III to the nucleotide sequence of a ribozyme recognition site IV; and
at least one of the 5' end and the 3' end of the ribozyme recognition site sequence is ligated to x nucleotide to obtain the target motif with 3n nucleotide; where each x is an integer ≥0 independently of one another, and each ligated nucleotide is selected from any type of nucleotide independently of one another.

(30) The screening system according to (29), where the target motif includes an effective base pair that corresponds to two bases at the linking position of the ribozyme recognition site I and the ribozyme recognition site II; where the matching value calculation module includes:
an effective base pair determination unit configured to determine whether the base at a position corresponding to the effective base pair in the codon sequence is an effective base, and if the codon sequence does not includes the effective base pair, disabling output of the alignment value of the codon sequence;
an alignment value determination unit configured to determine the alignment value between each base in each codon sequence with the corresponding base in the target motif in the 5' to 3' direction;
a matching value output unit configured to obtain the matching value of each codon sequence with the target motif based on the alignment value of each base in each codon sequence.

(31) The screening system according to (30), where the matching value calculation module further includes:
a complementary value calculation module configured to determine whether each codon sequence in each of the codon sequence sets is hybridized with an intron sequence to obtain a complementary value of each codon sequence in each of the codon sequence sets;
the matching value output unit configured to determine the matching value of each codon sequence in each of the codon sequence sets with the target motif based on the alignment value and the complementary value.

(32) A method for screening a ribozyme recognition site sequence, where the method includes:
determining a sequence to be screened, and the sequence to be screened includes an intron sequence derived from Group I intron, a first exon sequence ligated to the 5' end of the intron sequence, and a second exon sequence ligated to the 3' end of the intron sequence;
obtaining a predicted RNA secondary structure based on the sequence to be screened;
obtaining a ribozyme recognition site I with ribozyme recognition activity in the first exon sequence and a ribozyme recognition site II with ribozyme recognition activity in the second exon sequence based on the predicted RNA secondary structure;
determining the ribozyme recognition site sequence based on the nucleotide sequence of the ribozyme recognition site I and the nucleotide sequence of the ribozyme recognition site II;
optionally, the ribozyme recognition site sequence includes at least one in the group consisting of (i) to (iv):
(i) the nucleotide sequence of the ribozyme recognition site I,
(i) the nucleotide sequence of the ribozyme recognition site II,
(iii) a mutant sequence of the ribozyme recognition site I with ribozyme recognition activity,
(iv) a mutant sequence of the ribozyme recognition site II with ribozyme recognition activity,
preferably, the ribozyme recognition site sequence is formed by ligating any one of (i) and (iii) to any one of (ii) and (iv).

(33) The method according to (32), where the nucleotide sequence of the ribozyme recognition site I is hybridized with a leader sequence in the intron sequence, or the nucleotide sequence of the ribozyme recognition site II is hybridized with a leader sequence in the intron sequence.

(34) The method according to (32) or (33), where the method includes:
sequentially replacing the base on the ribozyme recognition site I to obtain the mutant sequence of the ribozyme recognition site I with ribozyme recognition activity, or
sequentially replacing the base on the ribozyme recognition site II to obtain the mutant sequence of the ribozyme recognition site II with ribozyme recognition activity.

Effects of Disclosure

In some embodiments, the recombinant nucleic acid molecule for preparing a circular RNA provided by the present disclosure includes: an intron fragment II, a truncated fragment II of a coding element, a translation initiation element, a truncated fragment I of a coding element, and an intron fragment I. The circular RNA is prepared by the recombinant nucleic acid molecule in vitro, in which under the guidance of the intron sequence, a linear nucleic acid molecules are ligated to form the circular RNA through the successive cleavage occurred at a splice site at the 3' end of the truncated fragment I of a coding element and a splice site at the 5' end of the truncated fragment II of a coding element, and a coding element for encoding at least one target polypeptide is formed by ligating the truncated fragment I of the coding element and the truncated fragment II of the coding element. In addition, as the ribozyme recognition site I and the ribozyme recognition site II are formed inside the truncated fragments of the coding element, no additional exon sequence is required to be introduced into the recombinant nucleic acid molecule, thus excluding the additional exon sequence from the circular RNA, thereby improving the sequence accuracy of the circular RNA molecule.

The recombinant nucleic acid molecule of the present disclosure provides a Clean PIE system with a novel structure for preparing a circular RNA in vitro. As compared to a classic PIE system, the Clean PIE system provided by the present disclosure is capable of improving the sequence accuracy of the circular RNA molecule, reducing changes in the secondary structure of the circular RNA, and further reducing immunogenicity of the circular RNA, improving stability of the circular RNA in cells, reducing safety risk of circular RNAs in clinical application, and enabling large-scale production of circular RNAs in vitro, thus showing wide application prospects in the fields of mRNA infectious disease vaccines, therapeutic mRNA tumor vaccines, mRNA-based dendritic cell (DC) tumor vaccines, mRNA-based gene therapy, protein supplement therapy, and the like.

In some embodiments, the recombinant nucleic acid molecule for preparing a circular RNA provided by the present disclosure includes: an intron fragment III, a truncated fragment IV of a coding element, a translation initiation element, a truncated fragment III of a coding element, and an intron fragment IV. In case that the recombinant nucleic acid molecule is used for preparing a circular RNA in vitro, under the guidance of the intron sequence, linear nucleic acid molecules are ligated to form the circular RNA through successive cleavage occurred at the splice site at the 5' end of the truncated fragment IV of the coding element and the splice site at the 3' end of the truncated fragment III of the coding element, and the truncated fragment III of the coding element and the truncated fragment IV of the coding element are ligated to form the coding element for encoding at least one target polypeptide. In addition, it avoids introduction of additional exon sequences into the circular RNA, which may improve sequence accuracy, reduce immunogenicity, improve stability, and reduce safety risks of clinical application thereof, and enabling large-scale production of the circular RNA in vitro, thus showing good application prospects in the fields of nucleic acid vaccines and gene therapy.

In some embodiments, as no spacer, homology arm, exon and other fragments are required to be introduced, the recombinant nucleic acid molecule for preparing circular RNAs provided by the present disclosure is structurally simple, such that the resulting circular RNA is safe and suitable for large-scale industrial production of circular RNAs in vitro.

In some embodiments, in the recombinant nucleic acid molecule for preparing a circular RNA provided by the present disclosure, translation initiation elements are selective from a variety of sequences, each of which allows for efficient translation of the coding region in a circular RNA, thus providing selectivity from a variety of sequences for preparation of a circular RNA.

In some embodiments, in the recombinant nucleic acid molecule for preparing a circular RNA provided by the present disclosure, an insertion element with different functions may be further introduced, such as a transcriptional regulatory element, a translational regulatory element or a purification element into the circular RNA, providing specific regulation of target polypeptides expressed by the circular RNA. In addition, the in vitro purification of circular RNA may specifically regulate the expression abundance of target polypeptides, improving the disease treatment effects of circular RNAs.

In some embodiments, the circular RNA provided by the present disclosure is prepared by using the recombinant nucleic acid molecule described above. With no additional exon sequences introduced, the circular RNA has a high sequence accuracy, small changes in the secondary structure, high biological safety and structural stability, and low immunogenicity, thus suitable for the field of clinical disease treatment.

In some embodiments, in the method for screening a target coding region sequence provided by the present disclosure, the target coding region sequence including a ribozyme recognition site is obtained by sorting the degenerate codon sequence of the amino acid of the target polypeptide, aligning it with the target motif, and scoring. The target coding region sequence may be truncated at the position of the ribozyme recognition site to obtain the fragment I of the coding element and the truncated fragment II of the coding element, or the truncated fragment III of the coding element and the truncated fragment IV of the coding element. The ribozyme recognition site is inserted in the truncated fragments of the coding element, which avoids introduction of additional exon sequences into the circular RNA. The method for screening a target coding region sequence provided by the present disclosure is suitable for integrating ribozyme recognition sites in any type of PIE system into the coding region sequence, showing wide application prospects.

BRIEF DESCRIPTION OF THE DRAWINGS

FIGS. 5A through 5D show schematic structural diagrams of a recombinant nucleic acid molecule for preparing a circRNA according to the present disclosure (a Clean PIE system).

FIGS. 6A through 6D show a schematic structural diagram of a recombinant nucleic acid molecule for preparing a circRNA according to the present disclosure (a Clean PIE system).

FIGS. 19A and 19B show detection results of in vitro expression level of circular mRNAs prepared by a classic PIE system, and a Clean PIE system of the present disclosure, respectively.

FIGS. 32A through 32C shows detection results of protein expression of eGFP and firefly Luciferase expressed by circular mRNAs containing different coding regions ligated in tandem by T2A.

DETAILED DESCRIPTION

Definitions

When used in conjunction with the terms "comprising", "including" or "containing" in the claims and/or the specification, the word "a" or "an" may refer to "one", but it may also refer to "one or more", "at least one", and "one or more than one".

As used in the claims and the specification, the words "comprising", "having", "including" or "containing" are inclusive or open-ended, and do not exclude additional elements or method steps that are not cited.

Throughout this application, the term "about" is intended to refer to a value that includes standard deviations of errors of a device or method used to measure this value.

Although the term "or" as used in this disclosure may be defined just as alternatives and "and/or", the term "or" in the claims refers to "and/or", unless expressly defined only as alternatives or alternatives that are mutually exclusive.

The terms "polypeptide", "peptide", and "protein" as used herein are interchangeable and are amino acid polymers of any length. The polymer, linear or branched, may contain modified amino acids, and may be separated by non-amino acids. The term also includes amino acid polymers that have been modified, for example, by disulfide bond formation, glycosylation, lipidation, acetylation, phosphorylation, or any other operation, such as conjugation with labeling components.

As used herein, the "PIE system", also known as permuted introns and exons, is a method for ligating to form a circular RNA by a self-splicing system of Group I intron.

As used herein, the "Group I intron" has a self-splicing system for circularization in the presence of GTP and $Mg^{2+}$.

Figure 34:
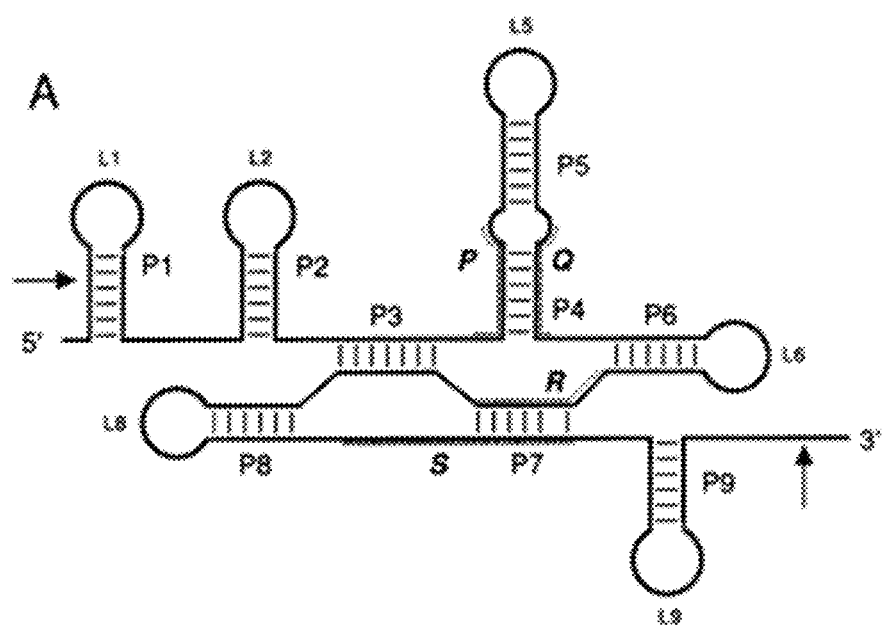
FIG. 34 shows structural characteristics of Group I intron.

Group I introns are a class of huge ribozymes capable of self-splicing, which are widely found in many species, mainly being involved in catalytic excision of precursors of mRNA, tRNA and rRNA. The core secondary structure thereof typically includes nine pairing regions (P1-P9) and corresponding loop regions (L1-L9) (FIG. 34). Splicing of Group I introns is processed by two sequential transesterification reactions. The exogenous guanosine or guanosine nucleotide (G) first docks onto the active G-binding site located in P7, and its 3'-OH is aligned to attack the phosphodiester bond at the 5' splice site located in P1, resulting in a free 3'-OH group at the upstream exon and the exogenous G being attached to the 5' end of the intron. Then the terminal G (omega G) of the intron swaps the exogenous G and occupies the G-binding site to organize the second ester-transfer reaction: the 3'-OH group of the upstream exon in P1 is aligned to attack the 3' splice site in P10, leading to the ligation of the adjacent upstream and downstream exons and release of the catalytic intron. Furthermore, the sequence of the segment joining P6 and P7 is J6/7 sequence, and the sequence of the segment joining P8 and P7 is J8/7 sequence. The Group I intron typically includes structural characteristics as shown in FIG. 34 (from Burke J M, Belfort M, Cech T R, et al. Structural Conventions for Group I introns [J]. Nucleic Acids Research, 1987, 15 (18): 7217-7221).

As used herein, an "internal guide sequence" typically refers to the nucleotide sequence of a fragment of Group I intron that is mutually paired with a corresponding exon sequence by Watson-Crick pairing or wobble pairing, generally in a P1 stem in a Group I intron.

As used herein, a "ribozyme" is intended to refer to RNA with catalytic activity. In some embodiments, a "ribozyme recognition site" herein refers to a polynucleotide sequence that may be recognized by the ribozyme and an internal broken of a phosphodiester bond can by occurred when RNA forms a ribozyme molecule with catalytic function.

As used herein, the term "circular nucleic acid molecule" refers to a nucleic acid molecule with a closed loop. In some embodiments, the circular nucleic acid molecule is a circular RNA molecule. More specifically, the circular nucleic acid molecule is a circular mRNA molecule.

As used herein, the term "linear RNA" refers to a circular RNA precursor capable of forming a circular RNA through a circularization reaction, which is typically formed by transcription of a linear DNA molecule (for example, vectors containing recombinant nucleic acid molecules, and the like).

As used herein, the term "IRES", also known as "internal ribosome entry site", is a translation control sequence, generally located at the 5' end of a gene of interest, and enables translation of RNA in a cap-independent manner. The transcribed IRES may directly bind to a ribosome subunit, such that a start codon of mRNA is properly oriented in the ribosome for translation. The IRES sequence is usually located in the 5' UTR of mRNA (immediately upstream of the start codon). The IRES functionally replaces the need for various protein factors that interact with a translation mechanism of eukaryotes.

As used herein, the term "translation initiation element" refers to any sequence element that may recruit ribosomes and initiate a translation process of RNA molecules. Illustratively, translation initiation elements include an IRES element, an $m^6A$-modified sequence, or an initiation sequence for rolling circle translation, and the like.

The terms "coding region", "protein coding region", and "open reading frame (ORF)" may be used interchangeably herein. A coding region starts with a start codon, with consecutive nucleotide sequences with protein-encoding potency. In some embodiments, the coding region ends with a stop codon. In other embodiments, the coding region may not contain the stop codon.

The term "coding element" herein is formed in a circular RNA prepared by using a Clean PIE system (e.g., a recombinant nucleic acid molecule, a recombinant expression vector, or the like) of the present disclosure, and is used to encode at least one target polypeptide. Therefore, the coding element contains at least one coding region. Illustratively, coding elements contain 1, 2, 3, 4, 5, 10, 15, 20, 25, 30, 35, 40, 45, 50 or more coding regions (including any integer value between any two numbers above). Moreover, a ribozyme recognition site is provided inside any one or more coding regions.

The "ribozyme recognition site" herein consists of a ribozyme recognition site I and a ribozyme recognition site II. It should be noted that the ribozyme recognition site is arranged within a coding region contained in the coding element. Accordingly, the ribozyme recognition site I and ribozyme recognition site II are only formed within the coding region contained in the coding element. Alternatively, the ribozyme recognition site consists of a ribozyme recognition site III and a ribozyme recognition site IV. It should be noted that the ribozyme recognition site is arranged within a coding region contained in the coding element. Accordingly, the ribozyme recognition site III and ribozyme recognition site IV are only formed inside the coding region contained in the coding element.

The nucleotide sequence of the truncated fragment I of the coding element and the nucleotide sequence of the truncated fragment II of the coding element of the present disclosure are formed by truncation of the coding element sequence, with the former one corresponding to a partial sequence close to the 5' direction in the coding element sequence and the latter one corresponding to a remaining partial sequence close to the 3' direction in the coding element sequence. Moreover, the ribozyme recognition site I and ribozyme recognition site II are located inside any coding region contained in the coding element.

Alternatively, the nucleotide sequence of the truncated fragment III of the coding element and the nucleotide sequence of the truncated fragment IV of the coding element herein are formed by truncation of the coding element sequence, with the former one corresponding to a partial sequence close to the 5' direction in the coding element sequence and the latter one corresponding to a remaining partial sequence close to the 3' direction in the coding element sequence. Moreover, the ribozyme recognition site III and ribozyme recognition site IV are located inside any coding region contained in the coding element.

Furthermore, in the case that two or more coding regions are contained in the coding element, the two adjacent coding regions may be linked by a linker or a translation initiation element. Accordingly, a linker linking to adjacent coding region sequences, or a translation initiation element linking to adjacent coding region sequence, is further contained inside at least one of the truncated fragments of coding element.

Illustratively, the coding element consists of one coding region 1 that contains a ribozyme recognition site. Accordingly, the truncated fragment I of the coding element is a truncated fragment I of the coding region 1, and the truncated fragment II of the coding element is a truncated fragment II of coding region 1. Alternatively, the truncated fragment III of the coding element is a truncated fragment III of the coding region 1, and the truncated fragment IV of the coding element is a truncated fragment IV of the coding region 1.

Illustratively, the coding element includes a coding region 1 and a coding region 2 sequentially arranged in the 5' to 3' direction, and a ribozyme recognition site is provided inside the coding region 1. The coding region 1 is truncated to obtain a truncated fragment I of the coding element and a truncated fragment II of the coding element, or to obtain a truncated fragment III of the coding element and a truncated fragment IV of the coding element. Wherein, the truncated fragment I of the coding element is a truncated fragment I of the coding region 1, and the truncated fragment II of the coding element includes a truncated fragment II of the coding region 1, and the coding region 2. Alternatively, the truncated fragment III of the coding element is a truncated fragment III of the coding region 1, and the truncated fragment IV of the coding element includes a truncated fragment IV of the coding region 1, and the coding region 2.

In some alternative embodiments, the truncated fragment II of the coding element further includes a linker located between the truncated fragment II of the coding region 1, and the coding region 2. Alternatively, the truncated fragment IV of the coding element further includes a linker located between truncated fragment IV of the coding region 1 and coding region 2.

Illustratively, the coding element includes a coding region 3 and a coding region 1 sequentially arranged in the 5' to 3' direction, and a ribozyme recognition site is provided inside the coding region 1. The coding region 1 is truncated to obtain a truncated fragment I of the coding element and a truncated fragment II of the coding element, or to obtain a truncated fragment III of the coding element and a truncated fragment IV of the coding element. The truncated fragment I of the coding element includes the coding region 3 and a truncated fragment I of the coding region 1, and the truncated fragment II of the coding element is a truncated fragment II of the coding region 1. Alternatively, the truncated fragment III of the coding element includes the coding region 3 and a truncated fragment III of the coding region 1, and the truncated fragment IV of the coding element is a truncated fragment IV of the coding region 1.

In some alternative embodiments, the truncated fragment of the coding element further includes a linker located between the coding region 3 and the truncated fragment I of the coding region 1. Alternatively, the truncated fragment III of the coding element further includes a linker located between the coding region 3 and the truncated fragment III of the coding region 1.

As an example, the coding element includes a coding region 3, a coding region 1 and a coding region 2 sequentially arranged in the 5' to 3' direction, and a ribozyme recognition site is provided inside the coding region 1. The coding region 1 is truncated to obtain a truncated fragment I of the coding element and a truncated fragment II of the coding element, or to obtain a truncated fragment III of the coding element and a truncated fragment IV of the coding element. The truncated fragment I of the coding element includes the coding region 3 and a truncated fragment I of the coding region 1, and the truncated fragment II of the coding element includes a truncated fragment II of the coding region 1 and the coding region 2. Alternatively, the truncated fragment III of the coding element includes the coding region 3 and a truncated fragment III of the coding region 1, and the truncated fragment IV of the coding element includes a truncated fragment IV of coding region 1, and the coding region 2.

In some alternative embodiments, the truncated fragment I of the coding element further includes a linker located between the coding region 3 and the truncated fragment I of the coding region 1. Alternatively, the truncated fragment III of the coding element further includes a linker located between the coding region 3 and the truncated fragment III of the coding region 1. In some alternative embodiments, the truncated fragment II of the coding element further includes a linker located between the truncated fragment II of the coding region 1, and the coding region 2. Alternatively, the truncated fragment IV of the coding element further includes a linker located between the truncated fragment IV of the coding region 1 and the coding region 2.

Illustratively, the coding element includes a coding region 1, a translation initiation element and a coding region 4 sequentially arranged in the 5' to 3' direction, and a ribozyme recognition site is provided inside the coding region 1. The coding region 1 is truncated to obtain a truncated fragment I of the coding element and a truncated fragment II of the coding element, or to obtain a truncated fragment III of the coding element and a truncated fragment IV of the coding element. The truncated fragment I of the coding element includes a truncated fragment I of the coding region 1, and the truncated fragment II of the coding element includes a truncated fragment II of the coding region 1, the translation initiation element, and the coding region 4. The truncated fragment III of the coding element includes a truncated fragment III of the coding region 1, and the truncated fragment IV of the coding element includes a truncated fragment IV of the coding region 1, the translation initiation element, and the coding region 4.

Illustratively, the coding element includes a coding region 4, a translation initiation element and a coding region 1 sequentially arranged in the 5' to 3' direction, and a ribozyme recognition site is provided inside the coding region 1. The coding region 1 is truncated to obtain a truncated fragment I of the coding element and a truncated fragment II of the coding element, or to obtain a truncated fragment III of the coding element and a truncated fragment IV of the coding element. The truncated fragment I of the coding element includes the coding region 4, the translation initiation element and a truncated fragment I of the coding region 1, and the truncated fragment II of the coding element is a truncated fragment II of the coding region 1. The truncated fragment III of the coding element includes the coding region 4, the translation initiation element and a truncated fragment III of the coding region 1, and the truncated fragment IV of the coding element is a truncated fragment IV of the coding region 1.

It should be noted that the number of the coding regions 2, 3 or 4 may be one, or two or more, which is not exhaustive herein.

The term "expression" includes any step involving production of polypeptides, including but not limited to transcription, post-transcriptional modification, translation, post-translational modification, and secretion.

The term "antibody", as used herein in the broadest sense thereof, refers to a protein containing antigen-binding sites, encompassing natural antibodies and artificial antibodies with various structures, including but not limited to polyclonal, monoclonal, monospecific, multi specific, nonspecific, humanized, single-stranded, chimeric, synthetic, recombinant, hybrid, mutated, and grafted antibodies. The term "antibody" further includes an antibody fragment, such as Fab, F(ab')$_2$, FV, scFv, Fd, dAb and another antibody fragment that retains antigen-binding capacity. In general, such fragment may include an antigen-binding fragment.

As used herein, the term "hybridization" refers to a process in which a base on one nucleic acid chain is combined with a complementary base on another nucleic acid chain by base-pairing. The hybridization reaction may be selective, allowing for selection of a specific target sequence even at low concentrations from a sample. The stringency of hybridization conditions (such as highly stringent, moderately stringent, and stringent conditions) may be adjusted by, for example, a concentration of a salt or formamide in a pre-hybridized solution and a hybridized solution, or a hybridization temperature, and the like. As an example, the stringency may be increased by decreasing the salt concentration, increasing the formamide concentration, or increasing the hybridization temperature. Generally, the stringent conditions include hybridization in at least about 0% to at least about 15% v/v formamide and at least about 1 M to at least about 2 M salt at a temperature of about 25° C. to about 42° C., and washing in at least about 1 M to at least about 2 M salt. The moderately stringent conditions include hybridization in at least about 16% to at least about 30% v/v formamide and at least about 0.5 M to at least about 0.9 M salt at a temperature of about 25° C. to about 65° C., and washing in at least about 0.5 M to at least about 0.9 M salt. The highly stringent conditions include hybridization in at least about 31% to at least about 50% v/v formamide and at least about 0.01 M to at least about 0.15 M salt at a temperature of at least about 65° C., and washing in at least about 0.01 M to at least about 0.15 M salt. The formamide is optional in these hybridization conditions. Other suitable hybridization buffers and conditions are well known to those skilled in the art and are described, for example, in Sambrook et al., Molecular Cloning: A Laboratory Manual, 2nd ed. Cold Spring Harbor Press, Plainview, N.Y. (1989); and Ausubel et al., Short Protocols in Molecular Biology, 4$^{th}$ ed., John Wiley & Sons (1999).

The term "pharmaceutically acceptable carrier" used in the context herein refers to auxiliary materials widely used in the field of pharmaceutical production. The carriers are used mainly to provide a pharmaceutical composition with use safety, stable properties and/or specific functions, and also to provide a method that allows active ingredients of a drug to be dissolved at a desired rate after being administered to a subject, or promotes effective absorption of the active ingredients in a subject administrated with the drug. A pharmaceutically acceptable carrier may be an inert filler, or a functional ingredient that provides a function for a pharmaceutical composition (such as stabilizing overall pH value of the composition or preventing degradation of active ingredients in the composition). Non-limiting examples of the pharmaceutically acceptable carriers include, but are not limited to, an adhesive, a suspending agent, an emulsifier, a diluent (or a filler), a granulating agent, a tackifier, a disintegrating agent, a lubricant, an anti-adhesion agent, a glidant, a wetting agent, a gelling agent, an absorption retarder, a dissolution inhibitor, an enhancer, an adsorbent, a buffer, a chelating agent, a preservative, a coloring agent, a flavoring agent, a sweetener, and the like.

As used herein, the term "complementary" or "hybridized" is intended to refer to a "polynucleotide" and "oligonucleotide" related to a base-pairing rule (interchangeable terms and refers to a nucleotide sequence). For example, the sequence "CAGT" is complementary to the sequence "GTCA". The complementation or hybridization may be "partial" or "complete". A "partial" complementation or hybridization means that one or more nucleic acid bases are mispaired according to a base-pairing rule, and a "total" or "complete" complementation or hybridization between nucleic acids means that each nucleic acid base is paired with another base by base-pairing. The degree of complementarity or hybridization of a nucleic acid chain has an important influence on hybridization efficiency and intensity of such nucleic acid chain. This is particularly important in an amplification reaction and a detection method depending on binding between nucleic acids.

The term "recombinant nucleic acid molecule" refers to a polynucleotide with sequences that are not ligated together in nature. The recombinant polynucleotide may be contained in a suitable vector, through which the recombinant polynucleotide may be delivered to a suitable host cell. Then the polynucleotide is expressed in the recombinant host cell to produce, for example, a "recombinant polypeptide", a "recombinant protein", a "fusion protein", or the like.

The term "recombinant expression vector" refers to a DNA structure that expresses, for example, a polynucleotide encoding a desired polypeptide. The recombinant expression vector may include, for example, i) a genetic element set involved in regulating gene expression, such as a promoter and an enhancer; ii) a structure or coding sequence for transcribing into mRNA and translating into a protein; and iii) a transcription subunit for appropriate transcription and translation of initiation and termination sequences. The recombinant expression vector is constructed in any suitable way. The nature of the vector is not critical, and any vector may be used, including a plasmid, a virus, a phage, and a transposon. A possible vector used for the present disclosure includes, but is not limited to, a chromosomal, a non-chromosomal and a synthetic DNA sequence, such as a viral plasmid, a bacterial plasmid, a phage DNA, a yeast plasmid, and a vector derived from combination of a plasmid and a phage DNA, and a DNA from a virus such as lentivirus, retrovirus, vaccinia, adenovirus, fowlpox, baculovirus, SV40 and pseudorabies.

The term "host cell" refers to a cell into which an exogenous polynucleotide has been introduced, including progenies of such cells. The host cell includes a "transformant" and a "transformed cell", including a primary transformed cell and a progeny derived therefrom. The host cell may be any type of cell system used to generate an antibody of the present disclosure, including an eukaryotic cell, such as a mammalian cell, an insect cell, and a yeast cell, and a prokaryotic cell, such as a *Escherichia coli* cell. The host cell includes a cultured cell, and also includes a cell in a transgenic animal, a transgenic plant or a cultured plant tissue or an animal tissue. The term "recombinant host cell" covers a host cell that is different from a parent cell after introduction of a recombinant nucleic acid molecule, a recombinant expression vector and a circular RNA, and the recombinant host cell is specifically produced by transformation. The host cells of the present disclosure may be a prokaryotic cell or an eukaryotic cell, as long as it may be used to introduce a recombinant nucleic acid molecule, a recombinant expression vector, a circular RNAs, and the like of the present disclosure.

As used herein, the term "individual", "patient" or "subject" includes a mammal. The mammal includes, but is not limited to, a domestic animal (for example, cattle, sheep, cats, dogs, and horses), a primate (for example, human and non-human primates, such as monkeys), a rabbit, and a rodent (for example, mice and rats).

As used herein, the terms "transformation", "transfection" and "transduction" have the meaning commonly understood by those skilled in the art, that is, a process introducing exogenous DNA into a host. The transformation, transfection and transduction methods include any method for introducing a nucleic acid into a cell, including but not limited to, electroporation, calcium phosphate ($CaPO_4$) precipitation, calcium chloride ($CaCl_2$) precipitation, microinjection, polyethylene glycol (PEG)-based method, DEAE-dextran-based method, cationic liposome-based method, and lithium acetate-DMOS-based method.

As used herein, the "treatment" refers to alleviation of symptoms of a disease by contact (e.g., administration) of a circular RNA, a circularization precursor RNA, a composition, and the like of the present disclosure to a subject suffering from such disease, as compared to the scenario without such contact, and does not necessarily mean that the symptoms of the disease must be completely suppressed. Suffering from a disease means that some symptoms of disease occurred in a body.

As used herein, the "prevention" refers to alleviation of symptoms of a disease by contact (e.g., administration) of a circular RNA, a circularization precursor RNA, a composition, and the like of the present disclosure to a subject before suffering from such disease, as compared to the scenario without such contact, and does not necessarily mean that the symptoms of the disease must be completely suppressed.

As used herein, the term "effective amount" refers to such an amount or a dose of a recombinant nucleic acid molecule, a recombinant expression vector, a circularization precursor RNA, a circular RNA, a vaccine, or a composition of the present disclosure, that produces an expected effect in a patient in need of treatment or prevention after being administered in a single dose or in multiple doses. The effective amount may be easily determined by an attending physician as a skilled person in the art by considering the following factors: for example, species such as mammals; size, age and general health thereof; a related specific disease; a degree or severity of the disease; a response of an individual; a specific antibody administered; an administration mode; bioavailability characteristics of the administered preparation; a selected dosage regimen; and an application of any concomitant therapy.

As used herein, the term "individual", "patient" or "subject" includes a mammal. The mammal includes, but is not limited to, a domestic animal (for example, cattle, sheep, cats, dogs, and horses), a primate (for example, human and non-human primates, such as monkeys), a rabbit, and a rodent (for example, mice and rats).

Unless defined otherwise or clearly indicated in the context, all technical and scientific terms used herein have the same meaning as those commonly understood by a person of ordinary skill in the art to which the present disclosure belongs.

Clean PIE System

A process in which a classic PIE system is ligated to form a circular RNA is shown in FIGS. 5A through 5D, where the linear RNA includes the following elements ligated sequentially: a 3' intron, a second exon E2 (Exon2), an exogenous fragment, a first exon E1 (Exon1), and a 5' intron. With GTP and $Mg^{2+}$ presenting in the environment, GTP attacks a linking position between the E1 and the 5' intron, resulting in cleavage of a 5' splice site (5ss) and release of the 5' intron. The 3-OH end of E1 then attacks a linking position between the 3' intron and the E2, resulting in cleavage of a 3' splice site (3ss) and release of the 3' intron. Finally, they are ligated to form a target circular RNA.

However, using a classic PIE system may lead to presence of additional exon sequences of E1 and E2 in the circular RNA, and reduced sequence accuracy of the circular RNAs, resulting in an increase of natural immunogenicity of the circular RNA, and susceptibility to degradation in cells.

To solve the problems above, the present disclosure provides a Clean PIE system with a novel structure, which may be used to prepare a circular RNA through self-splicing of the PIE system without changing a protein expression sequence, exhibiting high circularization efficiency. In addition, there is no need to introduce additional E1 and E2 sequences into the circularized circular RNA, which not only simplifies the structure of the circular RNA and reduces various potential safety hazards, but also improves the sequence accuracy of the circular RNA, reduces natural immunogenicity of the circular RNA, and improves stability thereof in cells, thus making it suitable for clinical application fields, such as serving as a gene therapy vector, an expressing therapeutic protein, serving as a nucleic acid vaccine and the like, showing broad application prospects.

The Clean PIE system of the present disclosure includes, but is not limited to, a DNA construct used to prepare a circular RNA, a recombinant expression vector containing the DNA construct, a circularization precursor RNA molecule obtained by in vitro transcription by using the recombinant expression vector, and the like.

In some embodiments, the present disclosure provides a recombinant nucleic acid molecule for preparing a circular RNA. Illustratively, the recombinant nucleic acid molecule may be the above-mentioned DNA construct for preparing a circular RNA, a circularization precursor RNA molecule, and the like.

Figure 1:
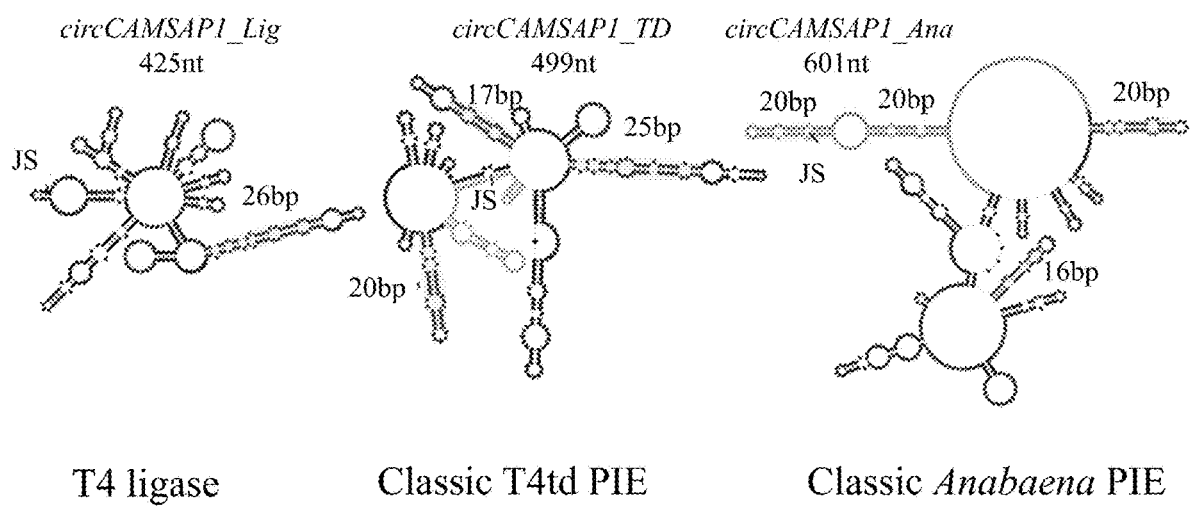
FIG. 1 shows a schematic diagram of secondary structures of circular RNAs ligated and formed with T4 ligase, T4 td PIE system, and *Anabaena* PIE system respectively, in the cited reference [14].
Figure 2A:
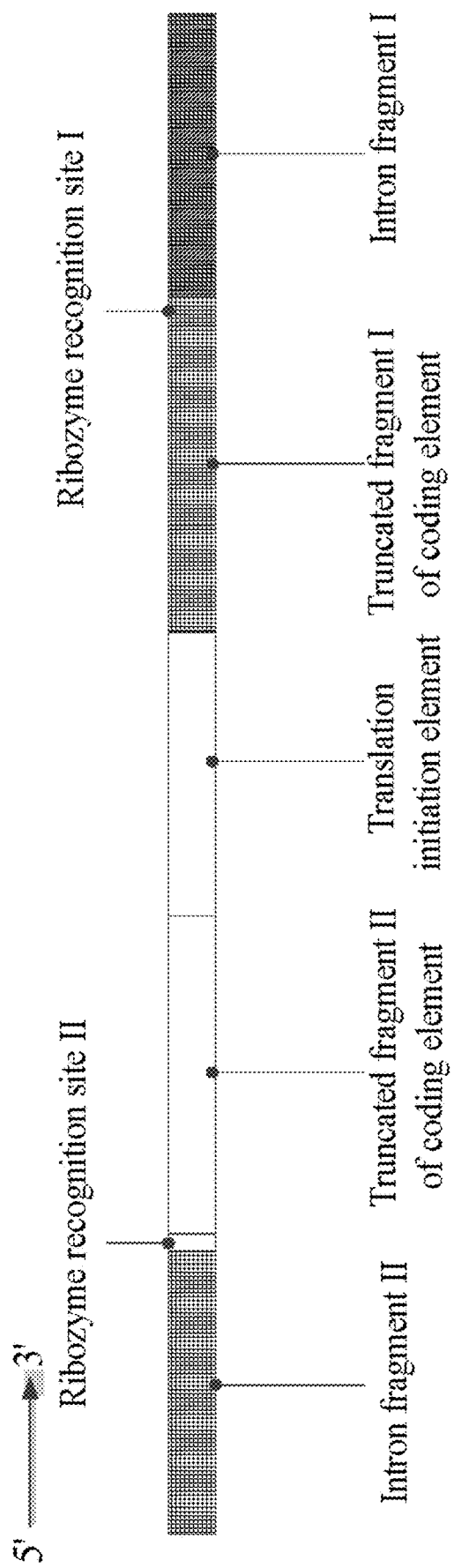
FIGS. 2A through 2C show schematic structural diagrams of a recombinant nucleic acid molecule for preparing a circRNA according to the present disclosure (a Clean PIE system).

In some embodiments, the structure of the recombinant nucleic acid molecule, as shown in FIG. 2A, includes elements arranged in the following order in the 5' to 3' direction: an intron fragment II, a truncated fragment II of a coding element, a translation initiation element, a truncated fragment I of a coding element, and an intron fragment I.

The 3' end of the truncated fragment I of the coding element includes a ribozyme recognition site I that consists of a first predetermined number of nucleotides located at the 3' end of the truncated fragment I of the coding element; the 5' end of the truncated fragment II of the coding element contains a ribozyme recognition site II that consists of a second predetermined number of nucleotides located at the 5' end of the truncated fragment II of the coding element.

The nucleotide sequence of the truncated fragment I of the coding element and the nucleotide sequence of the truncated fragment II of the coding element are used to form a coding element sequence encoding at least one target polypeptide in the 5' to 3' direction. The nucleotide sequence of the truncated fragment I of the coding element corresponds to a partial sequence close to the 5' direction in the coding element sequence, and the nucleotide sequence of the truncated fragment II of the coding element corresponds to a remaining partial sequence close to the 3' direction in the coding element sequence.

It should be noted that the coding element is formed in the circular RNA prepared from the recombinant nucleic acid molecule. In addition, the coding element includes one or two or more coding regions encoding a target polypeptide. In the presence of two or more coding regions in the coding element, the coding element may also includes a linker located between two adjacent coding regions, a translation initiation element between two adjacent coding regions, or other types of sequences desired.

The nucleotide sequence of the intron fragment I and the nucleotide sequence of the intron fragment II are used to form an intron sequence in the 5' to 3' direction. The nucleotide sequence of the intron fragment I includes a partial sequence close to the 5' direction in the intron sequence, and the nucleotide sequence of the intron fragment II includes a remaining sequence close to the 3' direction in the intron sequence.

In other words, the nucleotide sequence of the truncated fragment I of the coding element and the nucleotide sequence of the truncated fragment II of the coding element may be ligated to form a coding element sequence encoding at least one target polypeptide, and the nucleotide sequence of the intron fragment I and the nucleotide sequence of the intron fragment II may be ligated to form an intron sequence. In preparing the circular RNAs by the recombinant nucleic acid molecule with the above structure, cleavage occurs at a linking position between a ribozyme recognition site I and the intron fragment I, releasing the intron fragment I. After that, cleavage occurs at a linking position of a ribozyme recognition site II and the intron fragment II, releasing the intron fragment II. The 3' end of truncated fragment I of the coding element is ligated to the 5' end of truncated fragment II of coding element to form a circular molecule. In the present disclosure, without changing the target polypeptide sequence encoded by the coding element and introducing additional E1 and E2 sequences, the circular RNA encoding the target protein is obtained by self-splicing, with a high sequence accuracy, stability, and low immunogenicity.

Figure 2B:
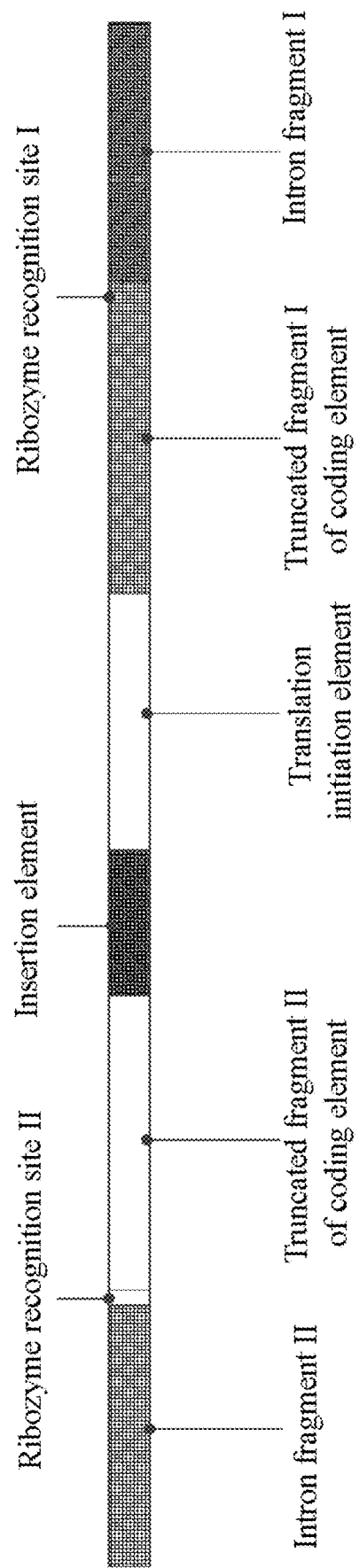
Figure 2C:
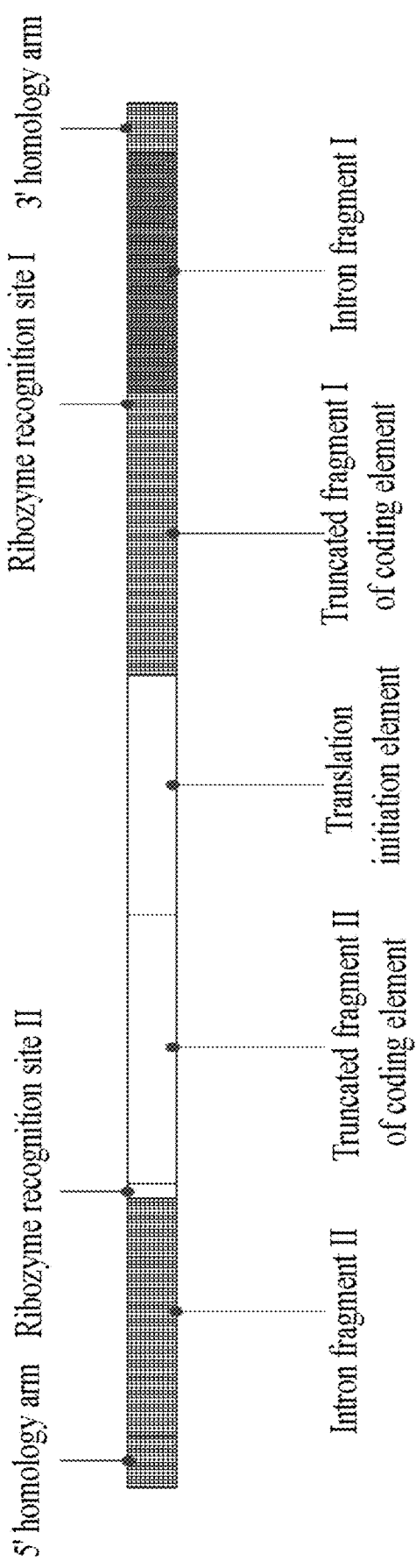
Figure 2D:
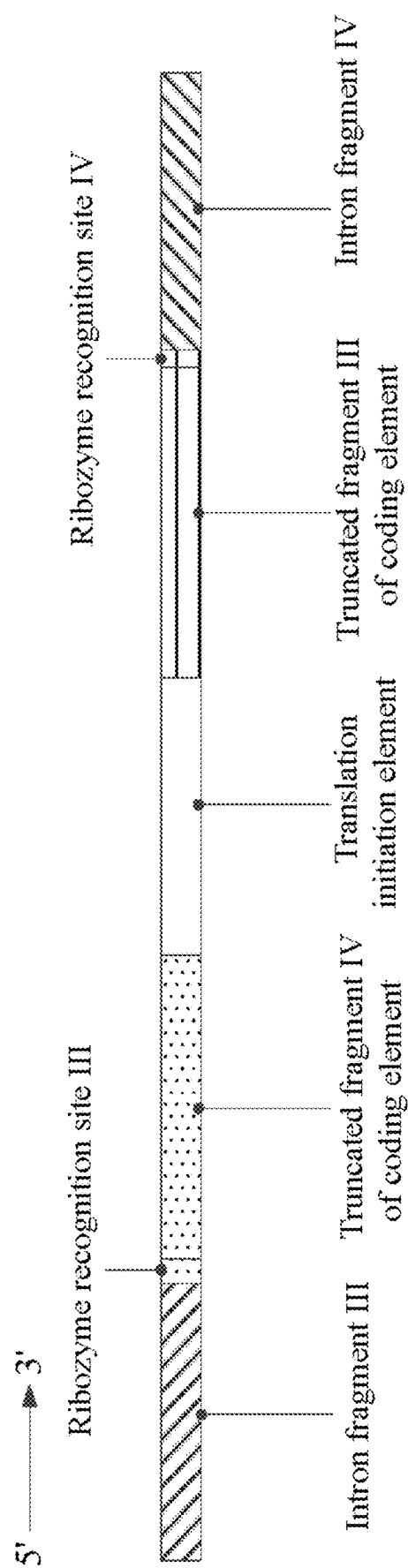
FIGS. 2D through 2F show schematic structural diagrams of a recombinant nucleic acid molecule for preparing a circRNA according to the present disclosure (a Clean PIE system).

In other embodiments, a recombinant nucleic acid molecule, as shown in FIG. 2D, includes elements arranged in the following order in the 5' to 3' direction: an intron fragment III, a truncated fragment IV of a coding element, a translation initiation element, a truncated fragment III of a coding element, and an intron fragment IV.

The 3' end of the truncated fragment III of the coding element includes a ribozyme recognition site IV that consists of a second predetermined number of nucleotides located at the 3' end of the truncated fragment III of coding element. The 5' end of the truncated fragment IV of the coding element contains a ribozyme recognition site III that consists of a first predetermined number of nucleotides located at the 5' end of the truncated fragment IV of the coding element.

The nucleotide sequence of the truncated fragment III of the coding element and the nucleotide sequence of the truncated fragment IV of the coding element are used to form a coding element sequence encoding at least one target polypeptide in the 5' to 3' direction. The nucleotide sequence of the truncated fragment III of the coding element corresponds to a partial sequence close to the 5' direction in the coding element sequence, and the nucleotide sequence of the truncated fragment IV of the coding element corresponds to a remaining partial sequence close to the 3' direction in the coding element sequence. The sequence of the intron fragment III is a reverse sequence or a reverse complementary sequence of the nucleotide sequence of the intron fragment I, and the sequence of intron fragment IV is a reverse sequence or a reverse complementary sequence of the nucleotide sequence of the intron fragment II. The sequence of the ribozyme recognition site III is a reverse sequence of the nucleotide sequence of the ribozyme recognition site I, and the sequence of the ribozyme recognition site IV is a reverse sequence of the nucleotide sequence of the ribozyme recognition site II.

As discovered by the present disclosure, the reverse sequence or reverse complementary sequence of intron sequence may also construct the Clean PIE system. In the present disclosure, the reverse sequence or reverse complementary sequence of a 5' portion of the intron is used as the intron fragment III, and the reverse sequence or reverse complementary sequence of a 3' portion of the intron is used as the intron fragment IV. The intron fragment III is ligated to the 5' end of the truncated fragment IV of the coding element, corresponding to the intron fragment III, the first predetermined number of nucleotides at the 5' end of truncated fragment IV of the coding element constitute the ribozyme recognition site III, and the sequence of the ribozyme recognition site III is a reverse sequence or reverse complementary sequence of the nucleotide sequence of the ribozyme recognition site I. The intron fragment IV is ligated to the 3' end of truncated fragment III of the coding element, corresponding to the intron fragment IV, the second predetermined number of nucleotides at the 3' end of truncated fragment III of the coding element constitute the ribozyme recognition site IV, and the sequence of the ribozyme recognition site IV is a reverse sequence or reverse complementary sequence of the nucleotide sequence of the ribozyme recognition site II.

In preparation of a circular RNA in vitro by the recombinant nucleic acid molecule containing the above elements, cleavage successively occurs at the ribozyme recognition site III and the ribozyme recognition site IV, releasing the intron fragment III and the intron fragment IV, and the 3' end of the truncated fragment III of coding element is ligated to the 5' end of the truncated fragment IV of the coding element to form the circular RNA molecule. As the ribozyme recognition site III and the ribozyme recognition site IV are provided inside the truncated fragments of the coding element, no additional E1 and E2 sequences are introduced into the circular RNA after in vitro circularization, providing advantages of accurate sequence, simple structure, low immunogenicity, and the like, enabling large-scale in vitro production with the application advantages in the fields of nucleic acid vaccines, expression of therapeutic proteins, clinical immunotherapy, and the like.

Translation Initiation Element

In the present disclosure, a translation initiation element may be any type of element that is able to initiate translation of a target polypeptide. In some embodiments, the translation initiation element is an element containing any one or more of the following sequences: an IRES sequence, a 5'UTR sequence, a Kozak sequence, a sequence with $m^6A$ modification (N (6) methyladenosine modification), and a complementary sequence of ribosome 18S rRNA. In other embodiments, the translation initiation element may be any other type of cap-independent translation elements.

In some embodiments, the translation initiation element is an IRES element derived from those including, but not limited to, viruses, mammals, fruit flies, and the like. In some alternative embodiments, the IRES element is derived from a virus. Illustratively, the IRES element contains an IRES sequence derived from a small RNA virus. Furthermore, the IRES element includes, but is not limited to, an IRES sequence derived from Echovirus, Human poliovirus, Human Enterovirus, Coxsackievirus, Human rhinovirus, Canine picornavirus, Turdivirus 3, Hepatovirus, Passerivirus, Picornaviridae, Tremovirus A, Feline kobuvirus, Murine kobuvirus, Kobuvirus sewage Kathmandu, Ferret kobuvirus, Marmot kobuvirus, Human parechovirus, Chicken picornavirus, Falcon picornavirus, Feline picornavirus, French Guiana picornavirus, and the like.

In some alternative embodiments, the recombinant nucleic acid molecule provided by the present disclosure consists of elements arranged in the following order in the 5' to 3' direction: an intron fragment II, a truncated fragment II of a coding element, a translation initiation element, a truncated fragment I of a coding element, and an intron fragment I. In other alternative embodiments, the recombinant nucleic acid molecule may also include any other one or more of the above elements, such as a transcriptional regulatory element for regulating transcription level, a translational regulatory element for regulating translation level, a purification element for purifying circular RNA, and the like.

In some alternative embodiments, the recombinant nucleic acid molecule provided by the present disclosure consists of elements arranged in the following order in the 5' to 3' direction: an intron fragment III, a truncated fragment IV of a coding element, a translation initiation element, a truncated fragment III of a coding element, and an intron fragment IV. In other alternative embodiments, the recombinant nucleic acid molecule may also include any other one or more of the above elements, such as a transcriptional regulatory element for regulating transcription level, a translational regulatory element for regulating translation level, a purification element for purifying circular RNA, and the like.

Intron Fragment

An intron fragment in the present disclosure is derived from Group I intron with ribozyme activity of self-splicing reaction and is widely found in various species. Illustratively, Group I introns include, but are not limited to, phage T4 td gene, *Anabaena* tRNA$^{Leu}$, TpaCOX2, and Ptu, and the like.

In some embodiments, an intron fragment I and an intron fragment II are derived from the Group I intron, and contain a partial sequence close to the 5' direction and another partial sequence close to the 3' direction, respectively, both of which constitute the Group I intron. A ribozyme recognition site I is derived from an exon sequence (Exon 1, E1) ligated to the 5' end of the Group I intron, and a ribozyme recognition site II is derived from an exon sequence (Exon 2, E2) ligated to the 3' end of Group I intron. The intron fragment I is ligated to the ribozyme recognition site I, and the intron fragment II is ligated to the ribozyme recognition site II, thus forming a PIE system capable of self-splicing.

In other embodiments, an intron fragment III and an intron fragment IV are derived from the Group I intron, and contain a reverse sequence of the partial sequence close to the 5' direction and a reverse sequence of another partial sequence close to the 3' direction, respectively, both of which constitute the Group I intron. A ribozyme recognition site III is derived from a reverse sequence of the exon sequence (Exon 1, E1) ligated to the 5' end of the Group I intron, and a ribozyme recognition site IV is derived from a reverse sequence of the exon sequence (Exon 2, E2) ligated to the 3' end of the Group I intron. The intron fragment III is ligated to the ribozyme recognition site III, and the intron fragment IV is ligated to the ribozyme recognition site IV, thus forming a PIE system capable of self-splicing.

In some alternative embodiments, the ribozyme recognition site I consists of 3 to 100 nucleotides, preferably 3 to 50 nucleotides, and more preferably 3 to 10 nucleotides. That is, the first predetermined number of nucleotides located at the 3' end of truncated fragment I of the coding element is 3 to 100 nucleotides, preferably 3 to 50 nucleotides, and more preferably 3 to nucleotides. Illustratively, the first predetermined number is 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, and any integer value between any two of them.

In some alternative embodiments, the ribozyme recognition site II consists of 1 to 100 nucleotides, preferably 1 to 50 nucleotides, and more preferably 1 to 10 nucleotides. That is, the second predetermined number of nucleotides located at the 5' end of truncated fragment II of the coding element is 1 to 100 nucleotides, preferably 1 to 50 nucleotides, and more preferably 1 to 10 nucleotides. Illustratively, the first predetermined number is 1, 2, 3, 4, 5, 6, 7, 8, 9, 10, 15, 20, 25, 30, 35, 40, 45, 50, 55, 60, 65, 70, 75, 80, 85, 90, 95, 100, and any integer value between any two of them.

In some alternative embodiments, the ribozyme recognition site III consists of 3 to 100 nucleotides, preferably 3 to 50 nucleotides, and more preferably 3 to 10 nucleotides. That is, the first predetermined number of nucleotides located at the 5' end of truncated fragment IV of the coding element is 3 to 100 nucleotides, preferably 3 to 50 nucleotides, and more preferably 3 to 10 nucleotides. Illustratively, the first predetermined number is 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, and any integer value between any two of them.

In some alternative embodiments, the ribozyme recognition site IV consists of 1 to 100 nucleotides, preferably 1 to 50 nucleotides, more preferably 1 to 10 nucleotides. That is, the second predetermined number of nucleotides located at the 3' end of truncated fragment III of coding element is 1 to 100 nucleotides, preferably 1 to 50 nucleotides, and more preferably 1 to nucleotides. Illustratively, the first predetermined number is 1, 2, 3, 4, 5, 6, 7, 8, 9, 10, 15, 20, 25, 30, 35, 40, 45, 50, 55, 60, 65, 70, 75, 80, 85, 90, 95, 100, and any integer value between any two of them.

In some preferred embodiments, a sum of the first predetermined number and the second predetermined number is not equal to 3y, where y≥1 and y is an integer. That is, the sum of the first predetermined number and the second predetermined number is not equal to an integer multiple of 3. When the sum is not a value of an integer multiple of 3, increased freedom of arranging a ribozyme recognition site in the coding fragment may be obtained, resulting in effective circularization for the circular RNA.

Figure 13:
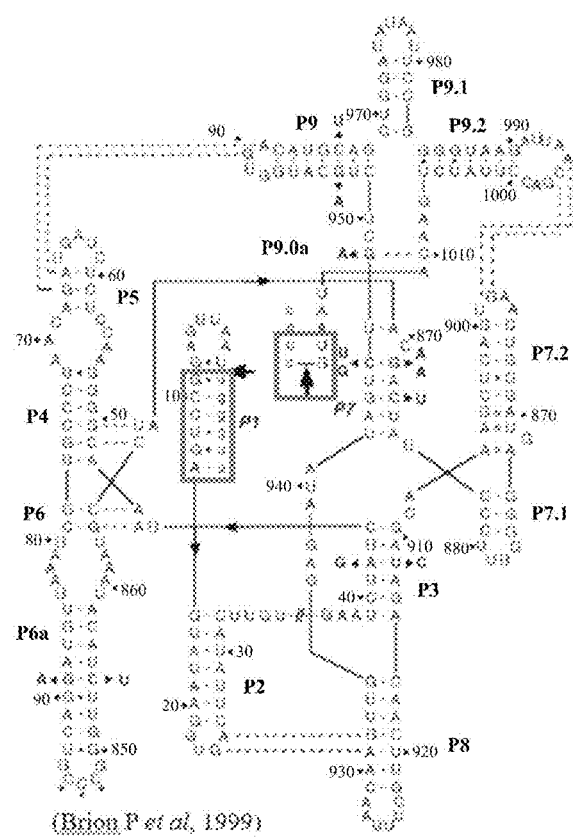
FIG. 13 shows a prognostic diagram of a secondary structure derived from a T4td intron.

In some alternative embodiments, the Group I intron is a T4 td intron derived from a T4 phage td gene, with a secondary structure shown in FIG. 13. The nucleotide sequence of the ribozyme recognition site used for circularization in the T4 td intron is "5'-TTGGG<u>T</u>CT-3'", where the circularization position is located between T and C. Therefore, the nucleotide sequence of the ribozyme recognition site I is "5'-TTGGG<u>T</u>-3'", and the nucleotide sequence of the ribozyme recognition site II is "5'-<u>C</u>T-3'". Alternatively, the nucleotide sequence of the ribozyme recognition site III is "5'-TGGGTT-3'", and the nucleotide sequence of the ribozyme recognition site IV is "5'-TC-3'". Alternatively, the nucleotide sequence of the ribozyme recognition site III is "5'-ACCCAA-3'", and the nucleotide sequence of the ribozyme recognition site IV is "5'-AG-3'".

It should be noted that the ribozyme recognition site with a few base mutations may also be used for in vitro circularization of a circular RNA, under conditions that keep the bases at the circularization position unchanged. Illustratively, the present disclosure has found that the ribozyme recognition site and ligated intron fragments thereof may remain the circularization activity, in the presence of one or more of the following mutations in "5'-TTGGG<u>T</u>CT-3'": base T to C mutation at position 2, base G to A mutation at position 3, and base T to A mutation at position 8.

In some alternative embodiments, the nucleotide sequence of the intron fragment I derived from the T4 td intron is shown in SEQ ID NO: 7, or is at least 80%, 81%, 82%, 83%, 84%, 85%, 86%, 87%, 88%, 89%, 90%, 91%, 92%, 93%, 94%, 95%, 96%, 97%, 98%, 99% identical to that shown in SEQ ID NO: 7.

In some alternative embodiments, the nucleotide sequence of the intron fragment II derived from the T4 td intron is shown in SEQ ID NO: 6, or is at least 80%, 81%, 82%, 83%, 84%, 85%, 86%, 87%, 88%, 89%, 90%, 91%, 92%, 93%, 94%, 95%, 96%, 97%, 98%, 99% identical to that shown in SEQ ID NO: 6.

Figure 14:
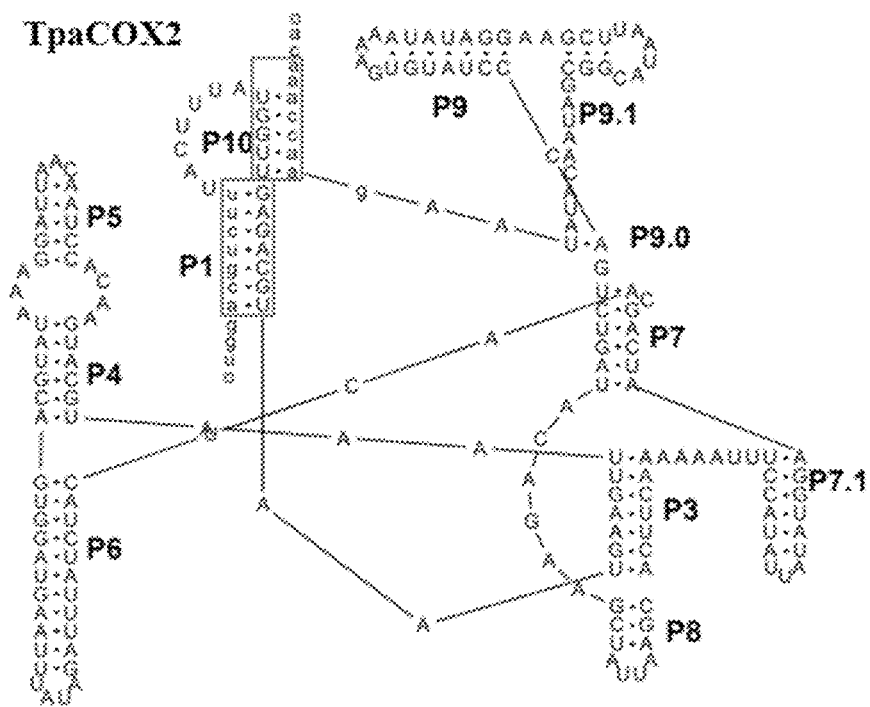
FIG. 14 shows a prognostic diagram of a secondary structure derived from a TpaCOX2 intron.

In some alternative embodiments, the Group I intron is a TpaCOX2 intron, which is an intron sequence of a cytochrome xoidase cox2 gene of a *T. papilionaceus* mitochondria, with a secondary structure as shown in FIG. 14. The nucleotide sequence of the ribozyme recognition site used for circularization in the TpaCOX2 intron is "5'-ACGTCTTAACCAA-3'" (SEQ ID NO: 80), where the circularization position is located between T and C. Therefore, the nucleotide sequence of the ribozyme recognition site I is "5'-ACGTCTT-3'", and the nucleotide sequence of the ribozyme recognition site II is "5'-AACCAA-3'". Alternatively, the nucleotide sequence of the ribozyme recognition site III is "5'-TTCTGCA-3'", and the nucleotide sequence of the ribozyme recognition site IV is "5'-AAC-CAA-3'". Alternatively, the nucleotide sequence of the ribozyme recognition site III is "5'-AAGACGT-3'", and the nucleotide sequence of the ribozyme recognition site IV is "5'-TTGGTT-3'".

Figure 15:
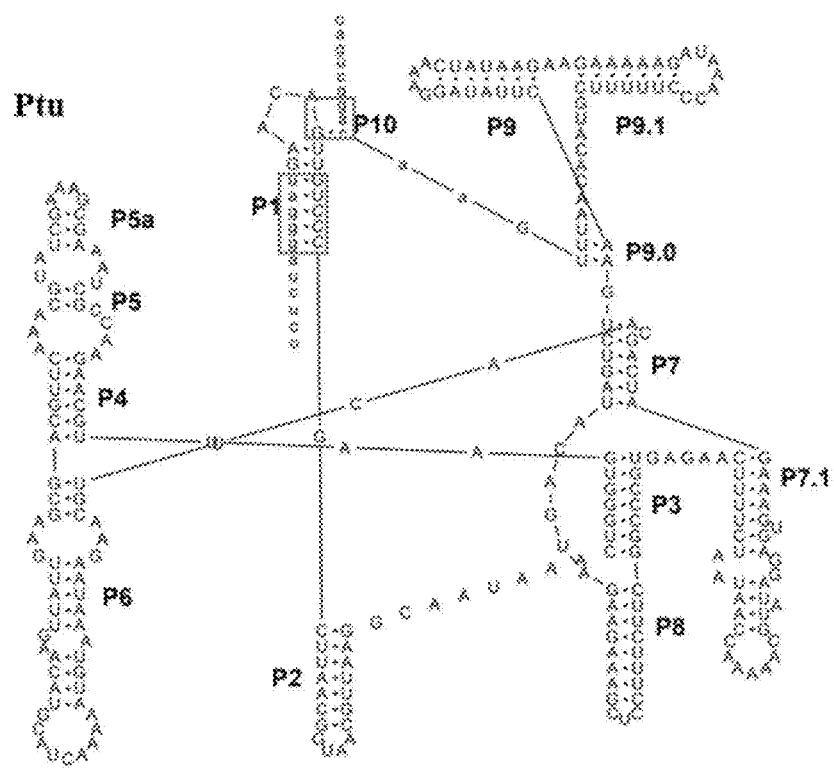
FIG. 15 shows a prognostic diagram of a secondary structure derived from a Ptu intron.

In some alternative embodiments, the Group I intron is a Ptu intron, with a secondary structure shown in FIG. 15. The Ptu is a precursor RNA of a chloroplast ribosomal large subunit RNA (rrnL) in *Pedinomonas tuberculata*, which is a green algae in *Pseudomonas*. The nucleotide sequence of the ribozyme recognition site used for circularization in the Ptu intron is "5'-AGGGATCA-3'", where the circularization position is located between T and C. Therefore, the nucleotide sequence of the ribozyme recognition site I is "5'-AGGGAT-3'", and the nucleotide sequence of the ribozyme recognition site II is "5'-CA-3'". Alternatively, the nucleotide sequence of the ribozyme recognition site III is "5'-TAGGGA-3'", and the nucleotide sequence of the ribozyme recognition site IV is "5'-AC-3'". Alternatively, the nucleotide sequence of the ribozyme recognition site III is "5'-ATCCCT-3'", and the nucleotide sequence of the ribozyme recognition site IV is "5'-TG-3'".

It should be noted that the sequences of the ribozyme recognition sites and the intron fragments are not limited in the present disclosure, as long as they are derived from the Group I introns, efficient for circularization, and may be used to prepare a circular RNA in vitro.

Recombinant Nucleic Acid Molecule Containing Insertion Element

Figure 2E:
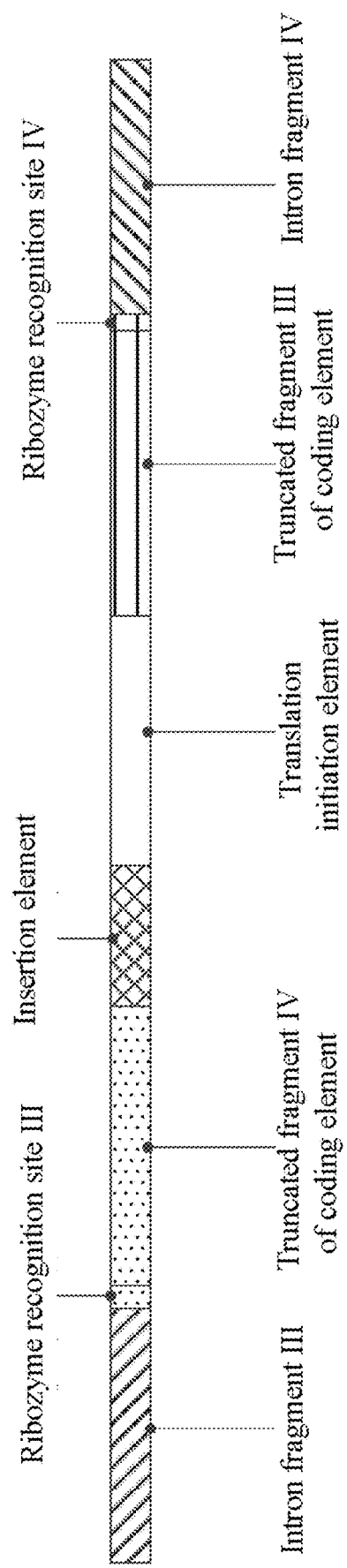

In some embodiments, a recombinant nucleic acid molecule includes an insertion element, which may be used to regulate transcription of the recombinant nucleic acid molecule, regulate translation of a circular RNA, enable specific expression of a circular RNA between different tissues, or purify a circular RNA, and the like. Illustratively, as shown FIG. 2B, the insertion element is located between a truncated fragment II of a coding element and a translation initiation element. Alternatively, as shown in FIG. 2E, the insertion element is located between a truncated fragment IV of a coding element and a translation initiation element. Specifically, the insertion element is ligated to the 5' end of the translation initiation element.

In some embodiments, the insertion element is at least one selected from the group consisting of (i) to (iii): (i) a transcriptional regulatory element, (ii) a translational regulatory element, and (iii) a purification element. Illustratively, the insertion element includes one of or a combination of any two or more of the following sequences: an untranslated region (UTR) sequence, a polyN sequence, an aptamer sequence, a riboswitch sequence, and a transcriptional regulator-binding sequence. In the polyN sequence, N is selected from at least one of A, T, G, and C.

In some alternative embodiments, the translational regulatory element includes an untranslated region sequence, which may serve to regulate stability, immunogenicity, and efficiency of the circular RNA in expressing the target polypeptide, and the like. The untranslated region sequence is not specifically limited in the present disclosure, which may be selected from any type of sequences known in the art having the properties of regulating the circular RNA transcription, translation, intracellular stability, immunogenicity, and the like. Furthermore, the untranslated region sequence is also not limited to the 5'UTR sequence or the 3'UTR sequence.

In some alternative embodiments, the untranslated region sequence contains one or more (for example, 1, 2, 3, 4, 5, 6, and 7) miRNA recognition sequences. The addition of one or more miRNA recognition sequences may provide specific expression of a circular RNA in different tissues and cells, providing targeted delivery of a circular RNA molecule.

In some alternative embodiments, the translational regulatory element contains a polyN sequence, where N may be at least one of A, T, G, and C. The addition of the translation regulatory element containing the polyN sequence may improve efficiency of target polypeptide expression of the circular RNA, immunogenicity, and stability of the circular RNA, or purify the circular RNA. The length of polyN sequence, as well as the selected N type and the manner of composition in the polyN sequence, is not specifically limited in the present disclosure, as long as they facilitate the improvement of the properties of the circular RNA. Illustratively, polyN sequences are polyA sequence, polyAC sequence, and the like.

In some alternative embodiments, the translational regulatory element contains a riboswitch sequence. The riboswitch sequence is a class of untranslated sequences capable of regulating the transcription and translation of RNA. The riboswitch sequence in the present disclosure may affect expression of the circular RNA, including but not limited to transcription termination, inhibition of translation initiation, mRNA self-cleavage, and changes of splicing pathway in eukaryotes. In addition, the riboswitch sequence may also control the expression of circular RNA by triggering binding or removing of molecules. Illustratively, riboswitch sequences are cobalamin riboswitch (also called $B_{12}$-element), FMN riboswitch (also called RFN element), glmS riboswitch, SAM riboswitch, SAH riboswitch, tetrahydrofolate riboswitch, Moco riboswitch, and the like, and the type and sequence of riboswitch sequence are not limited in the present disclosure, as long as they can realize regulation of the transcriptional and translational levels of circular RNAs expressing target polypeptides.

In some alternative embodiments, the translational regulatory element contains an aptamer sequence. In the present disclosure, the aptamer sequence may be used to regulate transcription and translation of circular RNAs, or to purify and prepare a circular RNA in vitro. In an exemplary embodiment, the aptamer sequence is the sequence as shown in SEQ ID NO: 37, or is at least 80%, 81%, 82%, 83%, 84%, 85%, 86%, 87%, 88%, 89%, 90%, 91%, 92%, 93%, 94%, 95%, 96%, 97%, 98%, 99% identical to that shown in SEQ ID NO: 37.

Recombinant Nucleic Acid Molecule Containing Homology Arm

In some embodiments, a recombinant nucleic acid molecule contains a homology arm. Specifically, the homology arm includes a 5' homology arm located at the 5' end of the recombinant nucleic acid molecule and a 3' homology arm located at the 3' end of the recombinant nucleic acid molecule, and the nucleic acid sequence of the 5' homology arm hybridizes with the nucleotide sequence of the 3' homology arm.

In some embodiments, in the recombinant nucleic acid molecule, the 5' homology arm is ligated to the 5' end of an intron fragment II, and the 3' homology arm is ligated to the 3' end of an intron fragment I, as shown in FIG. 2C. The hybridization between the sequence of 5' homology arm with that of 3' homology arm, allows intron fragment I and intron fragment II to be close to each other, and after the cleavage at a linking position between a ribozyme recognition site I and the intron fragment I, it is favorable for 3'-OH at ribozyme recognition site I to further attack a phosphodiester bond linking ribozyme recognition site II and intron fragment II, thereby releasing intron fragment II.

Figure 2F:
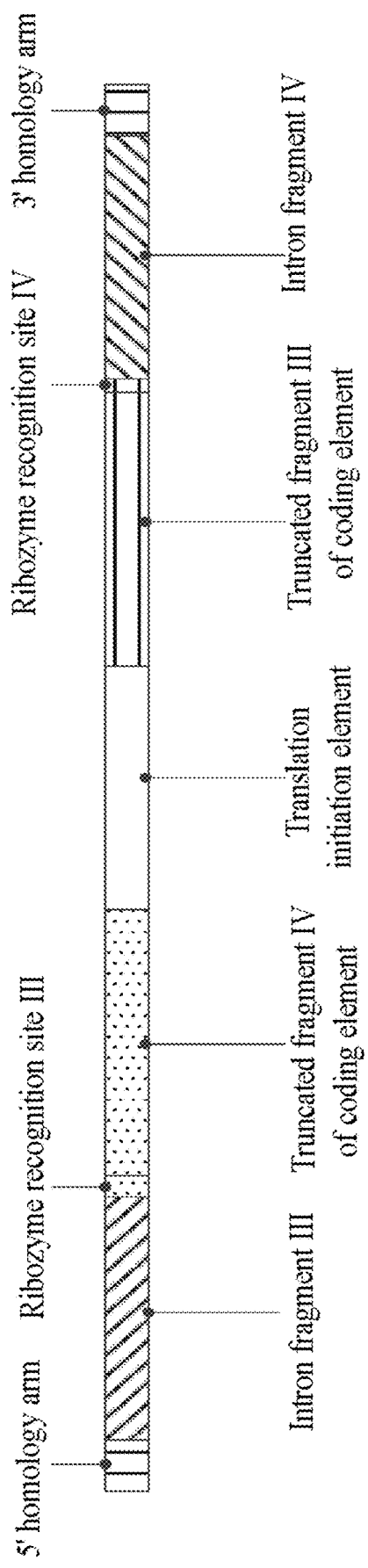

In some embodiments, in the recombinant nucleic acid molecule, the 5' homology arm is ligated to the 5' end of the intron fragment III, and the 3' homology arm is ligated to the 3' end of the intron fragment IV, as shown in FIG. 2F. The hybridization between the sequence of 5' homology arm with that of 3' homology arm, allows the intron fragment III and the intron fragment IV to be close to each other, after the cleavage at a linking position between a ribozyme recognition site III and the intron fragment III, it is favorable for 3'-OH at ribozyme recognition site III to further attack a phosphodiester bond linking ribozyme recognition site IV and intron fragment IV, thereby releasing intron fragment IV.

In some embodiments of the present disclosure, by comparing the effects on in vitro circularization of the circular RNA when the homology arm is added or not added. it is discovered in the present disclosure that effective circularization rate may still be remained for the recombinant nucleic acid molecule without the homology arm added, as compared to recombinant nucleic acid molecule with the homology arm added. Therefore, in order to further simplify structure of the recombinant nucleic acid molecule, in some embodiments, the 5' homology arm and the 3' homology arm are not contained in the recombinant nucleic acid molecule. This is because within the frame of the present disclosure, the circularization site (ribozyme recognition site) always separates the coding gene into two parts, for which typically no complicated secondary structure exists in the coding region. Such benign sequence separates a promoter element from a self-splicing intron sequence, thus forming a unique secondary structure, which is more conducive to correct folding and approaching of the intron sequences. As a result, an effective circularization may be achieved without the homology arm within the frame of the present disclosure.

Target Polypeptide

The type of target polypeptide is not limited in the present disclosure, which may be a human-derived protein or a non-human protein. Illustratively, a target polypeptide include, but are not limited to, an antigen, an antibody, an antigen-binding fragment, a fluorescent protein, a protein with therapeutic activity against diseases, and a protein with gene-editing activity.

The term "antibody", as used herein in the broadest sense thereof, refers to a protein containing an antigen-binding site, which encompasses natural antibodies and artificial antibodies with various structures, including but not limited to monoclonal antibodies, polyclonal antibodies, multi specific antibodies (for example, bispecific antibodies), single-stranded antibodies, complete antibodies, and antibody fragments.

The term "antigen-binding fragment" herein is a portion or a fragment of a intact or complete antibody with fewer amino acid residues than the intact or complete antibody, and is is capable of binding to an antigen or competing with the intact antibody (that is, the intact antibody from which the antigen-binding fragment is derived) for binding the antigen. An antigen-binding fragment of an antibody may be produced by recombinant DNA technology or by enzymatic or chemical cleavage of an intact antibody. The antigen-binding fragment includes, but is not limited to, Fv, Fab, Fab', Fab'-SH, F(ab')$_2$, a diabody, a linear antibody, a single chain antibody (e.g., ScFv), a single domain antibody, a bivalent or bispecific antibody or a fragment thereof; Camelidae antibody (a heavy chain antibody); and a bispecific antibody or polyspecific antibody formed by antibody fragments.

In the present disclosure, a protein with therapeutic activity against diseases may include, but is not limited to, an enzyme replacement protein, a protein for supplementation, a protein vaccine, an antigen (e.g. a tumor antigen, a virus, bacteria), a hormone, a cytokine, an antibody, an immunotherapy (e.g., a cancer), a cell reprogramming/transdifferentiation factor, a transcription factor, a chimeric antigen receptor, a transposase or nuclease, an immune effector (e.g., having effects on susceptibility to immune response/signal), a regulated death effector protein (e.g., an inducer of apoptosis or necrosis), an insoluble inhibitor of a tumor (e.g., a cancer protein inhibitor), an epigenetic modifier, an epigenetic enzyme, a transcription factor, a DNA or protein-modifying enzyme, a DNA intercalator, an efflux pump inhibitor, a nuclear receptor activator or inhibitor, a proteasome inhibitor, an enzyme competition inhibitor, a protein synthesis effector or inhibitor, a nuclease, a protein fragment or domain, a ligand or receptor, and the CRISPR system or a component thereof, and the like.

Coding Element for Forming One or More Coding Regions

In some embodiments, the recombinant nucleic acid molecule is used for preparing a circular RNA containing a coding element, where the coding element in the circular RNA includes a coding region 1, optionally (a) at least one coding region 2, and optionally (b) at least one coding region 3.

Figure 3A:
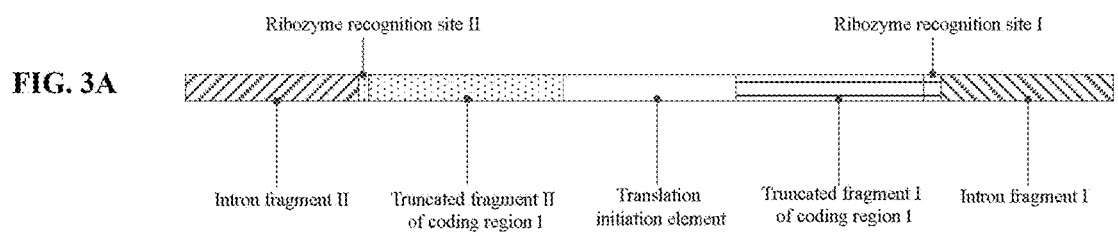
FIGS. 3A and 3B show a schematic structural diagram of a recombinant nucleic acid molecule for preparing a circRNA according to the present disclosure (a Clean PIE system).

In the present disclosure, a truncated fragment I of the coding element and a truncated fragment II of the coding element in the recombinant nucleic acid molecule form the coding region 1, optionally (a) the at least one coding region 2, and optionally (b) the at least one coding region 3. Illustratively, in some embodiments, the truncated fragment I of the coding element and the truncated fragment II of the coding element form the coding region 1, as shown in FIG. 3A. Accordingly, the truncated fragment I of the coding element is a truncated fragment I of the coding element 1, the truncated fragment II of the coding element is a truncated fragment II of the coding region 1. Therefore, the 3' end of truncated fragment I of the coding region 1 contains a ribozyme recognition site I that consists of a first predetermined number of nucleotides located at the 3' end of the truncated fragment I of the coding region 1; and the 5' end of the truncated fragment II of the coding region 1 contains a ribozyme recognition site II that consists of a second predetermined number of nucleotides located at the 5' end of the truncated fragment II of coding region 1. The truncated fragment I of the coding element and the truncated fragment II of the coding element in the recombinant nucleic acid molecule are used to form the coding region 1, to express a target polypeptide in vitro or in vivo.

In other embodiments, the truncated fragment I of the coding element and the truncated fragment II of the coding element in the recombinant nucleic acid molecule are used to form a coding region 1 and at least one coding region 2. The circular RNA prepared by the recombinant nucleic acid molecule may provide tandem expression of at least two target polypeptides. Illustratively, the recombinant nucleic acid molecule contains elements arranged in the following order: (i) an intron fragment II, a truncated fragment II of the coding region 1, the at least one coding region 2, a translation initiation element, a truncated fragment I of the coding region 1, and an intron fragment I, as shown in FIG. 4A to 4B.

Figure 4A:
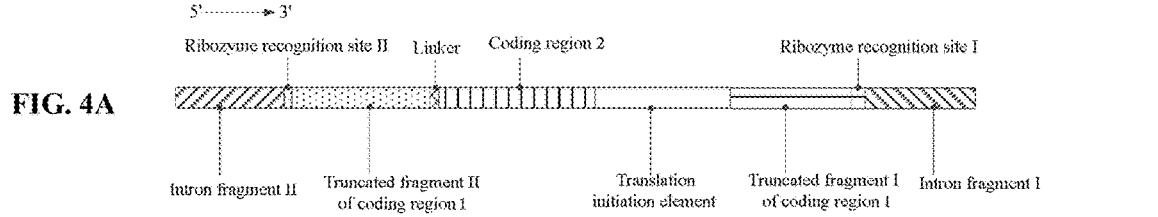
FIGS. 4A through 4D show schematic structural diagrams of a recombinant nucleic acid molecule for preparing a circRNA according to the present disclosure (a Clean PIE system).

In some alternative embodiments, the coding regions 2 has a quantity of one, and the recombinant nucleic acid molecule contains elements arranged in the following order: an intron fragment II, a truncated fragment II of the coding region 1, the coding region 2, a translation initiation element, a truncated fragment I of the coding region 1, and an intron fragment I, as shown in FIG. 4A. In other alternative embodiments, the recombinant nucleic acid molecule consists of the elements arranged in the above order.

Figure 4B:
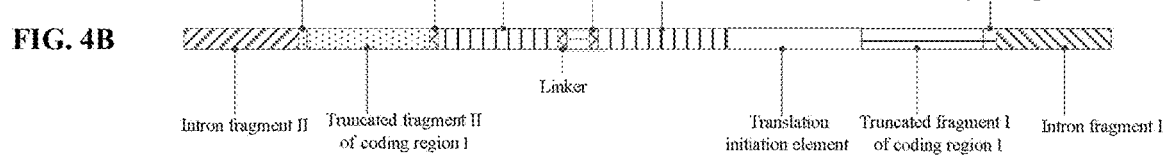

In some alternative embodiments, the coding regions 2 has a quantity of at least two, and the recombinant nucleic acid molecule includes elements arranged in the following order: an intron fragment II, a truncated fragment II of the coding region 1, the at least two coding regions 2, a translation initiation element, a truncated fragment I of the coding region 1, and an intron fragment I, as shown in FIG. 4B. In other alternative embodiments, the recombinant nucleic acid molecule consists of the elements arranged in the above order.

In some preferred embodiments, the recombinant nucleic acid molecule further includes a linker located between the truncated fragment II of the coding region 1 and the coding region 2, and/or a linker located between any two adjacent coding regions 2. Such linkers are used to separate the coding region 2 from the coding region 1, and separate any two adjacent coding regions 2 from each other, allowing the circular RNA prepared by the recombinant nucleic acid molecule to express two or more target polypeptides.

In other embodiments, the truncated fragment I of the coding element and the truncated fragment II of the coding element in the recombinant nucleic acid molecule are used to form a coding region 1 and at least one coding region 3. The circular RNA prepared by the recombinant nucleic acid molecule may provide tandem expression of at least two target polypeptides. Illustratively, the recombinant nucleic acid molecule includes elements arranged in the following order: (ii) an intron fragment II, a truncated fragment II of the coding region 1, a translation initiation element, the at least one coding region 3, a truncated fragment I of the coding region 1, and an intron fragment I, as shown in FIG. 5A to 5B.

In some alternative embodiments, the coding regions 3 has a quantity of one, and the recombinant nucleic acid molecule includes elements arranged in the following order: an intron fragment II, a truncated fragment II of the coding region 1, a translation initiation element, the coding region 3, a truncated fragment I of the coding region 1, and an intron fragment I, as shown in FIG. 5A. In other alternative embodiments, the recombinant nucleic acid molecule consists of the elements arranged in the above order.

In some alternative embodiments, the coding regions 3 has a quantity of at least two, and the recombinant nucleic acid molecule includes elements arranged in the following order: an intron fragment II, a truncated fragment II of the coding region 1, a translation initiation element, the at least two coding regions 3, a truncated fragment I of the coding region 1, and an intron fragment I, as shown in FIG. 5B. In other alternative embodiments, the recombinant nucleic acid molecule consists of the elements arranged in the above order.

In some preferred embodiments, the recombinant nucleic acid molecule further includes a linker located between the truncated fragment I of the coding region 1 and the coding region 3, and/or a linker located between any two adjacent coding regions 3. Such linkers are used to separate the coding region 3 from the coding region 1, and separate any two adjacent coding regions 3 from each other, allowing the circular RNA prepared by the recombinant nucleic acid molecule to express two or more target polypeptides.

In other embodiments, the truncated fragment I of the coding element and the truncated fragment II of the coding element in the recombinant nucleic acid molecule are used to form a coding region 1, at least one coding region 2, and at least one coding region 3. The circular RNA prepared by the recombinant nucleic acid molecule may provide tandem expression of at least three target polypeptides. Illustratively, the recombinant nucleic acid molecule includes elements arranged in the following order: (iii) an intron fragment II, a truncated fragment II of the coding region 1, the at least one coding region 2, a translation initiation element, the at least one coding region 3, a truncated fragment I of the coding region 1, and an intron fragment I, as shown in FIGS. 6A to 6B.

In some alternative embodiments, the coding region 2 and the coding region 3 has a quantity of one respectively, and the recombinant nucleic acid molecule includes elements arranged in the following order: an intron fragment II, a truncated fragment II of the coding region 1, the coding region 2, a translation initiation element, the coding region 3, a truncated fragment I of the coding region 1, and an intron fragment I, as shown in FIG. 6A. In other alternative embodiments, the recombinant nucleic acid molecule consists of the elements arranged in the above order.

In some alternative embodiments, the coding region 2 has a quantity of at least two, and the coding region 3 has a quantity of at least two. The recombinant nucleic acid molecule includes elements arranged in the following order: an intron fragment II, a truncated fragment II of the coding region 1, the at least two coding regions 2, a translation initiation element, the at least two coding regions 3, a truncated fragment I of the coding region 1, and an intron fragment I, as shown in FIG. 6B. In other alternative embodiments, the recombinant nucleic acid molecule consists of the elements arranged in the above order.

In some preferred embodiments, the recombinant nucleic acid molecule further includes a linker located between the truncated fragment II of the coding region 1 and the coding region 2, a linker located between the truncated fragment I of the coding region 1 and the coding region 3, a linker located between any two adjacent coding regions 2, and/or a linker located between any two adjacent coding regions 3. Such linkers are used to separate the coding region 2 from the coding region 1, the coding region 3 from the coding region 1, any two adjacent coding regions 2 from each other, and any two adjacent coding regions 3 from each other, allowing the circular RNA prepared by the recombinant nucleic acid molecule to express three or more target polypeptides.

Figure 3B:
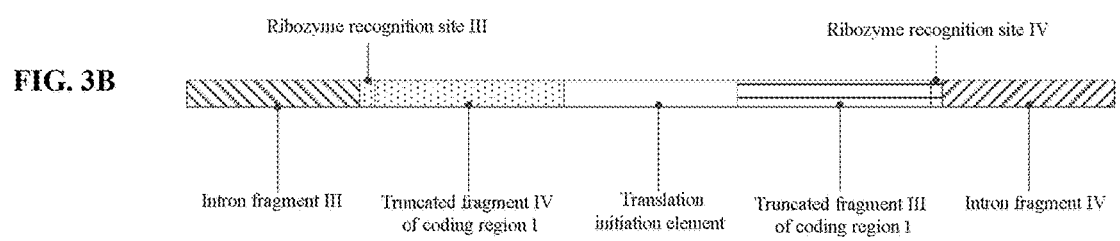

In some embodiments, a truncated fragment III of the coding element and a truncated fragment IV of the coding element are used to form a coding region 1. Accordingly, the truncated fragment III of the coding element is the truncated fragment III of the coding region 1, and the truncated fragment IV of the coding element is the truncated fragment IV of the coding region 1, as shown in FIG. 3B. Therefore, the 3' end of truncated fragment III of the coding region 1 contains a ribozyme recognition site IV that consists of a first predetermined number of nucleotides located at the 3' end of the truncated fragment III of the coding region 1; and the 5' end of the truncated fragment IV of the coding region 1 contains a ribozyme recognition site III that consists of a second predetermined number of nucleotides located at the 5' end of the truncated fragment IV of coding region 1. The truncated fragment III of the coding element and the truncated fragment IV of the coding element in the recombinant nucleic acid molecule are used to form the coding region 1, to express a target polypeptide in vitro or in vivo.

In other embodiments, the truncated fragment III of the coding element and the truncated fragment IV of the coding element in the recombinant nucleic acid molecule are used to form a coding region 1 and at least one coding region 2. The circular RNA prepared by the recombinant nucleic acid molecule may provide tandem expression of at least two target polypeptides. Illustratively, the recombinant nucleic acid molecule includes elements arranged in the following order: (v) an intron fragment III, the truncated fragment IV of the coding region 1, the at least one coding region 2, a translation initiation element, the truncated fragment III of the coding region 1, and an intron fragment IV, as shown in FIG. 4C to 4D.

Figure 4C:
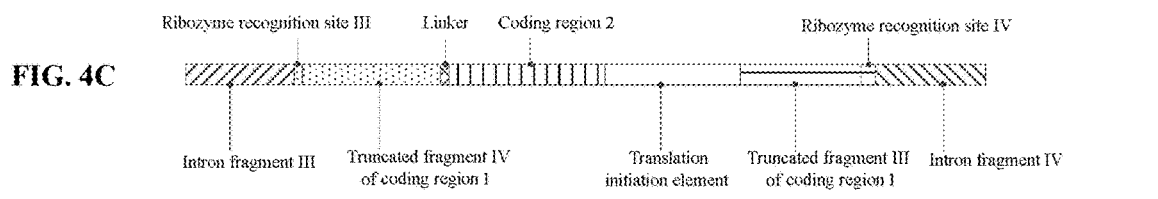

In some alternative embodiments, the coding fragment 2 has a quantity of one, and the recombinant nucleic acid molecule includes elements arranged in the following order: an intron fragment III, the truncated fragment IV of the coding region 1, the coding region 2, a translation initiation element, the truncated fragment III of the coding region 1, and an intron fragment IV, as shown in FIG. 4C. In other alternative embodiments, the recombinant nucleic acid molecule consists of the elements arranged in the above order.

Figure 4D:
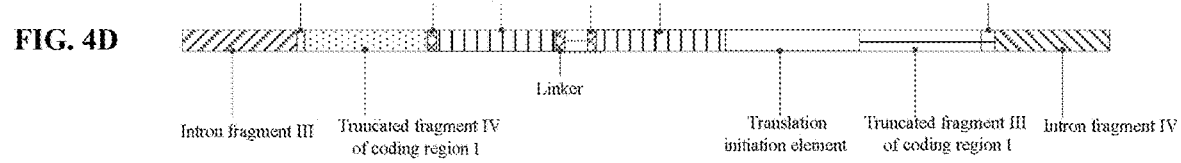

In some alternative embodiments, the coding region 2 has a quantity of at least two, and the recombinant nucleic acid molecule includes elements arranged in the following order: an intron fragment III, the truncated fragment IV of the coding region 1, the at least two coding regions 2, a translation initiation element, the truncated fragment III of the coding region 1, and an intron fragment IV, as shown in FIG. 4D. In other alternative embodiments, the recombinant nucleic acid molecule consists of the elements arranged in the above order.

In some preferred embodiments, the recombinant nucleic acid molecule further includes a linker located between the truncated fragment IV of the coding region 1, and the coding region 2, and/or a linker located between any two adjacent coding regions 2. Such linkers are used to separate the coding region 2 from the coding region 1, and any two adjacent coding regions 2 from each other, allowing the circular RNA prepared by the recombinant nucleic acid molecule to express two or more target polypeptides.

In other embodiments, the truncated fragment III of the coding element and the truncated fragment IV of the coding element in the recombinant nucleic acid molecule are used to form a coding region 1 and at least one coding region 3. The circular RNA prepared by the recombinant nucleic acid molecule may provide tandem expression of at least two target polypeptides. Illustratively, the recombinant nucleic acid molecule includes elements arranged in the following order: (vi) an intron fragment III, the truncated fragment IV of the coding region 1, a translation initiation element, the at least one coding region 3, the truncated fragment III of the coding region 1, and an intron fragment IV, as shown in FIG. 5C to 5D.

In some alternative embodiments, the coding region 3 has a quantity of one, and the recombinant nucleic acid molecule includes elements arranged in the following order: an intron fragment III, the truncated fragment IV of the coding region 1, a translation initiation element, the coding region 3, the truncated fragment III of the coding region 1, and an intron fragment IV, as shown in FIG. 5C. In other alternative embodiments, the recombinant nucleic acid molecule consists of the elements arranged in the above order.

In some alternative embodiments, the coding region 3 has a quantity of at least two, and the recombinant nucleic acid molecule includes elements arranged in the following order: an intron fragment III, the truncated fragment IV of the coding region 1, a translation initiation element, the at least two coding regions 3, the truncated fragment III of the coding region 1, and an intron fragment IV, as shown in FIG. 5D. In other alternative embodiments, the recombinant nucleic acid molecule consists of the elements arranged in the above order.

In some preferred embodiments, the recombinant nucleic acid molecule further includes a linker located between the truncated fragment III of the coding region 1 and the coding region 3, and/or a linker located between any two adjacent coding regions 3. Such linkers are used to separate the coding region 3 from the coding region 1, and any two adjacent coding regions 3 from each other, allowing the circular RNA prepared by the recombinant nucleic acid molecule to express two or more target polypeptides.

In other embodiments, the truncated fragment III of the coding element and the truncated fragment IV of the coding element in the recombinant nucleic acid molecule are used to form a coding region 1, at least one coding region 2, and at least one coding region 3. The circular RNA prepared by the recombinant nucleic acid molecule may provide tandem expression of at least three target polypeptides. Illustratively, the recombinant nucleic acid molecule includes elements arranged in the following order: (vii) an intron fragment III, the truncated fragment IV of the coding region 1, the at least one coding region 2, a translation initiation element, the at least one coding region 3, the truncated fragment III of the coding region 1, and an intron fragment IV, as shown in FIG. 6C to 6D.

In some alternative embodiments, the coding region 2 has a quantity of one, and the coding region 3 has a quantity of one. The recombinant nucleic acid molecule includes elements arranged in the following order: an intron fragment III, the truncated fragment IV of the coding region 1, the coding region 2, a translation initiation element, the coding region 3, the truncated fragment III of the coding region 1, and an intron fragment IV, as shown in FIG. 6C. In other alternative embodiments, the recombinant nucleic acid molecule consists of the elements arranged in the above order.

In some alternative embodiments, the coding regions 2 has a quantity of at least two, and the coding region 3 has a quantity of at least two. The recombinant nucleic acid molecule includes elements arranged in the following order: an intron fragment III, the truncated fragment IV of the coding region 1, the at least two coding regions 2, a translation initiation element, the at least two coding regions 3, the truncated fragment III of the coding region 1, and an intron fragment IV, as shown in FIG. 6D. In other alternative embodiments, the recombinant nucleic acid molecule consists of the elements arranged in the above order.

In some preferred embodiments, the recombinant nucleic acid molecule further includes a linker located between the truncated fragment IV of the coding region 1, and the coding region 2, a linker located between the truncated fragment III of the coding region 1 and the coding region 3, a linker located between any two adjacent coding regions 2, and/or a linker located between any two adjacent coding regions 3. Such linkers are used to separate the coding region 2 from the coding region 1, the coding region 3 from the coding region 1, any two adjacent coding regions 2 from each other, and any two adjacent coding regions 3 from each other, enabling the circular RNA prepared by the recombinant nucleic acid molecule to express two or more target polypeptides.

In the present disclosure, the linker may be a polynucleotide encoding 2A peptide, or another type of polynucleotide encoding a linker peptide for spacing target polypeptides, where the 2A peptide is a short peptide (about 18 to 25 amino acids in length) derived from a virus, commonly known as a "self-splicing" peptide, enabling a strand of transcript to produce a variety of proteins. Illustratively, 2A peptides are P2A, T2A, E2A, F2A, and the like.

In the present disclosure, the coding region 1, each coding region 2 and each coding region 3 encode any type of target polypeptide independently of one another. The target polypeptides encoded by the coding region 1 and any one coding region 2 may be the same or different, the target polypeptide encoded by the coding region 1 and any one coding region 3 may be the same or different, the target polypeptide encoded by any two coding regions 2 may be the same or different, the target polypeptide encoded by any two coding regions 3 may be the same or different, and the target polypeptide encoded by any one coding region 2 and any one coding region 3 may be the same or different.

In the present disclosure, the coding regions located at different positions are distinguished by numbering the coding regions (for example, coding region 1, coding region 2, coding region 3, and the like). Illustratively, the coding region 1 represents a coding region containing a ribozyme recognition site; the coding region 2 represents a coding region between the truncated fragment II of the coding region 1 and the translation initiation element, or the coding region 2 represents a coding region between the truncated fragment IV of the coding region 1 and the translation initiation element; the code region 3 represents a coding region between the truncated fragment I of the coding region 1 and the translation initiation element, or the coding region 2 represents a coding region between the truncated fragment III of the coding region 1 and the translation initiation element.

Recombinant Nucleic Acid Molecule Including at Least Two Translation Initiation Elements In some embodiments, the recombinant nucleic acid molecule is used for preparing a circular RNA containing a coding element; where the coding element in the circular RNA contains a coding region 1, at least one coding region 4, and a translation initiation element located between any two adjacent coding regions.

In some embodiments, a truncated fragment I of the coding element and a truncated fragment II of the coding element in the recombinant nucleic acid molecule form the coding region 1, the at least one coding region 4, and the translation initiation element located between any two adjacent coding regions. The 3' end of the truncated fragment I of the coding element contains a ribozyme recognition site I that consists of a first predetermined number of nucleotides located at the 3' end of the truncated fragment I of the coding region 1; and the 5' end of the truncated fragment II of the coding element contains a ribozyme recognition site II that consists of a second predetermined number of nucleotides located at the 5' end of the truncated fragment II of the coding region 1. In the circular RNA prepared by the recombinant nucleic acid molecule in vitro, each coding region corresponds to one translation initiation element, allowing for tandem expression of at least two target polypeptides.

Figure 7A:
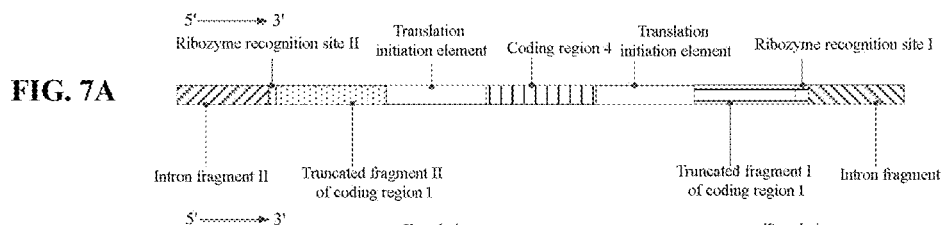
FIGS. 7A through 7C shows a schematic structural diagram of a recombinant nucleic acid molecule for preparing a circRNA according to the present disclosure (a Clean PIE system).

In some alternative embodiments, the coding region 4 has a quantity of one, and the recombinant nucleic acid molecule includes elements arranged in the following order: an intron fragment II, the truncated fragment II of the coding region 1, a translation initiation element, the coding region 4, a translation initiation element, the truncated fragment I of the coding region 1, and an intron fragment I, as shown in FIG. 7A. In other embodiments, the recombinant nucleic acid molecule consists of the elements arranged in the above order.

Figure 7B:
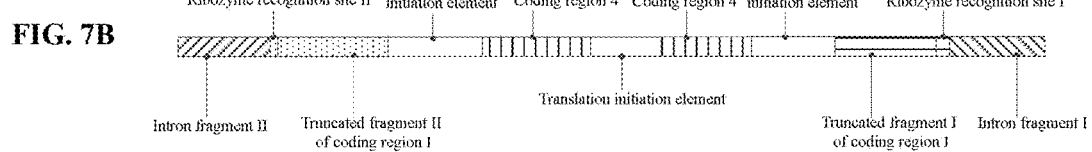

In some alternative embodiments, the coding region 4 has a quantity of two, and the recombinant nucleic acid molecule includes elements arranged in the following order: an intron fragment II, the truncated fragment II of the coding region 1, a translation initiation element, the coding region 4, a translation initiation element, the coding region 4, a translation initiation element, the truncated fragment I of the coding region 1, and an intron fragment I, as shown in FIG. 7B. In other embodiments, the recombinant nucleic acid molecule consists of the elements arranged in the above order.

Figure 7C:
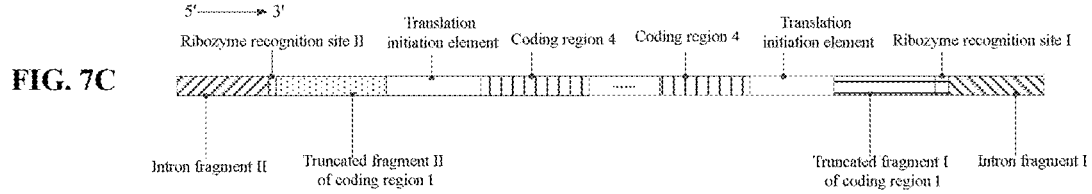

In some alternative embodiments, as shown in FIG. 7C, the coding region 4 has a quantity of at least two, and the recombinant nucleic acid molecule includes elements arranged in the following order: an intron fragment II, the truncated fragment II of the coding region 1, a translation initiation element, the at least one coding region 4, a translation initiation element, the at least one coding region 4, a translation initiation element, the truncated fragment I of the coding region 1, and an intron fragment I; where one translation initiation element is contained between any two coding regions 4. In other embodiments, the recombinant nucleic acid molecule consists of the elements arranged in the above order.

In some other embodiments, the truncated fragment III of the coding element and the truncated fragment IV of the coding element in the recombinant nucleic acid molecule are used to form a coding region 1, at least one coding region 4, and a translation initiation element located between any two adjacent coding regions. The 3' end of the truncated fragment III of the coding region 1 contains a ribozyme recognition site IV that consists of a first predetermined number of nucleotides located at the 3' end of the truncated fragment III of the coding region 1; and the 5' end of the truncated fragment IV of the coding region 1 contains a ribozyme recognition site III that consists of a second predetermined number of nucleotides located at the 5' end of the truncated fragment IV of the coding region 1. In the circular RNA prepared by the recombinant nucleic acid molecule in vitro, each coding region corresponds to one translation initiation element, allowing for tandem expression of at least two target polypeptides.

Figure 7D:
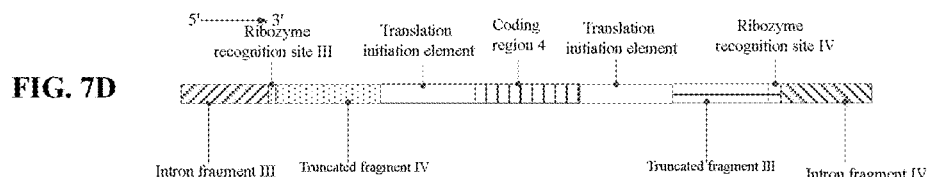
FIGS. 7D through 7F shows a schematic structural diagram of a recombinant nucleic acid molecule for preparing a circRNA according to the present disclosure (a Clean PIE system).

In some alternative embodiments, the coding region 4 has a quantity of one, and the recombinant nucleic acid molecule includes elements arranged in the following order: an intron fragment III, the truncated fragment IV of the coding region 1, a translation initiation element, the coding region 4, a translation initiation element, the truncated fragment III of the coding region 1, and an intron fragment IV, as shown in FIG. 7D. In other embodiments, the recombinant nucleic acid molecule consists of the elements arranged in the above order.

Figure 7E:
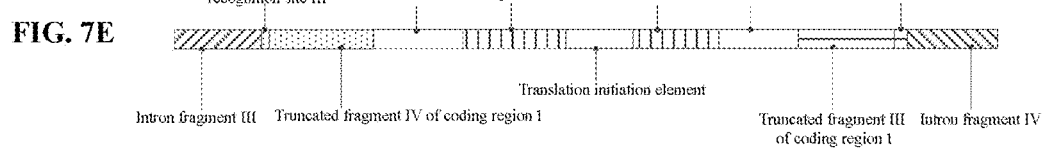

In some alternative embodiments, the coding region 4 has a quantity of two, and the recombinant nucleic acid molecule includes elements arranged in the following order: an intron fragment III, the truncated fragment IV of the coding region 1, a translation initiation element, the coding region 4, a translation initiation element, the coding region 4, a translation initiation element, the truncated fragment III of the coding region 1, and an intron fragment IV, as shown in FIG. 7E. In other embodiments, the recombinant nucleic acid molecule consists of the elements arranged in the above order.

Figure 7F:
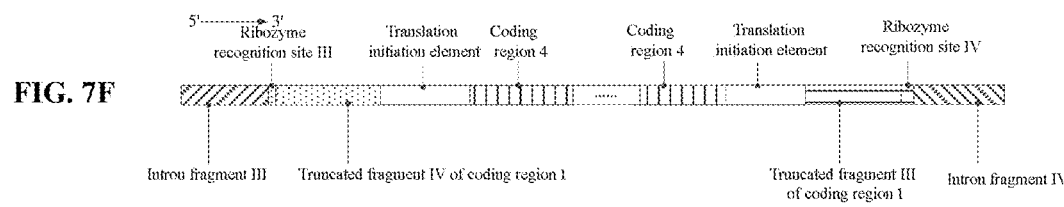

In some alternative embodiments, as shown in FIG. 7F, the coding region 4 has a quantity of at least two, and the recombinant nucleic acid molecule includes elements arranged in the following order: an intron fragment III, the truncated fragment IV of the coding region 1, a translation initiation element, the at least one coding region 4, a translation initiation element, the at least one coding region 4, a translation initiation element, the truncated fragment III of the coding region 1, and an intron fragment IV; where one translation initiation element is contained between any two coding regions 4. In other embodiments, the recombinant nucleic acid molecule consists of the elements arranged in the above order.

In the present disclosure, the coding region 1 and each coding region 4 encode any type of target polypeptide independently of one another. The target polypeptides encoded by the coding region 1 and any one coding region 4 may be the same or different, and the target polypeptides encoded by any coding region 4 may be the same or different.

In the circular RNA prepared by the recombinant nucleic acid molecule above, the 5' end of each coding region is correspondingly ligated to one translation initiation element, and the coding region 1 and the at least one coding region 4 are ligated in tandem by a plurality of translation initiation elements, allowing for expression of at least two target polypeptides.

In the present disclosure, the coding regions located at different positions are distinguished by numbering the coding regions (for example, coding region 1, coding region 4, etc.). Illustratively, the coding region 1 represents a coding region containing a ribozyme recognition site; the code region 4 represents a coding region between the truncated fragment I of the coding region 1 and the truncated fragment II of the coding region 2, or the coding region 4 represents a coding region between the truncated fragment III of the coding region 1 and the truncated fragment IV of the coding region 2.

Recombinant Expression Vector Containing Recombinant Nucleic Acid Molecule

In some embodiments, the recombinant nucleic acid molecule serves as a portion of a recombinant expression vector for preparing a circular RNA. The circular RNAs expressing a target polypeptide may be prepared in a process of transcription and circularization in vitro.

In other embodiments, the recombinant nucleic acid molecule may serve as a circularization precursor RNA molecule, or a part thereof obtained after linearization and transcription of the recombinant expression vector. That is, only circularization of the recombinant nucleic acid molecule is needed to obtain the circular RNA expressing a target polypeptide.

In some embodiments, the steps of preparing a circular RNA in vitro include:
transcribing the recombinant nucleic acid molecule according to any one item described above or the recombinant expression vector described above to form a circularization precursor nucleic acid molecule; and
circularizing the circularization precursor nucleic acid to obtain the circular RNA.

In some alternative embodiments, the method further includes a step of purifying the circular RNA.

Circular RNA

In some embodiments, the circular RNA of the present disclosure is prepared by using a Clean PIE system provided by the present disclosure, and includes elements arranged in the following order in the 5' to 3' direction: a translation initiation element, and a coding element for encoding at least one target polypeptide.

Figure 8A:
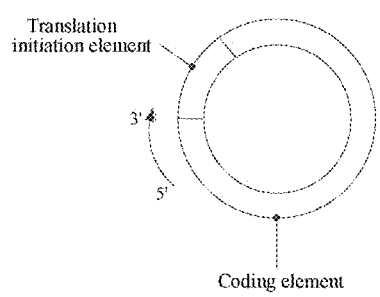
FIGS. 8A and 8B shows circRNA structures, wherein A shows circRNA structure prepared by the Clean PIE system of the present disclosure, and B shows circRNA structure prepared by the classic PIE system.
Figure 8B:
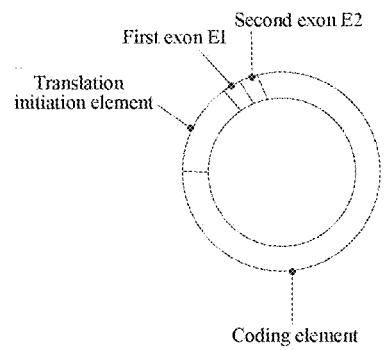

Compared with the circular RNA prepared by a classic PIE system shown in FIG. 8B, the circular RNA prepared by the Clean PIE system of the present disclosure does not introduce additional E1 and E2 sequences (FIG. 8A) under conditions ensuring integrity of protein-coding sequences, to guarantee sequence accuracy and secondary structure of the circular RNA, reduce natural immunogenicity of the circular RNA, and improve stability thereof in cells, thus making it suitable for clinical application fields, such as serving as a gene therapy vector, an expressing therapeutic protein, serving as a nucleic acid vaccine and the like, showing broad application prospects.

In some embodiments, the coding element of the circular RNA includes a coding region 1 and at least one in the group consisting of (i) to (ii): (i) at least one coding region 2, and (ii) at least one coding region 3. Each coding region encodes any type of target polypeptide independently of one another, and the circular RNA may encode one or more target polypeptides in tandem. Illustratively, the circular RNA expresses 1, 2, 3, 4, 5, 10, 15, 20, 25, or another number of target polypeptides.

As a preferred embodiment, two adjacent coding regions are linkeded by a linker, which is used to encode a linker peptide to separate target polypeptides encoded by the adjacent coding regions, enabling the same circular RNA to encode two or more target polypeptides.

Figure 9A:
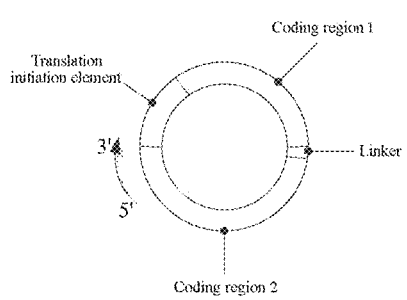
FIGS. 9A and 9B show circRNA structures prepared by the Clean PIE system of the present disclosure.

In some alternative embodiments, the circular RNA contains a translation initiation element, a coding region 1, a coding region 2, and a linker located between the coding region 1 and the coding region 2 in the 5' to 3' direction, as shown in FIG. 9A. The linker separates the coding region 1 from the coding region 2, enabling the circular RNA to express at least two target polypeptides in tandem in cells. In other alternative embodiments, the circular RNA consists of the elements arranged in the above order.

Figure 10A:
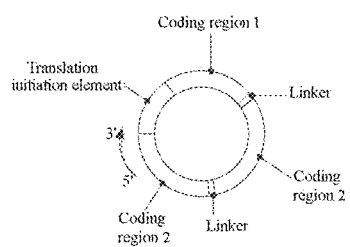
FIGS. 10A through 10C show circRNA structures prepared by the Clean PIE system of the present disclosure.

In some alternative embodiments, the coding region 2 may have a quantity of two or more. Illustratively, the circular RNA contains a translation initiation element, a coding region 1, two coding regions 2 (for convenience of description, designated as a first coding region 2 and a second coding region 2 in the 5' to 3' direction), a linker located between the coding region 1 and the first coding region 2, and a linker located between the first coding region 2 and the second coding region 2 in the 5' to 3' direction, as shown in FIG. 10A. The above-mentioned circular RNA may allow for tandem expression of three or more target polypeptides in cells. In other alternative embodiments, the circular RNA consists of the elements arranged in the above order.

Figure 9B:
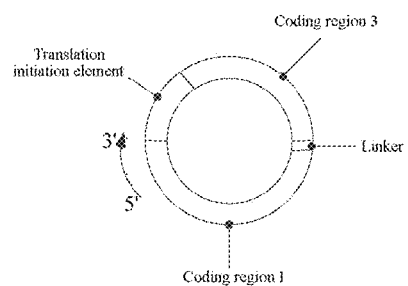

In some alternative embodiments, the circular RNA contains a translation initiation element, a coding region 3, a coding region 1, and a linker located between the coding region 1 and the coding region 3 in the 5' to 3' direction, as shown in FIG. 9B. The linker separates the coding region 1 from the coding region 3, enabling the circular RNA to express at least two target polypeptides in tandem in cells. In other alternative embodiments, the circular RNA consists of the elements arranged in the above order.

Figure 10B:
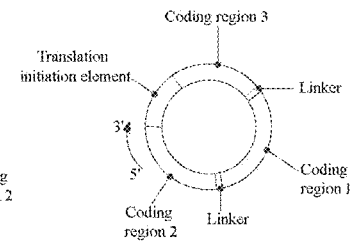
Figure 10C:
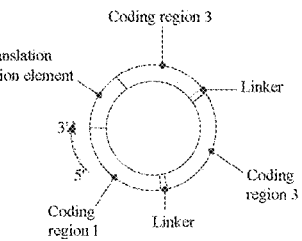

In some alternative embodiments, the coding region 3 may have a quantity of two or more. Illustratively, the circular RNA contains a translation initiation element, two coding regions 3 (for convenience of description, designated as a first coding region 3 and a second coding region 3 in the 5' to 3' direction), a coding region 1, a linker located between the coding region 1 and the second coding region 3, and a linker located between the first coding region 3 and the second coding region 3 in the 5' to 3' direction, as shown in FIG. 10C. The above-mentioned circular RNA may allow for tandem expression of three or more target polypeptides in cells. In other alternative embodiments, the circular RNA consists of the elements arranged in the above order.

In some alternative embodiments, the circular RNA contains both a coding region 2 and a coding region 3. Illustratively, the circular RNA contains a translation initiation element, a coding regions 3, a coding region 1, a coding region 2, a linker located between the coding region 1 and the coding region 3, and a linker located between coding region 1 and coding region 2 in the 5' to 3' direction, as shown in FIG. 10B. The above-mentioned circular RNA may allow for tandem expression of three or more target polypeptides in cells. In other alternative embodiments, the circular RNA consists of the elements arranged in the above order.

In the present disclosure, the coding region 1, each coding region 2 and each coding region 3 encode any type of target polypeptide independently of one another. The target polypeptide encoded by the coding region 1 and any one coding region 2 may be the same or different, the target polypeptide encoded by the coding region 1 and any one coding region 3 may be the same or different, the target polypeptide encoded by any two coding regions 2 may be the same or different, the target polypeptide encoded by any two coding regions 3 may be the same or different, and the target polypeptide encoded by any one coding region 2 and any one coding region 3 may be the same or different.

In some embodiments, the coding regions of the circular RNA includes one coding region 1 and at least one coding region 4, and the 5' end of any one coding region is ligated to a translation initiation element. Illustratively, the coding region 4 has a quantity of 1, 2, 3, 4, 5, 10, 15, 20, 25, and the like. The transcription of different coding regions is initiated by using a translation initiation element ligated to the 5' end of each coding region, enabling the same circular RNA to encode two or more target polypeptides.

Figure 11A:
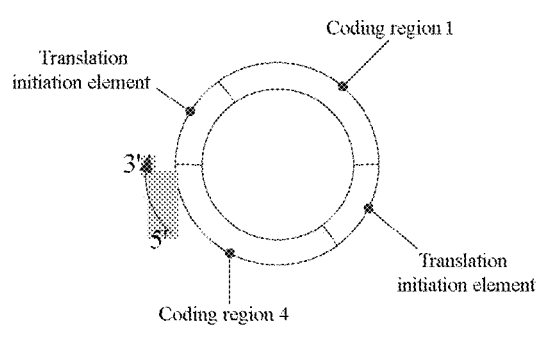
FIGS. 11A and 11B shows circRNA structure prepared by the Clean PIE system of the present disclosure.

In some alternative embodiments, the coding region 4 has a quantity of one, and the circular RNA contains a translation initiation element, a coding region 1, a translation initiation element, and a coding region 4 in the 5' to 3' direction, as shown in FIG. 11A. The above-mentioned circular RNA may allow for tandem expression of two target polypeptides in cells. In other alternative embodiments, the circular RNA consists of the elements arranged in the above order.

Figure 11B:
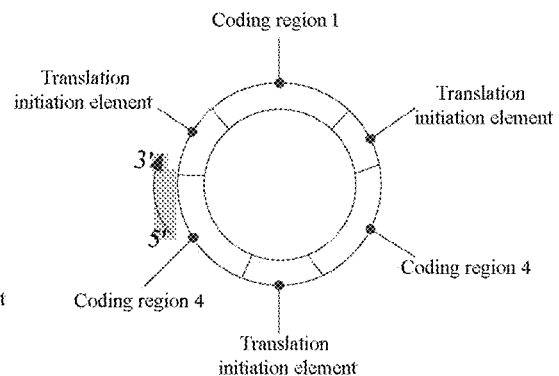
Figure 12:
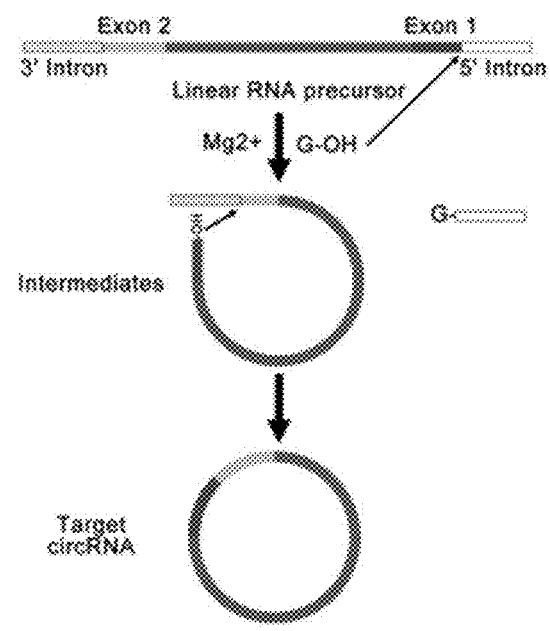
FIG. 12 shows a schematic procedure diagram of forming a circRNA by circularization of a classic PIE system.

In some alternative embodiments, the coding region 4 may have a quantity of at least two. Illustratively, the circular RNA contains a translation initiation element, a coding region 1, a translation initiation element, at least two coding regions 4, and a translation initiation element located between the at least two coding regions 4 in the 5' to 3' direction, as shown in FIG. 11B. The above-mentioned circular RNA may allow for tandem expression of two target polypeptides in cells. In other alternative embodiments, the circular RNA consists of the elements arranged in the above order.

In the present disclosure, the coding region 1 and each coding region 4 encode any type of target polypeptide independently of one another. The target polypeptide encoded by the coding region 1 and any one coding region 4 may be the same or different, and the target polypeptide encoded by any two coding regions 4 may be the same or different.

In some alternative embodiments, the circular RNA contains an insertion element. The insertion element is ligated to the 5' end of any translation initiation element.

Methods for Screening Target Coding Region Sequence Containing Ribozyme Recognition Site In some embodiments, the present disclosure provides a method for screening a target coding region sequence containing a ribozyme recognition site, including the following steps:

S1, extracting m amino acid units from the target polypeptide containing q amino acids in the N-terminal-to-C-terminal direction, with each of amino acid units containing n amino acids; where at least one repeated amino acid is contained between any two adjacent amino acid units, n is an integer and n≥2, m is an integer and m≥1.

Specifically, in the N-terminal-to-C-terminal direction, the extracted m amino acid units are sequentially designated as amino acid units $R_1$ to $R_M$. A quantity of the amino acids in each amino acid unit from $R_1$ to $R_M$ is n, and at least one identical amino acid is contained between any two adjacent amino acid units, with a quantity of amino acid units is any integer from 1 to (n−1). As a preferred embodiment, the quantity of repeated amino acids between any two adjacent amino acid units is n−1.

Illustratively, the target polypeptide sequentially consists of $AA_1$ to $AA_q$ amino acids in the N-terminal-to-C-terminal direction. When extracting the amino acids from the target polypeptide, a total number of n amino acids ($AA_1$ included) are extracted as an amino acid unit $R_1$, with $AA_1$ as a start amino acid.

Furthermore, when extracting the amino acid unit $R_2$, a start position for extracting the amino acid unit $R_2$ may be any position from positions [2] to [n] in the amino acid unit $R_1$. For example, when n is 2, a start amino acid of the amino acid unit $R_2$ is the amino acid at the position [2] in the amino acid unit $R_1$. When n is 3, the start amino acid of the amino acid unit $R_2$ is the amino acid at the position [2] or [3] in the amino acid unit $R_1$ ($AA_2$ or $AA_3$). When n is 4, the start amino acid of the amino acid unit $R_2$ is the amino acid at the position [2], [3] or [4] in the amino acid unit $R_1$ ($AA_2$, $AA_3$ or $AA_4$). Analogy may be made with the increase of n, which is not exhaustive herein.

As a preferred embodiment, the start amino acid of the amino acid unit $R_2$ is the amino acid at the position [2] in the amino acid unit $R_1$. For example, when n is any integer of 2 or more, a start amino acid of the amino acid unit $R_2$ is always $AA_2$.

Furthermore, when extracting the amino acid unit $R_3$, a start position for extracting the amino acid unit $R_3$ may be any position from position [2] to [n] in the amino acid unit $R_2$. For example, when n is 2, a start amino acid of the amino acid unit $R_3$ is the amino acid at the position [2] in the amino acid unit $R_2$. When n is 3, the start amino acid of the amino acid unit $R_3$ is the amino acid at the position [2] or [3] in the amino acid unit $R_2$. When n is 4, the start amino acid of the amino acid unit $R_3$ is the amino acid at the position [2], [3] or [4] in the amino acid unit $R_2$. Analogy may be made with the increase of n, which is not exhaustive herein.

As a preferred embodiment, the start amino acid of the amino acid unit $R_3$ is the amino acid at the position [2] in the amino acid unit $R_2$. For example, when n is any integer of 2 or more, the start amino acid of the amino acid unit $R_3$ is always $AA_3$.

Furthermore, the start position for extracting the amino acid unit $R_4$ may be any position from positions [2] to [n] in the amino acid unit $R_3$. For example, when n is 2, the start amino acid of the amino acid unit $R_4$ is the amino acid at a position [2] in the amino acid unit $R_3$. When n is 3, the start amino acid of the amino acid unit $R_4$ is the amino acid at the position [2] or [3] in the amino acid unit $R_3$. When n is 4, the start amino acid of the amino acid unit $R_4$ is the amino acid at the position [2], [3] or [4] in the amino acid unit $R_3$. Analogy may be made with the increase of n, which is not exhaustive herein.

As a preferred embodiment, the start amino acid of the amino acid unit $R_4$ is the amino acid at the position [2] in the amino acid unit $R_3$. For example, when n is any integer of 2 or more, the start amino acid of the amino acid unit $R_4$ is always $AA_4$.

The extraction of amino acid units is carried out in the above manner until the amino acid unit $R_m$ is extracted.

In a preferred embodiment, a target polypeptide sequence consisting of q amino acids is split, with a step of 1 and a window length of n, to obtain m amino acid units, where $m=q+1-n$, n is an integer and $n≥2$, m is an integer and $m≥1$.

S2, determining m codon sequence sets, where each of the codon sequence sets includes a codon sequence corresponding to each of the amino acid unit.

Specifically, according to the degeneracy principle of amino acid codons, the codon sequence set corresponding to each amino acid unit is obtained. Codon sequence sets $C_1$-$C_m$ are obtained corresponding to amino acid units $R_1$-$R_m$.

S3, traversing the m codon sequence sets to obtain a matching value of each codon sequence in each of the codon sequence sets with a target motif.

Specifically, the target motif contains a ribozyme recognition site sequence that is formed by ligating the nucleotide sequence of a ribozyme recognition site I to the nucleotide sequence of a ribozyme recognition site II, or formed by ligating the nucleotide sequence of a ribozyme recognition site III to the nucleotide sequence of a ribozyme recognition site IV. Illustratively, ribozyme recognition site sequences include, but are not limited to, "5'-TTGGG<u>TCT</u>-3'", "5'-ACGTCT<u>TA</u>ACCAA-3'", "5'-AGGGA<u>TC</u>A-3'", and the like.

Furthermore, the target motif also contains x nucleotide(s) ligated to at least one of the 5' end and the 3' end of the ribozyme recognition site sequence, to form a target motif consisting of 3n nucleotides. Each x is an integer ≥0 independently of one another, and each ligated nucleotide is selected from any type of nucleotide independently of one another. For example, when the ribozyme recognition site sequence is "5'-TTGGG<u>TCT</u>-3'", the target motif may correspond to at least one selected from the following (a1) to (a6), where X=A, T, C, G:

(a1)
TTGGGTCTX;

(a2)
XTTGGGTCT;

(a3)
XTCTGGGTT;

(a4)
TCTGGGTTX;

(a5)
XXTTGGGTCTXX;

(a6)
XXTCTGGGTTXX.

In some embodiments, the step of traversing m codon sequence sets to obtain a matching value of each codon sequence in each of codon sequence sets with a target motif includes aligning each codon sequence in the codon sequence sets $C_1$-$C_m$ with the target motif to calculate the matching value of each codon subsequence.

Furthermore, the target motif contains an effective base pair that corresponds to two bases at a linking position of the ribozyme recognition site I and the ribozyme recognition site II. That is, the effective base pair refers to the two bases used for circularization in the ribozyme recognition site. For example, when the sequence of ribozyme recognition site is "5'-TTGG<u>GTCT</u>-3'", the effective base pair refers to <u>TC</u> therein. When the sequence of the ribozyme recognition site is "5'-ACGTCT<u>TA</u>ACCAA-3'", the effective base pair refers to <u>TA</u> therein. When the sequence of ribozyme recognition site is "5'-AGGGA<u>TC</u>A-3'", the effective base pair refers to <u>TC</u> therein.

When aligning each codon sequence with the target motif, it is determined whether bases at positions in the codon sequence corresponding to the effective base pair are effective bases, and if the codon sequence does not contain the effective base pair, then an alignment value of the codon sequence is not outputted.

If the codon sequence contains the effective base pair, the alignment value between each base in each codon sequence with the corresponding base in the target motif in the 5' to 3' direction is determined.

The matching value of each codon sequence with the target motif is obtained based on the alignment value of each base in each codon sequence.

Illustratively, when the target motif may correspond to at least one selected from (a1) to (a6): (a1) TTGGGTCTX; (a2) XTTGGGTCT; (a3) XTCTGGGTT; (a4) TCTGGGTTX; (a5) XXTTGGGTCTXX; (a6) XXTCTGGGTTXX, where X=A, T, C, G. The traversing m codon sequence sets to obtain a matching value of each codon sequence in each of the codon sequence sets with a target motif includes:

S31: by taking (a1) TTGGGTCTX as the target motif, transversing each codon sequence of the codon sequence sets $C_1$-$C_m$ to calculate the matching value of each codon sequence with target motif. For a codon sequence, the 6th position therein must be base "T", and the 7th position therein must be base "C", or the matching value is not outputted. When the codon sequence contains an effective base pair, the bases at positions 1 to 9 are successively aligned, and scores are accumulated according to the alignment results.

S32: by taking (a2) XTTGGGTCT as the target motif, traversing each codon sequence of the codon sequence sets $C_1$-$C_m$ to calculate the matching value of each codon sequence with the target motif. For a codon sequence, the 7th position therein must be base "T", and the 8th position therein must be base "C", or the matching value is not outputted. When the codon sequence contains an effective base pair, the bases at positions 1 to 9 are successively aligned, and scores are accumulated according to the alignment results.

S33: by taking (a3) XTCTGGGTT as the target motif, traversing each codon sequence of the codon sequence sets $C_1$-$C_m$ to calculate the matching value of each codon sequence with the target motif. For a codon sequence, the 3th position therein must be base "C", and the 4th position therein must be base "T", or the matching value is not outputted. When the codon sequence contains an effective base pair, the bases at positions 1 to 9 are successively aligned, and scores are accumulated according to the alignment results.

S33: by taking (a3) XTCTGGGTT as the target motif, traversing each codon sequence of the codon sequence sets $C_1$-$C_m$ to calculate the matching value of each codon sequence with the target motif. For a codon sequence, the 3th position therein must be base "C", and the 4th position therein must be base "T", or the matching value is not outputted. When the codon sequence contains an effective base pair, the bases at positions 1 to 9 are successively aligned, and scores are accumulated according to the alignment results.

S34: by taking (a4) TCTGGGTTX as the target motif, traversing each codon sequence of the codon sequence sets $C_1$-$C_m$ to calculate the matching value of each codon sequence with the target motif. For a codon sequence, the 3rd position therein must be base "T", and the 2nd position therein must be base "C", or the matching value is not outputted. When the codon sequence contains an effective base pair, the bases at positions 1 to 9 are successively aligned, and scores are accumulated according to the alignment results.

S35: by taking (a5) XXTTGGGTCTXX as the target motif, traversing each codon sequence of the codon sequence sets $C_1$-$C_m$ to calculate the matching value of each codon sequence with the target motif. For a codon sequence, the 7th position therein must be base "T", and the 8th position therein must be base "C", or the matching value is not outputted. When the codon sequence contains an effective base pair, the bases at positions 1 to 9 are successively aligned, and scores are accumulated according to the alignment results.

S36: by taking (a6) XXTCTGGGTTXX as the target motif, traversing each codon sequence of the codon sequence sets $C_1$-$C_m$ to calculate the matching value of each codon sequence with the target motif. For a codon sequence, the 4th position therein must be base "C", and the 5th position therein must be base "T", or the matching value is not outputted. When the codon sequence contains an effective base pair, the bases at positions 1 to 9 are successively aligned, and scores are accumulated according to the alignment results.

In some embodiments, the obtaining a matching value of each codon sequence in each of the codon sequence sets with a target motif further includes: determining whether each codon sequence in each codon sequence set is hybridized with an intron sequence to obtain a complementary value of each codon sequence in each of codon sequence sets.

Illustratively, by traversing each codon sequence of the codon sequence sets $C_1$-$C_m$, based on whether each codon sequence is hybridized with an intron sequence, the complementary value of each codon sequence is obtained; and in combination of the complementary value with the alignment value, a final matching value of each codon sequence is obtained.

S4, determining the target codon sequence in the codon sequence set based on the matching value, where a position of the target codon sequence corresponding to the coding region sequence is an implantation position of the ribozyme recognition site, and the coding region sequence containing the target codon sequence at the implantation position is the target coding region sequence containing the ribozyme recognition site.

Specifically, after obtaining the matching value of each codon sequence in each of codon sequence sets with a target motif, the codon sequence with the matching value higher than a first threshold is selected as the target codon sequence. The position of the target codon sequence corresponding to the coding region sequence is the implantation position of ribozyme recognition site. For the target coding region sequence, the nucleotide sequence at the implantation position is the target codon sequence.

Furthermore, the target codon sequence is truncated at the position of the effective base pair in the target codon sequence, to provide the truncated fragment I of the coding element and the truncated fragment II of the coding element, or provide the truncated fragment III of the coding element and the truncated fragment IV of the coding element, either of which may be applied to the Clean PIE system for circularization.

In the present disclosure, the "first threshold" refers to a value that when the matching value between the codon sequence and the target motif is higher than this value, the truncated fragments of the coding element may be applied to the Clean PIE system for effective circularization.

In the present disclosure, as a limited number of base mutations in the ribozyme recognition site sequence have no impact on effective circularization of the ribozyme recognition site, for the target codon sequence, mutant bases not matching the target motif are allowed at certain positions.

Methods for Screening Ribozyme Recognition Sites

In some embodiments, the present disclosure provides a method for screening a target coding region sequence containing a ribozyme recognition site, the method including the following steps:

(1) Determining a sequence to be screened, which contains an intron sequence derived from Group I intron, a first exon sequence ligated to the 5' end of the intron sequence, and a second exon sequence ligated to the 3' end of the intron sequence.

Specifically, the sequence to be screened may be any type of sequence with self-splicing activity of Group I intron.

(2) Obtaining a predicted RNA secondary structure based on the sequence to be screened.

Specifically, the obtaining the RNA secondary structure of the sequence to be screened includes:

receiving, by a sequence alignment software (for example, ClustalW), an input of a sequence to be screened, to determine highly conserved sequences P7 and P7' in the sequence to be screened derived from the Group I intron, and determine J6/7 and J8/7 sequences to obtain first pairing information;

determining P3, and determining whether a P3' sequence exists after P7, and if not, adding a P3' sequence, to obtain second pairing information;

determining one or more of the following sequences: P2, P4, P5, P6, P8, and P9, according to the first pairing information and the second pairing information, and further according to a typical structure of the Group I intron (FIG. 34);

determining P1' and P10 together with the ribozyme recognition site by a first exon sequence at the 5' end and a second exon sequence at the 3' end; and predicting by the method based on minimum free energy in Mfold or RNAstructure using the obtained pairing information to obtain the predicted RNA secondary structure.

(3) Obtaining a ribozyme recognition site I with ribozyme recognition activity in the first exon sequence and a ribozyme recognition site II with ribozyme recognition activity in the second exon sequence based on the predicted RNA secondary structure.

In some embodiments, the nucleotide sequence of the ribozyme recognition site I is hybridized with a leader sequence in the intron sequence, or the nucleotide sequence of the ribozyme recognition site II is hybridized with a leader sequence in the intron sequence. The nucleotide sequence of the ribozyme recognition site I and/or the ribozyme recognition site II are hybridized with the leader sequence in the intron sequence, keeping two ends of the Clean PIE system close to each other during self-splicing to form a circular RNA, which facilitates successive cleavage and ligating at positions of the ribozyme recognition site I and the ribozyme recognition site II to form the circular RNA.

As a limited number of base mutations in the ribozyme recognition site sequence have no impact on effective circularization of ribozyme recognition site, in some embodiments, the bases on the ribozyme recognition site I are successively replaced to obtain a mutant sequence of the ribozyme recognition site I with ribozyme recognition activity. In some embodiments, the bases on the ribozyme recognition site II are successively replaced to obtain a mutant sequence of the ribozyme recognition site II with ribozyme recognition activity.

(4) Determining the ribozyme recognition site sequence based on the nucleotide sequence of the ribozyme recognition site I and the nucleotide sequence of the ribozyme recognition site II. Specifically, the ribozyme recognition site sequence contains at least one selected from the group consisting of (i) to (iv):

(i) the nucleotide sequence of the ribozyme recognition site I,
(ii) the nucleotide sequence of the ribozyme recognition site II,
(iii) a mutant sequence of the ribozyme recognition site I with ribozyme recognition activity,
(iv) a mutant sequence of the ribozyme recognition site II with ribozyme recognition activity.

In some embodiments, the ribozyme recognition site contains (i) the nucleotide sequence of the ribozyme recognition site I, and (ii) the nucleotide sequence of the ribozyme recognition site II. In other embodiments, the ribozyme recognition site consists of (i) the nucleotide sequence of the ribozyme recognition site I and (ii) the nucleotide sequence of the ribozyme recognition site II.

In some embodiments, the ribozyme recognition site contains (iii) a mutant sequence of the ribozyme recognition site I with ribozyme recognition activity, and (iv) a mutant sequence of the ribozyme recognition site II with ribozyme recognition activity. In other embodiments, the ribozyme recognition site consists of (iii) a mutant sequence of the ribozyme recognition site I with ribozyme recognition activity and (iv) a mutant sequence of the ribozyme recognition site II with ribozyme recognition activity.

In some embodiments, the ribozyme recognition site contains (i) the nucleotide sequence of the ribozyme recognition site I, and (iv) a mutant sequence of the ribozyme recognition site II with ribozyme recognition activity. In other embodiments, the ribozyme recognition site consists of (i) the nucleotide sequence of the ribozyme recognition site I and (iv) a mutant sequence of the ribozyme recognition site II with ribozyme recognition activity.

In some embodiments, the ribozyme recognition site contains (iii) a mutant sequence of the ribozyme recognition site I with ribozyme recognition activity, and (ii) the nucleotide sequence of the ribozyme recognition site II. In other embodiments, the ribozyme recognition site consists of (iii) a mutant sequence of the ribozyme recognition site I with ribozyme recognition activity, and (ii) the nucleotide sequence of the ribozyme recognition site II.

Screening System for Screening Target Coding Region Sequence Containing Ribozyme Recognition Site In some embodiments, the present disclosure provides a screening system for screening a target coding region sequence containing a ribozyme recognition site, which includes:

a target motif constructing module configured to ligate x nucleotide to at least one end of the 5' end and the 3' end of a ribozyme recognition site sequence to obtain a target motif with 3n nucleotide; where each x is an integer ≥0 independently of one another, and each ligated nucleotide is selected from any type of nucleotide independently of one another;

an amino acid unit extraction module configured to extract m amino acid units from the target polypeptide containing q amino acids in the N-terminal-to-C-terminal direction, with each of the amino acid units containing n amino acids; where at least one repeated amino acid is contained between any two adjacent amino acid units, n is an integer and n≥2, m is an integer and m≥1; preferably, m=q+1−n;

a codon sequence set extraction module configured to determine m codon sequence sets, where each of the codon sequence sets includes a codon sequence corresponding to each of the amino acid units;

a matching value calculation module configured to traverse the m codon sequence sets to obtain a matching value of each codon sequence in each of the codon sequence sets with the target motif;

a target codon sequence screen module configured to determine the target codon sequence in the codon sequence set based on the matching value, where a position of the target codon sequence corresponding to the coding region sequence is an implantation position of the ribozyme recognition site, and the coding region sequence containing the target codon sequence at the implantation position is the target coding region sequence containing the ribozyme recognition site.

In some embodiments, the matching value calculation module includes:

an effective base pair determination unit configured to determine whether a base at the position corresponding to an effective base pair in the codon sequence is an effective base, and if the codon sequence does not contain the effective base pair, disable output of the alignment value of the codon sequence;

an alignment value determination unit configured to determine the alignment value between each base in each codon sequence with the corresponding base in the target motif in the 5' to 3' direction;

a matching value output unit configured to obtain the matching value of each codon sequence with the target motif based on the alignment value of each base in each codon sequence.

In some embodiments, the matching value calculation module further includes:

a complementary value calculation module configured to determine whether each codon sequence in each of the codon sequence sets is hybridized with an intron sequence to obtain the complementary value of each codon sequence in each of the codon sequence sets;

the matching value output unit configured to determine the matching value of each codon sequence in each of the codon sequence sets with the target motif based on the alignment value and the complementary value.

Moreover, the present disclosure also discloses a processing device for screening a target coding region sequence containing a ribozyme recognition site, which includes:

a memory configured to store computer programs;

a processor configured to execute a computer program to implement the above method for screening a target coding region sequence containing a ribozyme recognition site.

Moreover, the present disclosure also discloses a computer-readable storage medium, on which a computer program is stored, which, when executed by a processor, implements the above method for screening a target coding region sequence containing a ribozyme recognition site.

It may be further appreciated by those skilled in the art that the units and algorithm steps of each example described in connection with the embodiments disclosed herein may be implemented by electronic hardware, computer software, or a combination thereof. In order to clearly illustrate the interchangeability of hardware and software, components and steps of each example have been generally described in terms of functions in the above description. Whether these functions are performed by hardware or software depends on the specific application and design constraints of the technical scheme. Those skilled in the art may use different methods to achieve the described functions for each specific application, which should not be construed as beyond the scope of the present disclosure.

EXAMPLES

Other objects, features and advantages of the present disclosure will become apparent from the following detailed description. However, it should be understood that the detailed description and specific examples (although indicating the embodiments of the present disclosure) are given only for purposes of illustration, as various changes and modifications made within the spirit and scope of the present disclosure will become apparent to those skilled in the art after reading the detailed description.

Unless otherwise specified, the experimental techniques and methods used in the examples herein are conventional ones, such as those without specific conditions in the following examples, which are carried out in accordance with conventional conditions such as those described in Sambrook et al., Molecular Cloning: Laboratory Manual (New York: Cold Spring Harbor Laboratory Press, 1989) or those suggested by manufacturers. The materials and reagents used are commercially available, unless otherwise specified.

Example 1: Matching Value Calculation Module

This example illustrates the scoring cateria of matching value calculation module in the screening system for target coding region sequences. The scoring principle of the matching calculation module is intended to find a target codon sequence closest to Group I intron PIE E1E2 in the ORF (open reading frame) of the circularization gene according to the degeneracy principle of encoding amino acids, thereby determining a ribozyme recognition site in the coding region.

Figure 16:
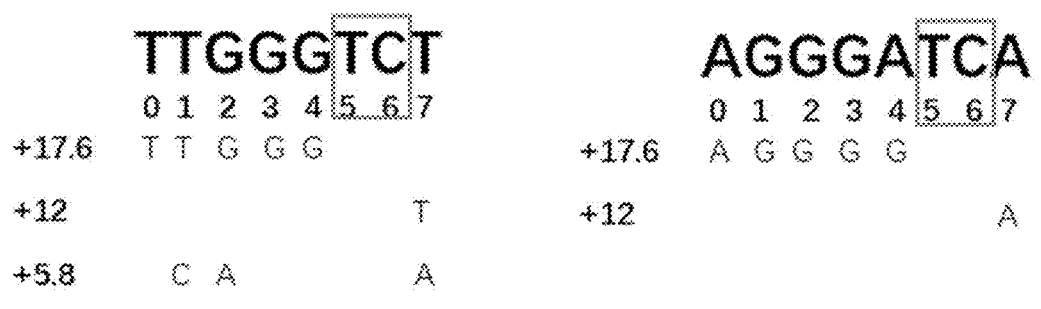
FIG. 16 shows scoring criteria for screening a target coding fragment sequence including a ribozyme recognition site, by taking a T4td PIE as an example.

If there was no target codon sequence completely matching to the Group I intron E1E2 in the coding region, the scoring was performed according to the following principles:

1. The completely matched sequence was taken as the baseline and given a score of 100. By taking T4td PIE as an example, the scoring cateria are shown in FIG. 16:

The score was 17.6 if the 1st position of the sequence was "T", or it was 0. If the 2nd position of the sequence was "T" and "C", the score was accumulated by 17.6 and 5.8, respectively, or by 0. If the 3rd position of the sequence was "G" and "A", the score was accumulated by 17.6 and 5.8 respectively, or by 0. If the 4th position of the sequence was "G", the score was accumulated by 17.6, or by 0. if the 5th position of the sequence was "G", the score was accumulated by 17.6, or by 0. If the 8th position of the sequence was "T" and "A", the score was accumulated by 12 and 5.8, respectively, or by 0. Finally, the total score was the scoring of the sequence.

2. The E1E2 sequences were counted, and the bases (effective base pair) at the circularization site were excluded, which were not scored (taking T4td PIE as an example, where E1E2 sequence was TTGGGTCT and TC was the circularization site, then TC was not scored).

Weighted average was carried out according to the following four situations:
a) if the sequence in the coding region completely matched the E1E2 sequence, and the circularization position sequence in the coding region was base complementary to IG sequence (a leader sequence) in the intron, then the weighted average was 3;
b) if the sequence in the coding region completely matched the E1E2 sequence, whereas the circularization position sequence in the coding region was not base complementary to IG sequence (a leader sequence) in the intron, then the weighted average was 2;
c) if sequences in the coding region cannot match E1E2 sequence, whereas the circularization position sequence in the coding region was base complementary to IG sequence (guide sequence) in the intron, then the weighted average was 1; and
b) if sequences in the coding region cannot match the E1E2 sequence, and the circularization position sequence in the coding region was not base complementary to IG sequence (guide sequence) in the intron, then the weighted average was 0.

The circularization sequence may be scored based on the above principles.

The present circularization sequence scoring system may be applied to Example 2 to obtain the target codon sequence, which is the same as or similar to the Group I intron PIE E1E2 sequence.

Figure 17:
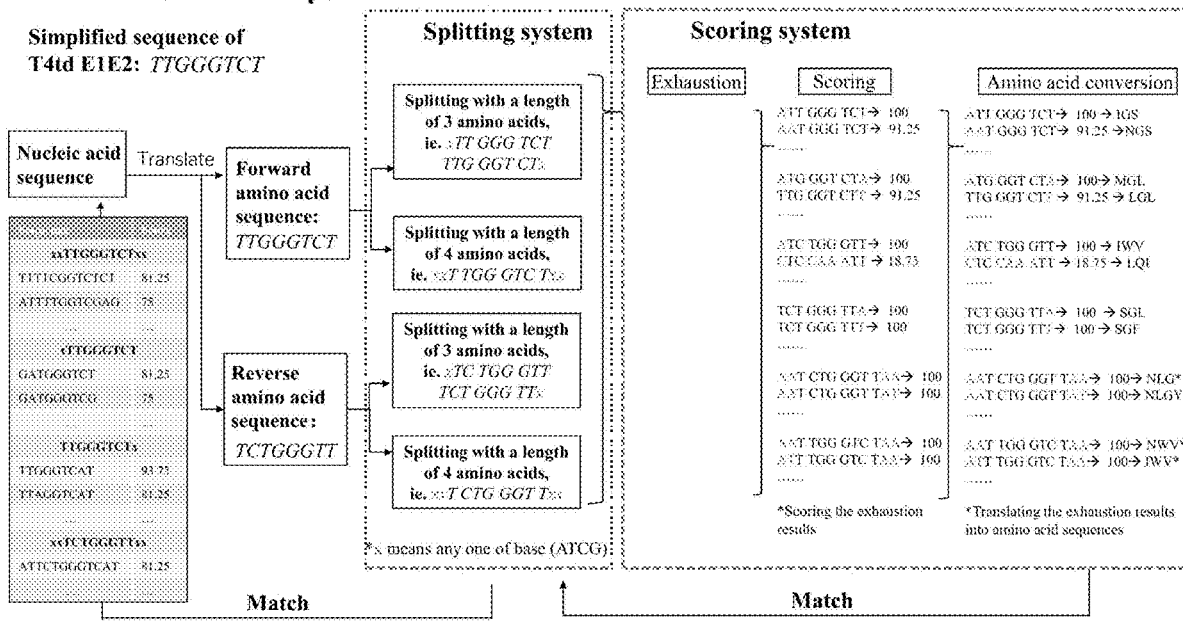
FIG. 17 shows an automated flow chart for determining a target including a ribozyme recognition site by using a screening system.

Example 2: Screening for Target Coding Region Sequence Containing Ribozyme Recognition Site FIG. 17 shows an automated flow chart for determining a target containing a ribozyme recognition site using the screening system, which was performed as follows:

(1) converting the coding region of a complete gene sequence into an amino acid sequence;

(2) in the amino acid unit extraction module, performing a slide window on the amino acid sequence, with a step of 1 (step=1) and a window length of 3 or 4 (win=3, 4), to obtain a short amino acid sequence with a length of 3 or 4;

(3) in the codon sequence set extraction module, translating the short amino acid sequence obtained in (2) into a nucleotide sequence according to the codon table in (1) to obtain a codon sequence set; and (4) in the matching value calculation module, scoring the codon sequence, with the E1E2 sequence as the ribozyme recognition site being TGGGTCT and taking the following sequences as the target motif, respectively, successively calculating the matching values of the codon sequences in the codon sequence sets with the target motif, where X=A, T, C, G.

```
TTGGGTCTX;

XTTGGGTCT;

XTCTGGGTT;

TCTGGGTTX;

XXTTGGGTCTXX;

XXTCTGGGTTXX.
``` i) The sequences obtained in (3) were traversed (win=3, with a sequence length of 9 bp) and scored based on TTGGGTCTX (X=A, T, C, G), and the 6th position of the sequence must be the base "T" and the 7th position must be the base "C". If the 1st position of the sequence was "T", the score was 17.6, or it was 0. If the 2nd position of the sequence was "T" and "C", the score was accumulated by 17.6 and 5.8, respectively, or by 0. If the 3rd position of the sequence was "G" and "A", the score was accumulated by 17.6 and 5.8, respectively, or by 0. If the 4th position of the sequence was "G", the score was accumulated by 17.6, or by 0. If the 5th position of the sequence was "G", the score was accumulated by 17.6, or by 0. If the 8th position of the sequence was "T" and "A", the score was accumulated by 12 and 5.8, respectively, or by 0.

ii) The sequences obtained in (3) were traversed (win=3, with a sequence length of 9 bp) and scored based on XTTGGGTCT (X=A, T, C, G), and the 7th position of the sequence must be the base "T" and the 8th position must be the base "C". If the 2nd position of the sequence was "T", the score was 17.6, or it was 0. If the 3rd position of the sequence was "T" and "C", the score was accumulated by 17.6 and 5.8, respectively, or by 0. If the 4th position of the sequence was "G" and "A" the score was accumulated by 17.6 and 5.8, respectively, or by 0. If the 5th position of the sequence was "G", the score was accumulated by 17.6, or by 0. If the 6th position of the sequence was "G", the score was accumulated by 17.6, or by 0. If the 9th position of the sequence was "T" and "A"", the score was accumulated by 12 and 5.8, respectively, or by 0.

iii) The sequences obtained in (3) were traversed (win=3, with a sequence length of 9 bp) and scored based on XTCTGGGTT (X=A, T, C, G), and the 3rd position of the sequence must be the base "C" and the 4th position must be the base "T", If the 9th position of the sequence was "T", the score was 17.6, or it was 0. If the 8th position of the sequence was "T" and "C", the score was accumulated by 17.6 and 5.8, respectively, or by 0. If the 7th position of the sequence was "G" and "A", the score was accumulated by 17.6 and 5.8, respectively, or by 0. If the 6th position of the sequence was "G", the score was accumulated by 17.6, or by 0. If the 5th position of the sequence was "G", the score was accumulated by 17.6, or by 0. If the 2nd position of the sequence was "T" and "A", the score was accumulated by 12 and 5.8, respectively, or by 0.

iv) The sequences obtained in (3) were traversed (win=3, with a sequence length of 9 bp) and scored based on TCTGGGTTX (X=A, T, C, G), and the 3rd position of the sequence must be the base "T" and the 2nd position must be the base "C". If the 8th position of the sequence was "T", the score was 17.6, or it was 0. If the 7th position of the sequence was "T" and "C", the score was accumulated by 17.6 and 5.8, respectively, or by 0. If the 6th position of the sequence was "G" and "A", the score was accumulated by 17.6 and 5.8, respectively, or by 0. If the 5th position of the sequence was "G", the score was accumulated by 17.6, or by 0. If the 4th position of the sequence was "G", the score was accumulated by 17.6, or by 0. If the 1st position of the sequence was "T" and "A", the score was accumulated by 12 and 5.8, respectively, or by 0.

v) The sequences obtained in (3) were traversed (win=4 with a sequence length of 12 bp) and scored based on XXTTGGGTCTXX (X=A, T, C, G), and the 7th position of the sequence must be the base "T" and the 8th position must be the base "C". If the 1st position of the sequence was "T", the score was 17.6, or it was 0. If the 3rd position of the sequence was "T" and "C", the score was accumulated by 17.6 and 5.8, respectively, or by 0. If the 4th position of the sequence was "G" and "A", the score was accumulated by 17.6 and 5.8, respectively, or by 0. If the 5th position of the sequence was "G", the score was accumulated by 17.6, or by 0. If the 6th position of the sequence was "G", the score was accumulated by 17.6, or by 0. If the 9th position of the sequence was "T" and "A", the score was accumulated by 12 and 5.8, respectively, or by 0.

vi) The sequences obtained in (3) were traversed (win=4, with a sequence length of 12 bp) and scored based on XXTCTGGGTTXX (X=A, T, C, G), and the 4th position of the sequence must be the base "C" and the 5th position must be the base "T". If the 10th position of the sequence was "T", the score was 17.6, or it was 0. If the 9th position of the sequence was "T" and "C", the score was accumulated by 17.6 and 5.8, respectively, or by 0. If the 8th position of the sequence was "G" and "A", the score was accumulated by 17.6 and 5.8, respectively, or by 0. If the 7th position of the sequence was "G", the score was accumulated by 17.6, or by 0. If the 6th position of the sequence was "G", the score was accumulated by 17.6, or by 0. If the 3rd position of the sequence was "T" and "A", the score was accumulated by 12 and 5.8, respectively, or by 0.

(4) Sorting according to the sequence score from high to low.

By taking EGFP protein as an example, the nuclease recognition site in the nucleotide sequence encoding EGFP protein was determined through the following steps.

i) EGFP nucleotide sequence seq1 (SEQ ID NO: 1) was translated into amino acid sequence seq 2 (SEQ ID NO: 2).

ii) A slide window was performed: (a) splitting the seq2 sequence with a step of 1 (step=1) and a window length of 3 to obtain amino acid fragments with a length of three amino acids, randomly recombining different codons corresponding to each amino acid fragment to obtain possible base sequences corresponding to all amino acid fragments by exhaustion, and constructing a codon sequence set; and (b) splitting the seq2 sequence with a step of 1 (step=1) and a window length of 4 to obtain amino acid fragments with a length of 4 amino acids, randomly recombining different codons corresponding to each amino acid fragment, to obtain possible base sequences corresponding to all amino acid fragments by exhaustion, and adding the corresponding base sequences into the constructed codon sequence set above.

Illustratively, the seq2 sequence is split with a step of 1 and a window length of 3 amino acids, to obtain the amino acid fragments shown below:

MVS,

VSK,

SKG,

KGE,

GEE,

. . .

LYK,

YK*;

where the above " . . . " represents the amino acid fragments between GEE and LYK obtained by successively splitting the seq2 sequence with a step of 1 and a window length of 3 amino acids, and the "*" stands for a stop codon.

The seq2 sequence was split with a step of 1 and a window length of 4 amino acids, to obtain the amino acid fragments shown below:

MVSK, (SEQ ID NO: 60)

VSKG, (SEQ ID NO: 61)

SKGE, (SEQ ID NO: 62)

. . .

ELYK, (SEQ ID NO: 63)

LYK*;

where the above " . . . " represents the amino acid fragments between SKGE and ELYK obtained by successively splitting the seq2 sequence with a step of 1 and a window length of 4 amino acids, and the "*" stands for a stop codon.

iii) The codon sequence set constructed in (2) were tranversed, scoring was performed by taking TTGGGTCTX, XTTGGGTCT, XXTTGGGTCTXX, TCTGGGTTX, XTTGGTTT and XXTCTGGGTTXX as target motifs, which were used as the matching values of codon sequences with the target motif; and the sequence scores were sorted from high to low, as shown in Table 1, where the " . . . " represents the traversed codon sequences in the codon sequence set and corresponding matching values.

TABLE 1

| seq | score | SEQ ID NO: |
|---|---|---|
| XXTTGGGTCTXX | | SEQ ID NO: 64 |
| TTTTCGGTCTCT | 82.4 | SEQ ID NO: 65 |
| ATTTTGGTCGAG | 76.2 | SEQ ID NO: 66 |
| ACTTTGGTCAAT | 76.2 | SEQ ID NO: 67 |
| GGTTCGGTCCAG | 76.2 | SEQ ID NO: 68 |
| TTTTCGGTCAGT | 76.2 | SEQ ID NO: 69 |
| ACTGGGTCGTT | 76.2 | SEQ ID NO: 70 |
| TATGGGGTCCAG | 76.2 | SEQ ID NO: 71 |
| . . . | . . . | |
| XTTGGGTCT | | |
| GATGGGTCT | 82 | |
| GATGGGTCG | 76.2 | |
| GATGGGTCC | 76.2 | |
| GATGGGTCA | 76.2 | |
| . . . | . . . | |
| TTGGGTCTX | | |
| TTGGGTCAT | 93.8 | |
| TTAGGTCAT | 82 | |
| CTGGGTCAT | 76.2 | |
| . . . | . . . | |
| XXTCTGGGTTXX | | SEQ ID NO: 72 |
| ATTCTGGGTCAT | 82 | SEQ ID NO: 73 |
| ACTCTGGGTATG | 82 | SEQ ID NO: 74 |
| ACGCTGGGTATG | 76.2 | SEQ ID NO: 75 |
| ATCCTGGGTCAT | 76.2 | SEQ ID NO: 76 |
| ACCCTGGGTATG | 76.2 | SEQ ID NO: 77 |
| ATACTGGGTCAT | 76.2 | SEQ ID NO: 78 |
| ACACTGGGTATG | 76.2 | SEQ ID NO: 79 |
| . . . | . . . | |
| XTCTGGGTT | | |
| ATCTTGGTT | 82 | |
| TTCTCGGTT | 82 | |
| GGCTCGGTT | 76.2 | |
| ACCTTGGTT | 76.2 | |
| . . . | . . . | |
| TCTGGGTTX | | |
| TCTGCGTTG | 82 | |
| GCTGGGATT | 76.2 | |
| CCTGTGTTG | 76.2 | |
| ACTGGGGTT | 76.2 | |
| . . . | . . . | | iv) The target codon sequence was obtained according to the calculation results of matching values in step (3), wherein the coding region sequence containing the target codon sequence was the target coding region sequence.

Example 3: In Vitro Synthesis of Circular mRNA Encoding eGFP

This example provides a method for preparing a circular mRNA capable of expressing eGFP by the coding region sequence of eGFP containing ribozyme recognition site screened by the present disclosure.

(1) Screening of eGFP Gene Truncation Site and Plasmid Construction

DGS, the amino acid unit to be optimized obtained by the method provided in Example 1-2, was codon-optimized to GAT GGA TCA (ribozyme recognition site sequence) and truncated by TC (effective base pair) to form a structure in the form of T4td intron fragment II-eGFP truncated fragment II-ev29-eGFP truncated fragment I-T4td intron fragment I, and the amino acids and nucleotide sequences involved in this example were shown in Table 2 below.

TABLE 2

| | SEQ ID NO: |
|---|---|
| eGFP protein sequence: | SEQ ID NO: 3 |
| Intron fragment II | SEQ ID NO: 4 |
| Intron fragment I | SEQ ID NO: 5 |
| Ev29 sequence | SEQ ID NO: 10 |
| Untruncated eGFP sequence | SEQ ID NO: 11 |
| eGFP truncated fragment I sequence | SEQ ID NO: 12 |
| eGFP truncated fragment II sequence | SEQ ID NO: 13 |

Plasmid synthesis and cloning under this architecture was commissioned to Suzhou GENEWIZ, from Azenta Life Sciences Suzhou, China. The resultant gene fragment was ligated to pUC57 vector. The resultant plasmid was as follows: pUC57-EV29-eGFP (SEQ ID NO: 14).

(2) Preparation of Linear Plasmid Template

1) Plasmid Extraction i) The stab cultured bacteria custom-synthesized were activated under conditions of 37° C./220 rpm/3-4 h.

ii) The activated bacterial solution was taken for amplification culture under culture conditions of 37° C./220 rpm/overnight.

iii) The plasmids were extracted (with TIANGEN® EndoFree Mini Plasmid Kit II), and then the OD value thereof was measured.

2) Plasmid Enzyme Digestion

The plasmid prepared in the above step 1) was digested by XbaI single enzyme digestion method, and the digestion system was shown in the following table:

TABLE 3

| Reagent | Volume |
|---|---|
| Plasmid | 10 μg |
| Enzyme (1000 units) | 5 μL |
| 10 × cutsmart buffer | 50 μL |
| Nuclease free, H$_2$O | Total 500 μL |

Enzyme digestion was carried out at 37° C. overnight. The enzyme digestion products were recovered by universal DNA gel recovery kit (Universal DNA Purification Kit, TIANGEN BIOTECH CO., LTD.), and then the OD value thereof was measured. After that, the restriction enzyme products were identified by 1% agarose gel electrophoresis. The purified linear plasmid template was used for in vitro transcription.

(3) In Vitro Transcription for Preparing Linear mRNA

1) In Vitro Transcription mRNA was synthesized by T7 in vitro transcription kit (APExBIO T7 High Yield RNA Synthesis Kit), and the transcription system was shown in the following table.

TABLE 4

| Reagent | Volume |
|---|---|
| 10 × Reaction Buffer | 2 μL |
| ATP (20 mM) | 2 μL |
| CTP (20 mM) | 2 μL |
| IKA (20 mM) | 2 μL |
| GTP (20 mM) | 2 μL |
| Linearized DNA template | 1 μg |
| T7 RNA Polymerase Mix | 2 μL |
| RNA Nuclease free, H$_2$O | Total 20 μL |

The resultant was incubated at 37° C. for 2.5 h. Then, the entire product was incubated for 15 min at 37° C. to digesting the linearized DNA template by DNase I.

2) Purification of Linear mRNA

The transcript obtained from step 1) above was purified by silica-based membrane technology in the form of a spin column (Thermo, Gene Jet RNA Purification Kit), and then the OD value thereof was measured. Further, the RNA size was identified by 1% denaturing agarose gel electrophoresis.

3) Purification of Linear mRNA

The transcript obtained from the above step 1) was purified by silica-based membrane technology in the form of a spin column (Thermo, Gene Jet RNA Purification Kit), and then the OD value thereof was measured. Further, the RNA size was identified by 1% denaturing agarose gel electrophoresis.

The method for preparing 1% denaturing agarose gel includes:

1) 1 g of agarose was weighed into 72 mL of nuclease-free H$_2$O and heated until dissolved in a microwave oven.

2) After the above agarose was cooled to 55-60° C., 0.1% gel red, 10 mL of 10×MOPS, and 18 mL of formaldehyde were added therein in the fume hood. Then, pouring gel was carried out.

3) The procedure of denaturing agarose gel electrophoresis includes: the sample RNA and 2× Loading buffer were taken in equal volume, and denaturated at 65-70° C. for 5 to 10 min. The sample was loaded and electrophoresed at 100 V/30 min, and then photographed by gel imaging system.

(4) Circularization of mRNA

1) Circularization Reagent:

GTP Buffer: 50 mM Tris-HCl, 10 mM MgCl$_2$, 1 mM DTT, about pH 7.5.

2) Circularization System and Conditions:

TABLE 5

| Solution | Volume |
|---|---|
| mRNA | 25 μg mRNA |
| GTP solution (20 mM) | 50 μL |
| GTP buffer | up to 500 μL |

The above solution was heated at 55° C. for 15 min and then placed on ice, the circularized RNA products were purified by silica-based membrane technology in the form of a spin column (Thermo, Gene Jet RNA Purification Kit), and then the OD value thereof was measured. Further, the RNA size was identified by 1% denaturing agarose gel electrophoresis.

3) Identification of Circular RNA by 1% Denaturing Agarose Gel

Reagent preparation: 1 g agarose powder was added into 72 mL of nuclease-free water and heated until dissolved, then 10 mL of 10×MOPS buffer solution was added. Then 18 mL of fresh 37% formaldehyde was added in the fume hood and mixed thoroughly, and the gel was poured into the tank.

mRNA detection: About 500 ng of mRNA solution was taken for mixing with 2×RNA loading buffer in equal volume, followed by heating at 65° C. for 5 min. Further, agarose gel detection was carried out.

Experimental Results:

TABLE 6

Figure 18:
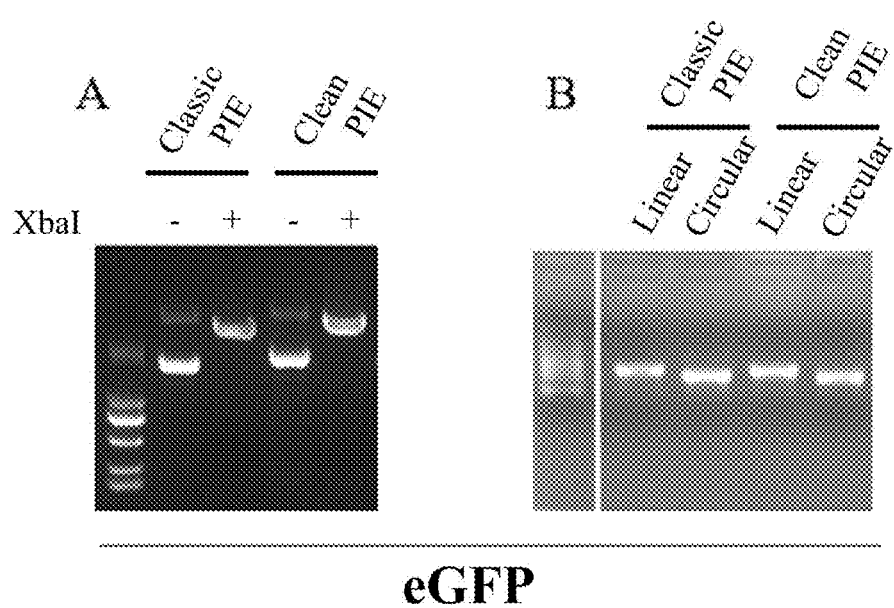
FIG. 18 shows detection results of agarose gel electrophoresis of the digested products (A) of the plasmids used for the preparation of circular mRNA by using a classic PIE system and a Clean PIE system of the present disclosure respectively, and that of the circularized products (B).

| | PLASMID-1 | | ENZYME CUT | | TRANSCRIPTION | | DNASEI DIGEST | | CIRCULIZATION | |
|---|---|---|---|---|---|---|---|---|---|---|
| | Con. (ng/μL) | Vol. | Con. (ng/μL) | Vol. | Con. (ng/μL) | Vol. | Con. (ng/μL) | Vol. | Con. (ng/μL) | Vol. |
| Classic PIE | 313 | 105 μL | 162.2 | 50 μL | 2372 | 70 μL | 2007.5 | 55 μL | 248 | 35 μL |
| EGFP (Clean PIE) of the present disclosure | 329 | 105 μL | 128.8 | 50 μL | 3992 | 70 μL | 1725.3 | 55 μL | 269.2 | 35 μL | classic FIG. 18 shows detection results of agarose gel electrophoresis of the digested products (A) of the plasmids used for the preparation of circular mRNA by using a classic PIE system and a Clean PIE system of the present disclosure respectively, and that of the circularized products (B).

The above results showed that compared with the classic PIE system, the circularization process and technology of preparing circular RNAs using the Clean PIE system in the present disclosure involved no additional changes, showing obvious circularization effect. The circularization efficiency using the Clean PIE system was found similar to that using the classic PIE system through agarose gel electrophoresis, with no obvious difference found.

Example 4: Verification of In Vitro Expression of Circular mRNAs Synthesized In Vitro by the Method of the Present Disclosure In this example, the circular mRNAs prepared in Example 3 were delivered into 293T cells, and the expression in 293T cells of the circular mRNAs synthesized in vitro by the present method was detected, with the following specific process:

(1) Cell Culture 293T cells were inoculated into DMEM high-sugar medium containing 10% fetal bovine serum and 1% penicillin-streptomycin solution, and cultured in an incubator containing 5% $CO_2$ at 37° C. Cells were subcultured every 2 to 3 days.

(2) Cell Transfection

Before transfection, 293T cells were inoculated into a 24-well plate with $1×10^5$ cells/well, and cultured in an incubator containing 5% $CO_2$ at 37° C. After the cells reached 70-90% confluence, mRNAs were transfected into 293T cells by Lipofectamine MessengerMax (Invitrogen) transfection reagent at 500 ng/well, according to the following specific process:

1) Messenger MAX™ Reagent was diluted with a dilution ratio shown in the following table.

TABLE 7

| Reagent | Volume/well |
|---|---|
| MEM serum-free medium | 25 μL |
| MessengerMAX ™ Reagent | 0.75 μL |

After diluting and mixing, the solution was allowed to stand at room temperature for incubating for 10 min.

2) mRNAs were diluted with a dilution ratio shown in the following table:

TABLE 8

| Reagent | Volume/well |
|---|---|
| mRNA | 1 μg |
| MEM serum-free medium | up to 25 μL |

3) The mixed and diluted Messenger MAX™ Reagent and mRNA (1:1) as shown in the following table was taken.

TABLE 9

| Reagent | Volume/well |
|---|---|
| Diluted MessengerMAX ™ Reagent | 25 μL |
| Diluted mRNA | 25 μL |

After diluting and mixing, the solution was allowed to stand at room temperature for incubating for 5 min.

4) 50 μL of the above mixture was taken up, and slowly added into a 24-well plate adhering to the wall, then incubated in an incubator containing 5% $CO_2$ at 37° C.

(3) Protein Expression Detection:

1) Fluorescence observation of cells: 24 hours after transfection, the expression of EGFP was observed in 293T cells under a 200× fluorescence microscope.

2) Detecting the average fluorescence intensity of cells by flow cytometry: the average fluorescence intensity of 293T cells 24 hours after transfection was detected by flow cytometry.

FIGS. 19A and 19B shows the detection results of in vitro expression level of circular mRNAs prepared by the classic PIE system and the Clean system of the present disclosure, where A: the observation results of fluorescence microscope, and B: the detection results of flow cytometry.

The results in FIGS. 19A and 19B showed as follows. The present disclosure unexpectedly found that compared with the circular mRNAs prepared by classic PIE circularization method, the cellular fluorescence of the circular mRNAs prepared by Clean PIE of the present disclosure was strongly enhanced in 293T transfected cells, indicating that the circular mRNAs prepared by Clean PIE of the present disclosure allowed for improved stability of the circular mRNAs in cells. Thus no substantial immunogenicity is occurred, because no additional exon sequences were introduced. Meanwhile, the flow cytometry data also showed that in vitro expression level of the circular mRNAs prepared by Clean PIE of the present disclosure was unexpectedly higher than that of the circular mRNAs prepared by classic PIE. In general, the above results indicated that the Clean PIE system of the present disclosure can improve the expression level of circular mRNAs on the basis of obtaining more accurate circular mRNAs.

Example 5: Application of Clean PIE System for Different Proteins

In this example, many circularization applications for a variety of other different proteins were prepared by the Clean PIE system. The coding region sequences involved in the present disclosure included spCas9, firefly Luciferase, IL12, and FLAG-con1-SPOP167-274, as follows:

1) DGS, the amino acid unit to be optimized of spCas9 obtained by the method provided in Examples 1-2, was codon-optimized to GAT GGA TCA (ribozyme recognition site sequence) and truncated by TC (effective base pair) site to form a structure in the form of T4td intron fragment II-spCas9 truncated fragment II-ev29-spCas9 truncated fragment I-T4td intron fragment I;

2) LRS, the amino acid unit to be optimized of firefly Luciferase obtained by the method provided in Examples 1-2, was codon-optimized to CTT AGG TCT (ribozyme recognition site sequence) and truncated by TC (effective base pair) site to form a structure in the form of T4td intron fragment II-fLUC truncated fragment II-ev29-fLUC truncated fragment I-T4td intron fragment I;

3) LGS, the amino acid unit to be optimized of IL12 obtained by the method provided in Examples 1-2, was codon-optimized to CTT GGG TCT (ribozyme recognition site sequence) and truncated by TC (effective base pair) site to form a structure in the form of T4td intron fragment II-IL12 truncated fragment II-ev29-IL12 truncated fragment I-T4td intron fragment I;

4) LGP, the amino acid unit to be optimized of FLAG-con1-SPOP167-274 obtained by the method provided in Examples 1-2, was codon-optimized to TTG GGT CCT (ribozyme recognition site sequence) and truncated by TC (effective base pair) site to form a structure in the form of T4td intron fragment II-FLAG-con1-SPOP167-274 truncated fragment II-ev29-FLAG-con1-SPOP167-274S truncated fragment I-T4td intron fragment I.

Circular mRNAs expressing spCas9, firefly Luciferase, IL12 and FLAG-con1-SPOP167-274 were prepared, respectively, by the experimental method in Example 3, and the sequences involved in this example were shown in the following table.

TABLE 10

| | SEQ ID NO: |
|---|---|
| spCas9 truncated fragment I | SEQ ID NO: 15 |
| spCas9 truncated fragment II | SEQ ID NO: 16 |
| fLUC truncated fragment I | SEQ ID NO: 17 |
| fLUC truncated fragment II | SEQ ID NO: 18 |
| IL12 truncated fragment I | SEQ ID NO: 19 |
| IL12 truncated fragment II | SEQ ID NO: 20 |
| FLAG-con1-SPOP167-274 truncated fragment I | SEQ ID NO: 21 |
| FLAG-con1-SPOP167-274 truncated fragment II | SEQ ID NO: 22 |

Figure 20:
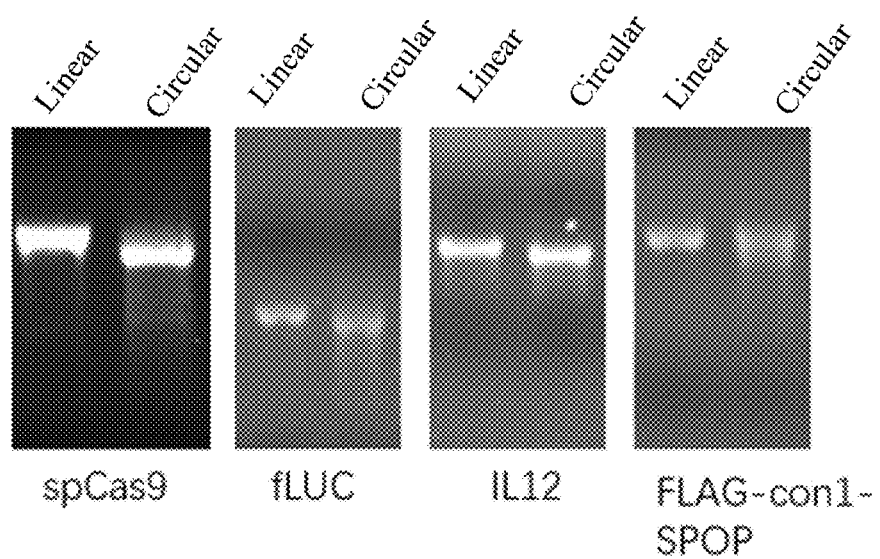
FIG. 20 shows detection results of agarose gel electrophoresis of circular mRNAs expressing different proteins prepared by circularization of a Clean PIE system.

FIG. 20 showed the detection results of agarose gel electrophoresis of circular mRNAs expressing different proteins prepared by circularization of Clean PIE. The experimental results showed that as found from circularization of different proteins (spCas9, firefly Luciferase, IL12, and FLAG-con1-SPOP167-274), after the ribozyme recognition site sequence was obtained by optimization in different proteins, the proteins using the Clean PIE circularization system of the present disclosure each showed difference in their migration rates in agarose gel after circularization. Thus, the results demonstrated that the coding sequences of all proteins can be effectively circularized. In general, the above results indicated that the method provided in the present disclosure can be effectively applied between proteins with different sequences, exhibiting good universality and compatibility, and can be used as a novel macromolecule (≥1000 bp) circularization method.

Example 6: Analysis of Applicability of Clean PIE System

In this example, the availability of the Clean PIE system of the present disclosure in the genes of *Escherichia coli* genome was verified and analyzed by way of bioinformatics. The results indicated that the method of searching for the target circularization sequence (the sequence containing ribozyme recognition site) by the present disclosure has universal applicability.

By taking T4td PIE system as an example: bioinformatics evaluation of genes over 1000 bp and 500 bp in the genome sequence of *Escherichia coli* was performed to screen the effective circularization sequences (score ≥70).

Figure 21:
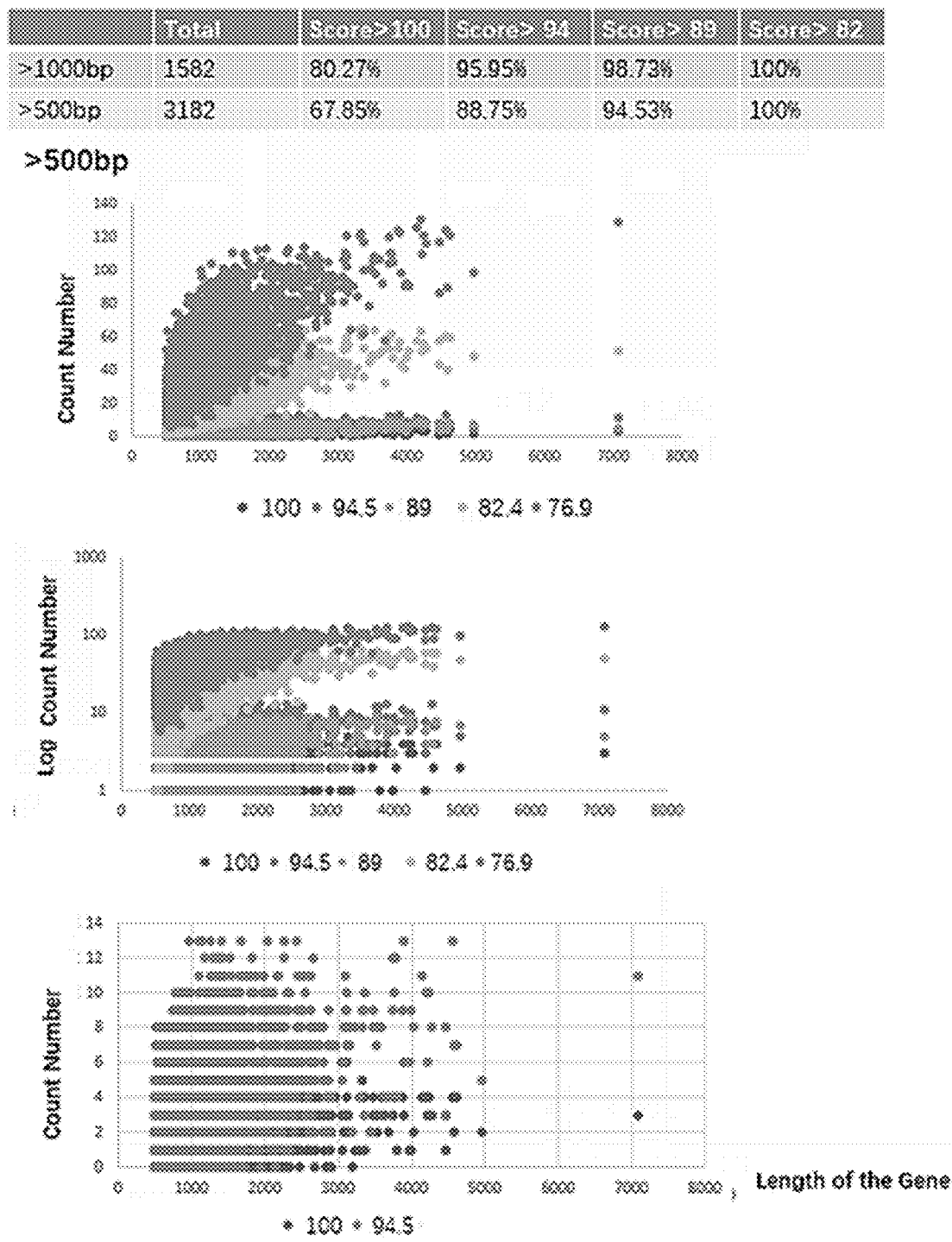
FIG. 21 shows evaluation results of scoring a matching value for genes over 1000 bp and 500 bp in the genome of *Escherichia coli*.

FIG. 21 shows the evaluation results of scoring the matching values for genes over 1000 bp and 500 bp in the genome of *Escherichia coli*. The results showed as follows.

By placing the genes of *Escherichia coli* genome over 1000 bp and 500 bp into the screening system, and performing evaluation using the matching value calculation module, it was found that the probability of finding the target circularization sequence with a score of 82 or more in the genes over 500 bp reached 100%. In addition, this probability can be further improved by combining E1E2 sequences of different Group I introns for the coding gene. That is, the most suitable intron and its corresponding E1E2 sequence were screened by the matching value calculation module as the circularization site (ribozyme recognition site) of circular mRNA.

Example 7: RNaseR Validation of Circularization

In this example, the feasibility of the circularization method of the present disclosure was verified by digesting linear and circular mRNAs. Specifically, as compared with linear RNAs, circular RNAs have better tolerance to RNaseR, thus the sequence circularization can be verified by comparing the tolerance to RNaseR of linear mRNAs and circular mRNAs circularized by Clean PIE.

On the basis of Example 3, the linear and circular mRNAs derived from classic PIE system and Clean PIE system, respectively, were digested by RNase, which was purchased from MClab with ITEM NO. RNASR-100, with the RNaseR digestion system as follows:

TABLE 11

| mRNA | 1 μg |
|---|---|
| RNase R | 1 U |
| 10 × Reaction buffer | 2 μL |
| H$_2$O | Up to 20 μL |

Incubation was carried out at 37° C. for 5 min, and then inactivation was carried out by incubating at 70° C. for 5 min.

Figure 22:
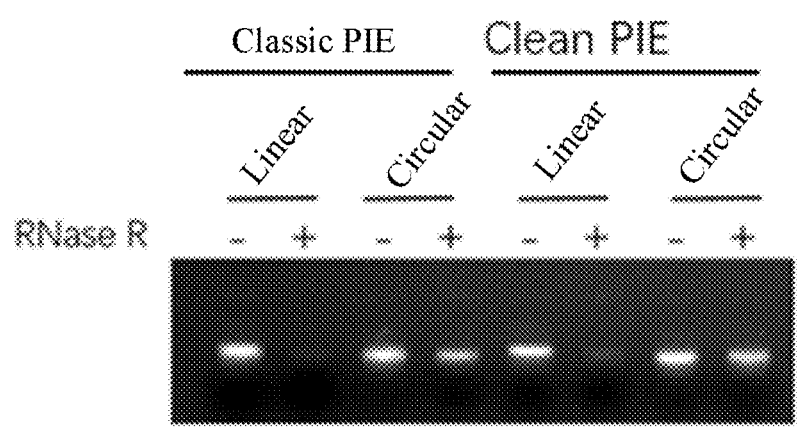
FIG. 22 shows RNaseR digestion of linear and circular mRNAs produced by different PIE systems.

FIG. 22 shows RNaseR digestion of the linear and circular mRNAs produced by different PIE systems. The results showed that circular mRNAs, whether circularized by classic PIE or Clean PIE system, showed good tolerance to RNaseR, indicating that the Clean PIE system can effectively form circular mRNAs.

Example 8: Verification of Clean PIE System Circularization Method by Capillary Electrophoresis In this example, the prepared circular mRNAs were detected by capillary electrophoresis.

The concentration of crude products of circular RNA obtained by circularization in Example 7 were measured by micro-spectrophotometry (Nano-Drop Technologies, Thermo). Then, the crude products were treated by RNA 6000 Assay Kit (Agilent 5067-1511), detected and analyzed by Agilent 2100 automated nucleic acid analyzer. The procedures for the kit and analyzer can be found in Agilent's official website.

Figure 23A:
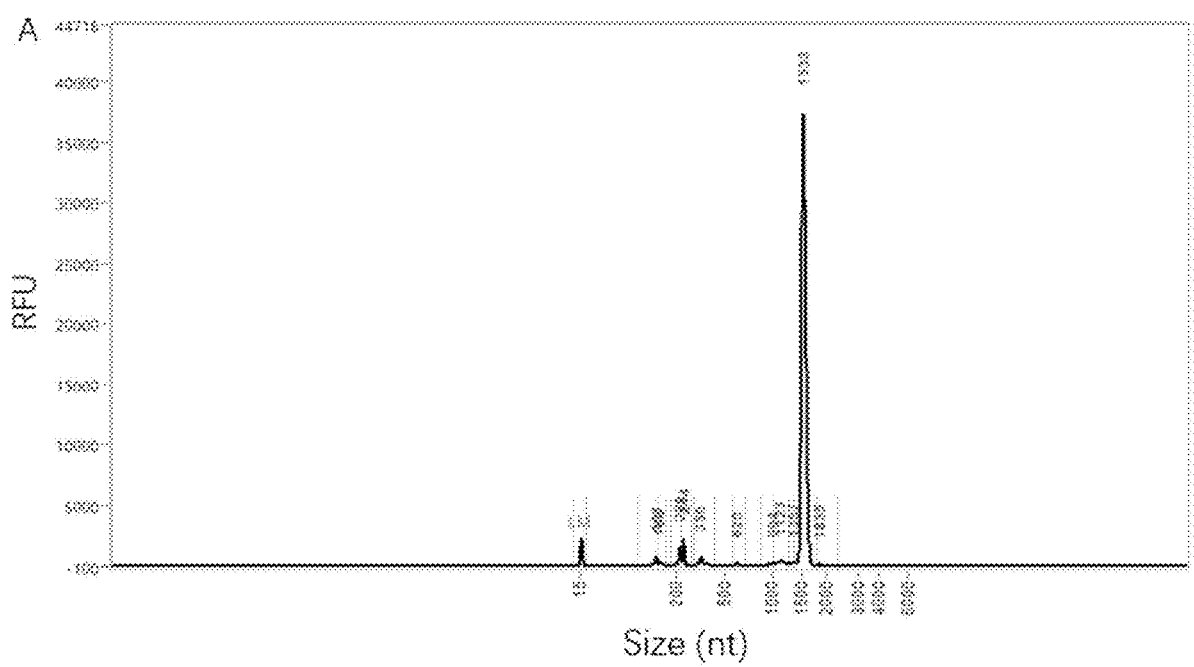
FIGS. 23A through 23C show analysis results of capillary electrophoresis.
Figure 23B:
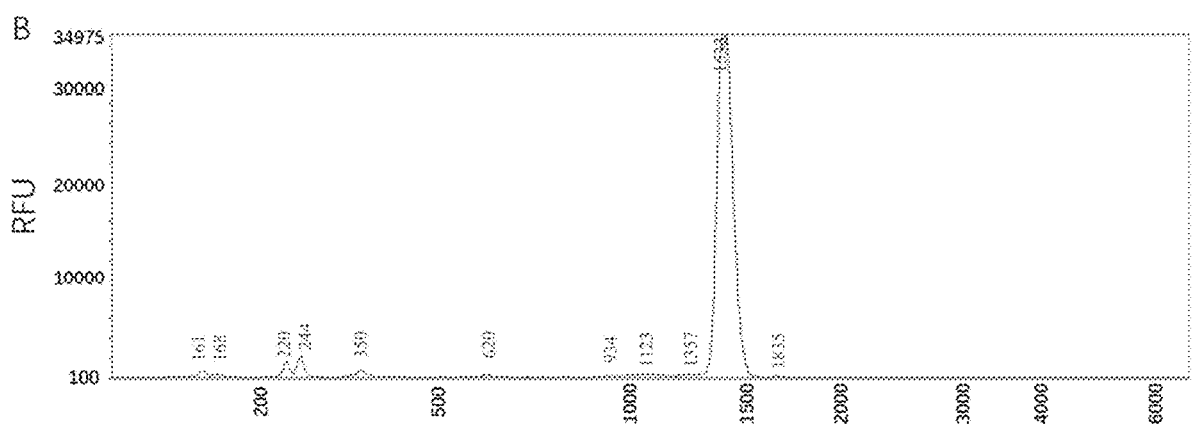
Figure 23C:
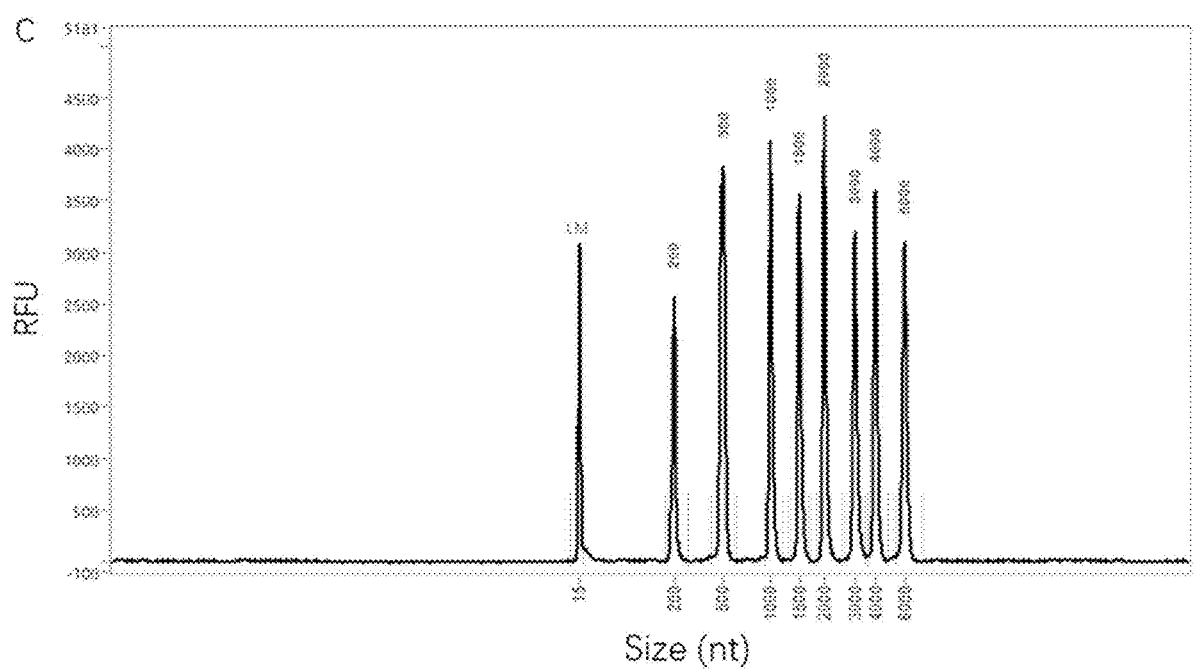

FIGS. 23A through 23C shows the analysis results of capillary electrophoresis. The top figure (FIG. 23A) was the capillary electrophoresis detection pattern of the circular RNA products without RNaseR treatment and HPLC purification, the middle figure (FIG. 23B) was the partial enlargement of the top figure, and the bottom figure (FIG. 23C) was the molecular weight standard. The results showed as follows.

By capillary electrophoresis, the circularized RNA showed single peak, and had two intron peaks at nt-218 and nt-243, and one intron dimer peak at nt-349. The total circular mRNAs accounted for 89.6% (before purification), further indicating that the method of the present disclosure can effectively realize the circularization of circular messenger ribonucleotides.

Example 9: Verification of Sequence Integrity and Sequence Accuracy at Circularization Site (Ribozyme Recognition Site)

In this example, the sequence integrity and accuracy at the circularization site of the circular mRNA circularized by the circularization method of the invention were identified by sequencing after reverse transcription. The primer sequences used in this example were as follows:

```
Fluc-R:
                                     (SEQ ID NO: 23)
TACTTGTCGATCAGGGTGCT Fluc-F:
                                     (SEQ ID NO: 24)
TGGACAGCAAGACCGACTAC IL12-R:
                                     (SEQ ID NO: 25)
CTGCATCAGCTCGTCGATGG IL12-F:
                                     (SEQ ID NO: 26)
TACTACAACAGCAGCTGCAGCA
```

Each of the linear and circular mRNAs of firefly Luciferase (Fluc) and IL12 in Example 5 was reverse transcribed into a first strand cDNA by the reverse transcription kit of Takara Company (RR037B, Takara). By using cDNA as a template, PCR amplification was carried out with specific primers to obtain amplified fragments. The sequence of the actually synthesized circular mRNA was compared with that of the designed circular mRNA by sequencing.

Figure 24:
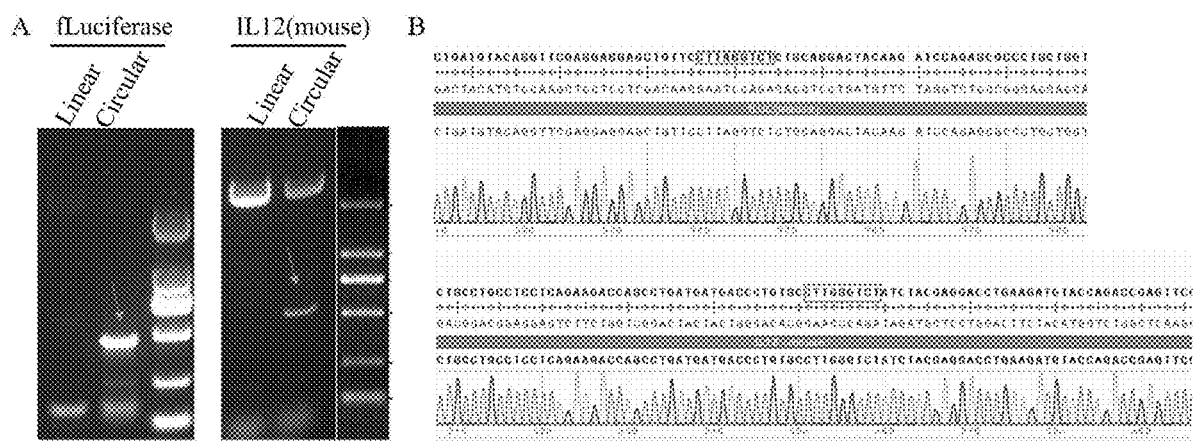
FIGS. 24A and 24B show PCR sequencing analysis results of cDNA after reverse transcription of Fluc and IL12.

FIGS. 24A and 24B shows the analysis results of PCR sequencing of cDNA after reverse transcription of Fluc and IL12, where A illustrates the agarose gel electrophoresis results of PCR amplified fragments after reverse transcription of linear and circular mRNAs, and B illustrates the sequencing results after reverse transcription of circular mRNAs expressing Fluc and IL12. The red arrow represents the specific amplification band of circular mRNA, and the sequences framed in the red box are the circularization sites of Fluc and IL12.

The experimental results showed that the specific amplification band was not present in linear mRNA group but appeared in circular mRNA group. The specific band was excised from the gel. The cDNA was recovered from the gel, and then subjected to Sanger sequencing after purification. The sequencing results showed that the PCR band was consistent with the expected band, and there was no additional base insertion or deletion near the circularization site. This demonstrated that Luciferase and IL12 have been accurately circularized.

Example 10: Analysis and Verification of Expression of Uncircularized Linear Part This example verified that the linear RNAs produced by the Clean PIE system of the present disclosure cannot express any protein, indicating that the linear mRNAs in the present disclosure cannot produce any nonspecific translated protein before circularization.

In this example, according to the method of Example 5, the linear and circular mRNAs of FLAG-con1-SPOP in the classic PIE system as well as the linear and circular mRNAs in the Clean PIE system were transfected into 293T cells. After 24 hours, the cells were collected, lysed, and subjected to western blotting detection. Due to the presence of FLAG label after the promoter, the expressed protein can be detected by an anti-FLAG antibody.

Figure 25A:
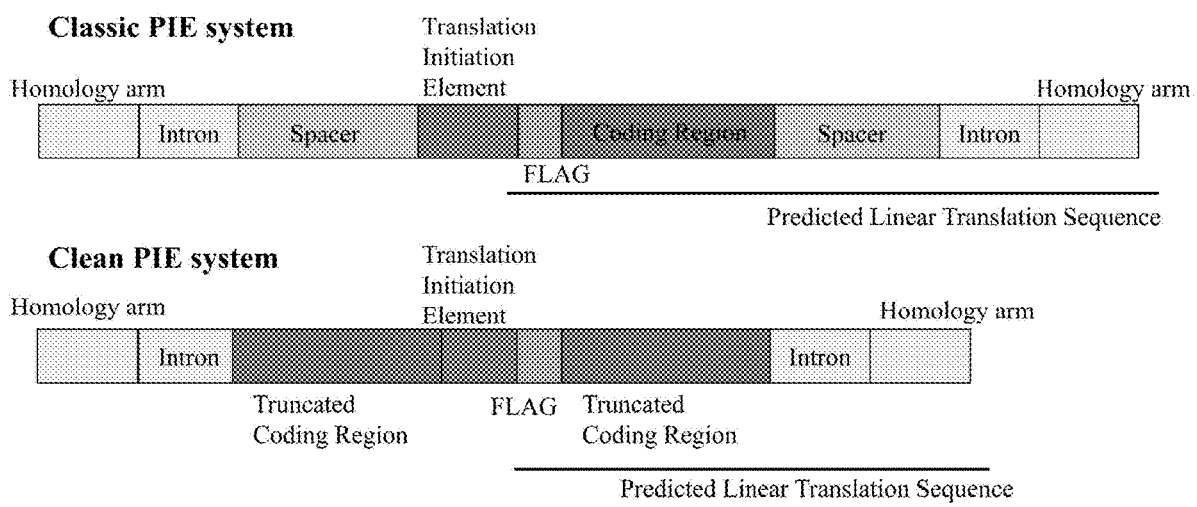
FIGS. 25A and 25B shows expression detection results of uncircularized linear mRNAs for preparing circular mRNAs respectively in a classic PIE system and a Clean PIE system of the present disclosure, and that of circularized circular mRNAs; where A shows structures of uncircularized linear mRNAs of the classic PIE system and the Clean PIE system, and B shows protein expression results of the linear mRNAs detected by western blotting.
Figure 25B:
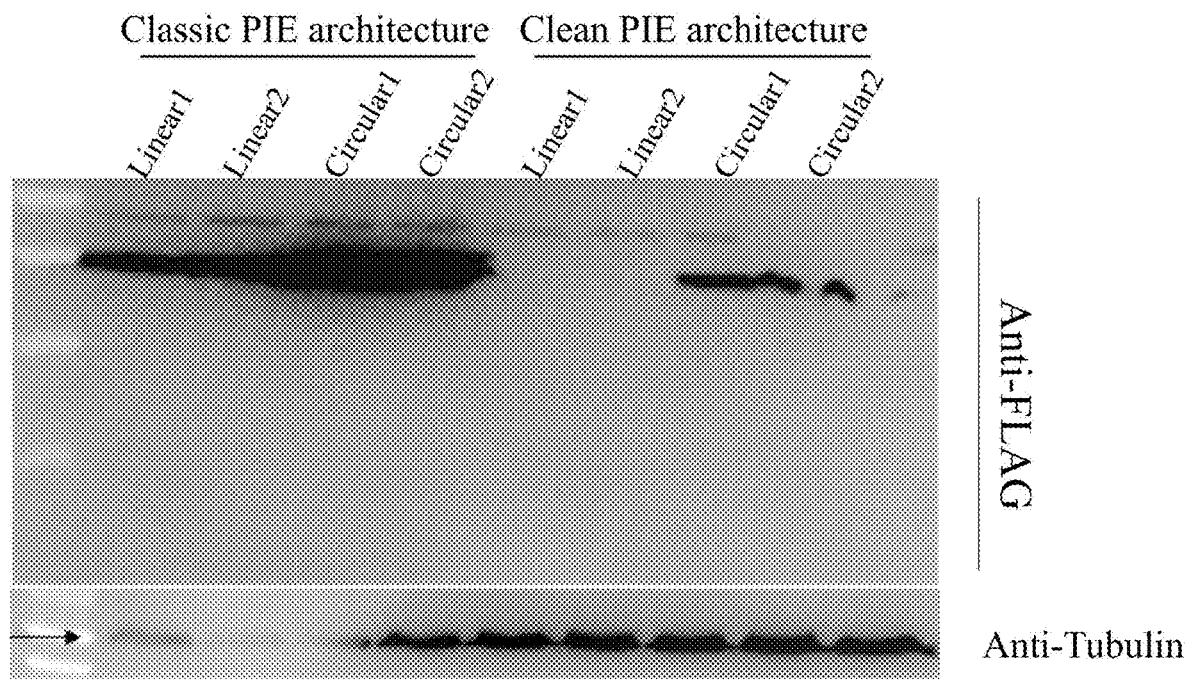

FIGS. 25A and 25B shows the expression detection results of uncircularized linear mRNAs for preparing circular mRNAs of the classic PIE system and Clean PIE system of the present disclosure, and that of circularized circular mRNAs, where FIG. 25A shows the structures of uncircularized linear mRNAs of the classic PIE system and Clean PIE system of the present disclosure, and FIG. 25B shows the protein expression results of linear mRNAs detected by western blotting. The results showed as follows.

Under the classic PIE framework, the uncircularized mRNA can still be expressed, while under the Clean PIE framework, no expression products of uncircularized mRNAs appeared. Circularized circular RNAs from different circularization systems can be expressed, and the difference in expression level of circular mRNAs from different systems is due to different elements in the systems. This example demonstrated that the Clean PIE system of the present disclosure has a high biological safety for preparing circular mRNAs.

Example 11: Translational Regulatory Elements Enhance Expression of Circular mRNAs Through Clean PIE Circularization In this embodiment, an insertion element, specifically, a translational regulatory element, was inserted into the Clean PIE circularization system provided in Example 3, which was ligated to the 5' end of ev29. By adding a translational regulatory element, the expression of circular mRNAs produced by the circularization methods of the present disclosure can be enhanced. And the optimal polyAC length that is favorable to the expression of the encoded protein is obtained through screening.

The Clean PIE circularization system ligating translation regulatory element comprises structure as shown below:

T4td intron fragment II-eGFP truncated fragment II-translational regulatory element (PolyAC)-ev29-eGFP truncated fragment I-T4td intron fragment I.

Wherein, the nucleotide sequence of PolyAC is as shown in SEQ ID NO:1, and the circularized sequence after adding PolyAC is as shown in SEQ ID NO:2.

Circular mRNAs were prepared with the linear eGFP messenger ribonucleotide with translational regulatory expression element, according to the method of Example 3. Then, the circular mRNAs were transfected into 293T cells and the expression of eGFP was measured by flow cytometry, according to the method of Example 4.

Figure 26:
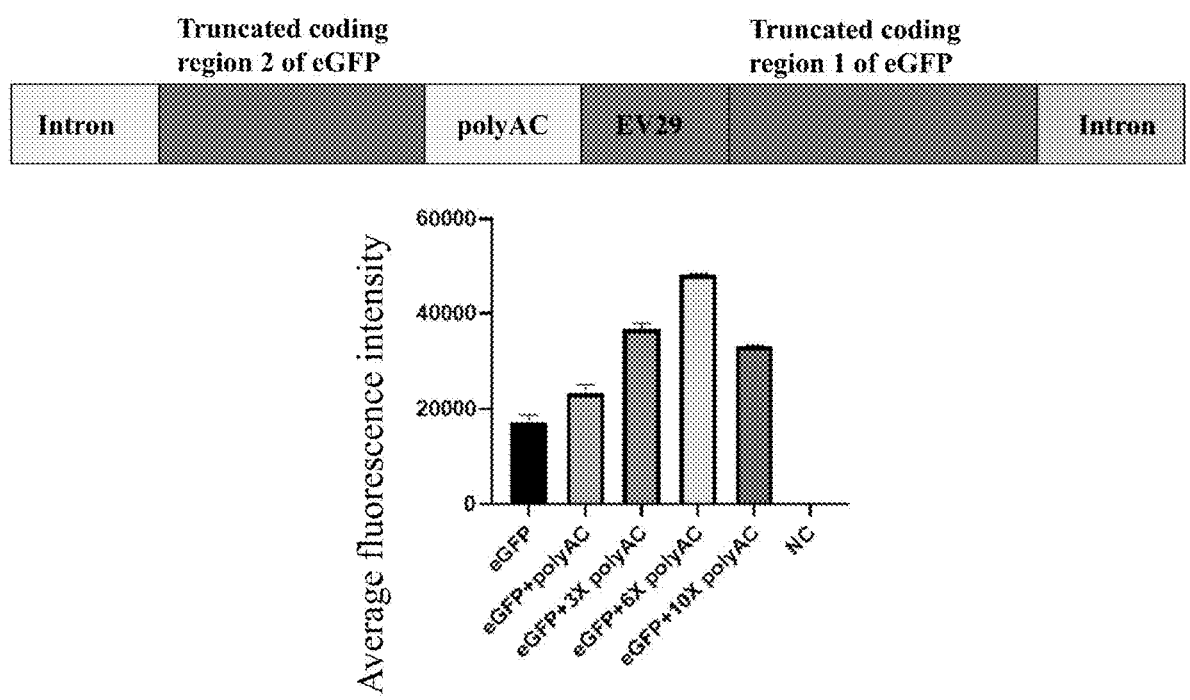
FIG. 26 shows expression detection results of circular mRNAs prepared by a Clean PIE system after inserting a translational regulatory element (polyAC).

FIG. 26 showed the expression detection results of circular mRNAs prepared by a Clean PIE system after inserting a translational regulatory element (polyAC). Result showed as follows.

As the number of inserted translational regulatory elements increases, the expression level of eGFP encoded by circular mRNAs can be significantly increased to some extent. Wherein, adding 6× polyAC achieved the greatest improvement in expression efficiency, while further increasing the length did not significantly improve the expression of the encoded protein (data for 10× polyAC).

Example 12: Regulation of the Tissue-Specific Expression of Circular mRNAs Through Clean PIE Circularization by Translational Regulatory Elements In this example, an insertion element, specifically, a translational regulatory element for regulating specific expression of circular mRNA in organs, was ligated to the Clean PIE circularization system at the 5' end of the IRES element. The Clean PIE system included the following structure, and each element sequence thereof can be referred to Examples 3-5:

T4td intron fragment II-LUC truncated fragment II-translational regulatory element-ev29-LUC truncated fragment I-T4td intron fragment I.

Circular mRNAs as follows were prepared according to the methods of Examples 3 to 4: EV29-LUC-3UTR (sequence set forth in SEQ ID NO: 56), EV29-LUC+1×miR-122 (sequence set forth in SEQ ID NO: 57), and EV29-LUC+3×miR-122 (sequence set forth in SEQ ID NO:58), each was encapsulated in the DLin-MC3-DMA LNP delivery system and prepared by a microfluidic device, to allow the mRNA active components in the aqueous phase to fully mix with four lipids in the organic phase to form a nano-sized circular mRNA-lipid nanoparticle complex with a high encapsulation efficiency. The specific procedure was as follows:

(1) diluting the circular mRNA stock solution to 0.4 mg/mL with citric acid solution at pH 4.0, then weighing four lipids and dissolving them in ethanol solution to give a total lipid concentration of 24.4 mg/mL;

(2) mixing the two phases quickly using a microfluidic device, with a total flow rate of 12 mL/min, aqueous phase (circular mRNA)/organic phase (lipid) (v/v)=3:1;

(3) After the preparation completed, removing ethanol by dialysis or tangential flow, and meanwhile replacing the solution with PBS solution at pH 7.4, to obtain the circular mRNA-lipid nanoparticle complex;

(4) detecting the particle size and polydispersity coefficient (PDI) of the circular mRNA-lipid nanoparticle complex by dynamic light scattering (DLS), and detecting the encapsulation efficiency of circular mRNAs in the complex by Ribogreen.

The mice were administered by tail vein injection, and the expression of Luciferase in mice was determined after 6 hours. Specifically, mice immunized with pUC-EV29-LUC, pUC-EV29-LUC+1×miR-122, and pUC-EV29-LUC+3× miR-122 respectively were intraperitoneally injected with 0.3 mL of luciferase substrate VivoGlo luciferin (In vivo Grade, Promega), and imaged after 8 minutes to observe in vivo distribution and fluorescence intensity of expression.

Figure 27:
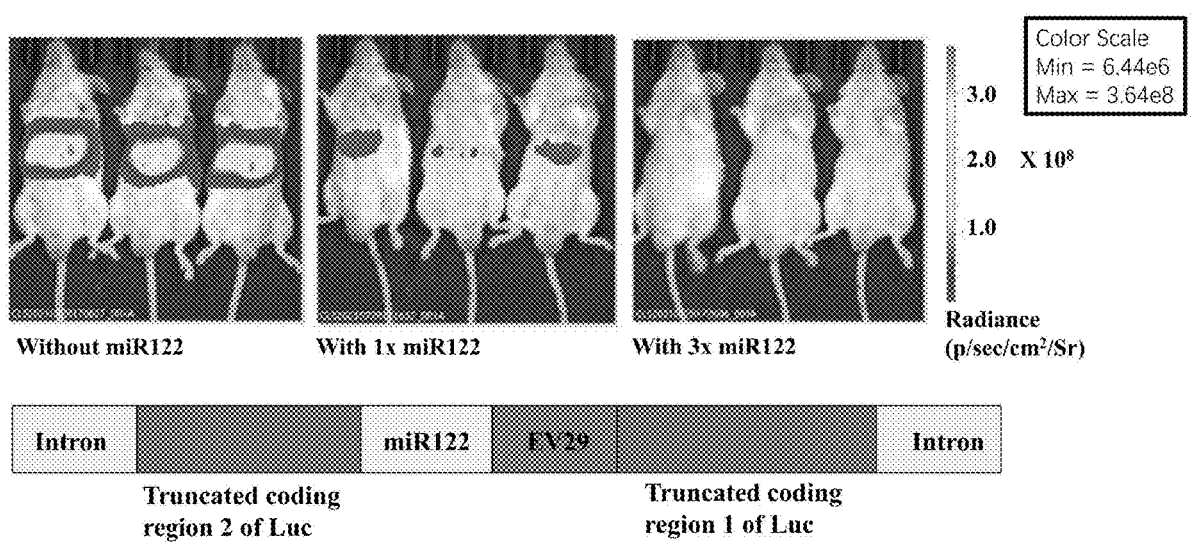
FIGS. 27A and 27B show tissue-specific expression of circular mRNAs obtained by circularization of a Clean PIE system and regulated by a translational regulatory element, where A shows the expression of circular mRNAs with miR122 site injected in mice, and B shows a frame structure of the Clean PIE system with miR122 site.

FIGS. 27A and 27B shows the tissue-specific expression of circular mRNAs obtained by circularization of the Clean PIE system and regulated by the translational regulatory element, where FIG. 27A shows the expression of circular mRNAs with miR122 site injected in mice, and FIG. 27B is the frame structure of Clean PIE system with miR122 site. The experimental results showed as follows.

The luciferase in control group (EV29-luc-3UTR) mice was mainly expressed at intramuscular injection site and in liver. The circular mRNA (EV29-LUC-+1×miR-122) with a single acting site of miR-122 was mainly expressed at the tail vein injection site, and a small expression level in liver was found in individual mice, whereas the circular mRNA (EV29-LUC+3×miR-122) in which three acting sites of miR-122 were added was only expressed at the intramuscular injection site, without detection of any expression in liver. Therefore, the introduction of miR-122 binding site as a translational regulatory element in the Clean PIE system of the present disclosure can effectively avoid the expression of circular mRNAs in liver, and the more the introduced miR-122 sites, the more significant the inhibitory effects on expression in liver.

Example 13: Role of Translational Regulatory Elements in Purification of Circular mRNA In this example, an aptamer was added to the translational regulatory element to purify the circular mRNA. Specifically, as described in the literature (Leppek K, Stoecklin G. An optimized streptavidin-binding RNA aptamer for purification of ribonucleoprotein complexes identifies novel ARE-binding proteins[J]. Nucleic Acids Research, 2014, 42 (2): e13-e13.), four S1m aptamer sequences were added to the translational regulatory elements of the Clean PIE system of the present disclosure, and circularization was carried out according to the method of Example 3. The structure was shown below:

T4td intron fragment II-eGFP truncated fragment II-translational regulatory element (with S1m aptamer added)-ev29-eGFP truncated fragment I-T4td intron fragment I;

S1m sequence:
(SEQ ID NO: 37)
AUGCGGCCGCCGACCAGAAUCAUGCAAGUGCGUAAGAUAGUCGCGGGUCGG CGGCCGCAU;

The circularized circRNA was shown in SEQ ID NO: 59.

In a LoBind tube (Eppendorf) centrifuge tube, Wash Buffer (20 mM Tris-HCl (pH 7.5), 150 mM NaCl, 1.5 mM MgCl2, 2 mM DTT, 2 mM vanadylribonucleosid complex RNase inhibitor (NEB), 1 tablet/10 ml Mini Complete Protease Inhibitors, EDTA-free (Roche)) was used to clean Streptavidin Sepharose High Performance (GEHealthcare)

agarose gel beads. 30 µg of crude products of circular RNAs (Input) were incubated at 37° C. for 10 minutes, then rotary mixed with 100 ul agarose gel magnetic beads as well as 3 uL RNase inhibitors and incubated at 4° C. for 2-3 hours, centrifuged, unbound, and incubated continually at 4° C. for 1 hour in 50 ul of lysis buffer added with 10 mM biotin, and centrifuged to obtain the supernatant as the purified products (biotin elution).

Figure 28:
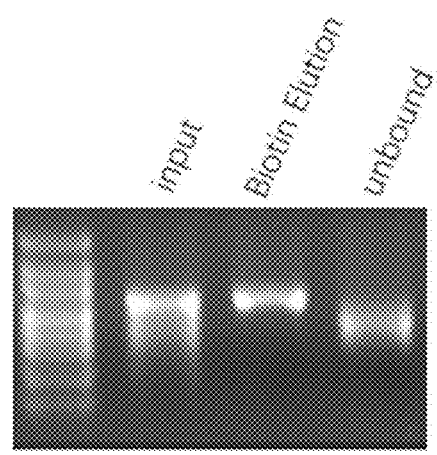
FIG. 28 shows detection results of gel electrophoresis of circular mRNAs purified by S1m RNA aptamer.

FIG. 28 shows the detection results of gel electrophoresis of circular mRNAs purified by S1m RNA aptamer. The circular mRNAs with the aptamer can be separated from the circularization reaction system by streptomycin affinity chromatography, so that the self-splicing intron fragments and other small nucleotide fragment impurities can be removed. "Input" represented the crude products of circularized circRNA by the method of Example 7, "Biotin elution" represented the purified products, and "unbound" represented the magnetic agarose gel bead products unbond to streptomycin.

Example 14: Detection of Immunogenicity of Circularized eGFP

In this example, the expression of corresponding immune factors in A549 cells induced by circular mRNAs was detected, where the circular mRNAs were prepared by *Anabaena* PIE system and the Clean PIE system of the present disclosure as follows.

As provided in Example 3, circular mRNAs prepared by circularization of *Anabaena* PIE system and the Clean PIE system of the present disclosure were digested by RNaseR and purified by HPLC. Then, the purified circular mRNAs were transfected into A549 cells by Lipofectamine Messenger Max (Invitrogen), with the following specific operation procedure.

A549 cells were inoculated into DMEM high-sugar medium containing 10% fetal bovine serum and 1% penicillin-streptomycin solution and cultured in an incubator containing 5% CO2 at 37° C. Cells were subcultured every 2 to 3 days.

(1) Cell Transfection

Before transfection, A549 cells were inoculated into a 24-well plate with $1\times10^5$ cells/well, and cultured in an incubator containing 5% $CO_2$ at 37° C. When the cells reached 70-90% confluence, mRNAs were transfected into A549 cells by Lipofectamine MessengerMax (Invitrogen) transfection reagent at 500 ng/well, with the following specific operations.

1) Messenger MAX™ Reagent was diluted according to a dilution system shown in the following table.

TABLE 12

| Reagent | Volume/well |
| --- | --- |
| MEM serum-free medium | 25 µL |
| Messenger MAX ™ Reagent | 0.75 µL |

After diluting and mixing, the solution was allowed to stand at room temperature for incubating for 10 min.

2) mRNAs were diluted according to a dilution system shown in the following table.

TABLE 13

| Reagent | Volume/well |
| --- | --- |
| mRNA | 1 µg |
| MEM serum-free medium | up to 25 µL |

3) The mixed and diluted Messenger MAX™ Reagent and mRNA (1:1) was taken.

TABLE 14

| Reagent | Volume/well |
| --- | --- |
| Diluted Messenger MAX ™ Reagent | 25 µL |
| Diluted mRNA | 25 µL |

After diluting and mixing, the solution was allowed to stand at room temperature for incubating for 5 min.

(2) 50 µL of the above mixture was taken up, and slowly add into a 24-well plate adhering to the wall, and then incubated in an incubator containing 5% $CO_2$ at 37° C.

(3) Lysing on the cells after 8 hours of expression was performed, and the expression level of immune response protein was verified by fluorescence quantitative PCR.

The primer sequences used by fluorescence quantitative PCR were as follows:

```
IFNb-F:
                                           (SEQ ID NO: 42)
TGGGAGGATTCTGCATTACC

IFNb-R:
                                           (SEQ ID NO: 43)
CAGCATCGCTGGTTGAGA

RIG-1-F:
                                           (SEQ ID NO: 44)
CTCCCGGCACAGAAGTGTAT

RIG-1-R:
                                           (SEQ ID NO: 45)
CTTCCTCTGCCTCTGGTTTG

IFNa-F:
                                           (SEQ ID NO: 46)
CCATCTCTGTCCTCCATGAG

IFNa-R:
                                           (SEQ ID NO: 47)
ATTTCTGCTCTGACAACCTC

PKR-F:
                                           (SEQ ID NO: 48)
TGCAAAATGGGACAGAAAGA

PKR-R:
                                           (SEQ ID NO: 49)
TGATTCAGAAGCGAGTGTGC

MDA5-F:
                                           (SEQ ID NO: 50)
ACCAAATACAGGAGCCATGC

MDA5-R:
                                           (SEQ ID NO: 51)
GCGATTTCCTTCTTTTGCAG

TNFa-F:
                                           (SEQ ID NO: 52)
CGTCTCCTACCAGACCAAGG

TNFa-R:
                                           (SEQ ID NO: 53)
CCAAAGTAGACCTGCCCAGA
```

-continued

IL-6-F:
TACCCCCAGGAGAAGATTCC
(SEQ ID NO: 54)

IL-6-R:
GCCATCTTTGGAAGGTTCAG
(SEQ ID NO: 55)

The circular mRNA sequences prepared by two kinds of PIE systems were shown in the following table.

TABLE 15

| | SEQ ID NO: |
|---|---|
| Circular mRNA sequence expressing eGFP after circularization by Clean PIE system of the present disclosure | SEQ ID NO: 38 |
| Circular mRNA sequence expressing eGFP after circularization by *Anabaena* PIE system | SEQ ID NO: 39 |

Figure 29:
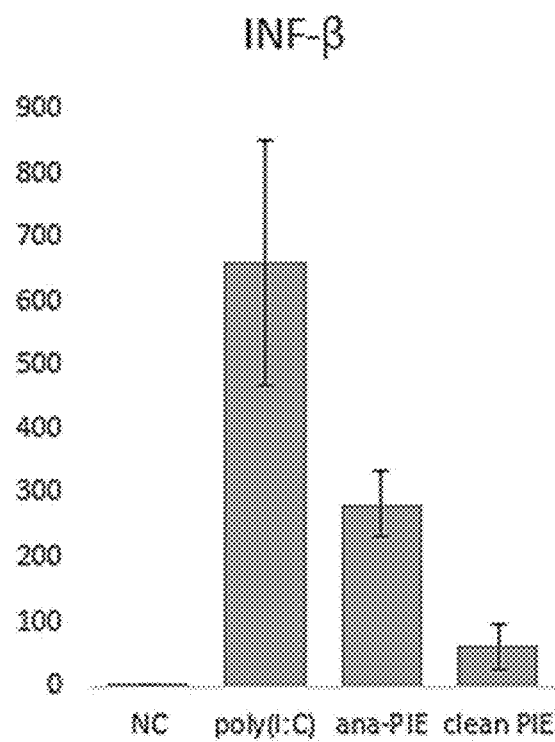
FIG. 29 shows expression of immune factors induced by circular mRNAs prepared by using a Clean PIE system (corresponding to the Clean PIE shown) and *Anabaena* PIE system (corresponding to the ana-PIE shown).

FIG. 29 shows the expression of immune factors induced by circular mRNAs prepared by using Clean PIE system (corresponding to Clean PIE in the figure) and *Anabaena* PIE system (corresponding to ana-PIE in the figure). The results showed as follows.

After ana-PIE underwent detestation by RNase R and purification by HPLC, although INF-β might still lead to immune response, there was a significantly decreased immune response in the circular mRNAs prepared by the circularization system of the present disclosure compared to that by ana-PIE, proving that the circular mRNA with more accurate sequence can reduce the induction of immunogenicity.

Example 15: No Effect on In Vitro Circularization for Circular mRNAs with Deletion of Homology Arms In this example, the effect of adding homology arms to the Clean PIE system of the present disclosure on the circularization efficiency was detected. Specifically, DGS, the amino acid unit to be optimized obtained by the method provided in Examples 1 to 2, was codon-optimized to GAT GGA TCA (ribozyme recognition site sequence) and truncated by TC (effective base pair) to form a structure in the form of T4td intron fragment II-eGFP truncated fragment II-ev29-eGFP truncated fragment I-T4td intron fragment I, while intron sequences with or without homology arms were constructed with the specific structures as follows.

Sequence information involved in this example was shown in the following table.

TABLE 16

| | SEQ ID NO: |
|---|---|
| eGFP protein sequence: | SEQ ID NO: 3 |
| Intron fragment II (with homology arms) | SEQ ID NO: 4 |
| Intron fragment I (with homology arms) | SEQ ID NO: 5 |
| Intron fragment II (without homology arms) | SEQ ID NO: 6 |
| Intron fragment I (with homology arms) | SEQ ID NO: 7 |
| Ev29 sequence | SEQ ID NO: 10 |

Figure 30:
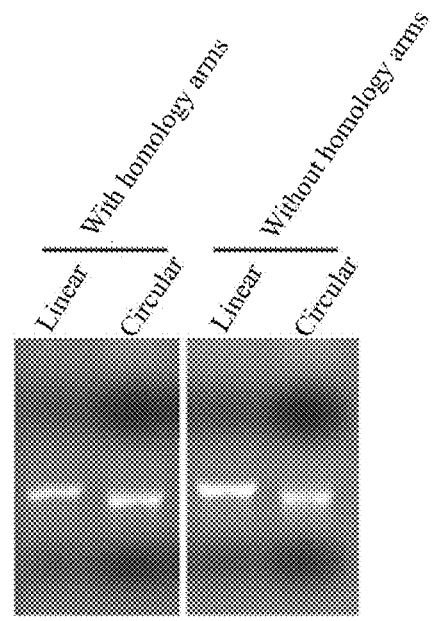
FIG. 30 shows detection results of gel electrophoresis of circular mRNAs prepared by the Clean PIE system with and without homology arms.

The two constructs were transcribed and circularized by the experimental method of Example 3 to obtain their circular mRNAs. The circularization results were detected by denaturing agarose gel electrophoresis. FIG. 30 shows the detection results of gel electrophoresis of circular mRNAs prepared by the Clean PIE system with or without homology arms. The results showed as follows.

Regardless of whether homology arms were included or not in the present Clean PIE system framework, circular mRNAs can realize effective circularization. This result demonstrated that homology arms can be omitted in the circularization system of the present disclosure. The reason for this is that under the frame of the present disclosure, the circularization site (ribozyme recognition site) always divided the coding gene into two parts, and the coding fragment usually did not have a very complicated secondary structure, such benign sequence separated the promoter element from the self-splicing intron sequence, thus forming a unique secondary structure, which was more conducive to the correct folding and approach of intron sequences. As a result, an effective circularization can be achieved without homology arms under the frame of the present disclosure.

Example 16: Validation of Circularization at Circularization Sites with Different Scores This example compared the circularization efficiency of circularization sites (ribozyme recognition sites) with different scores and at different positions in the same protein sequence (IL12 human) obtained by the screening system.

Specifically, DRVF (866, score 93.8), IWS (377, score88), SGS (1021, score 88), GGS (1285, score88) and LGS (211, score 100), the amino acid units to be optimized obtained by the method provided in Examples 1 to 2, were respectively codon-optimized to the ribozyme recognition site sequences as follows: GAT CGG GTC TTT, ATT TGG TCT, TCT GGG TCT, GGT GGG TCT, and CTT GGG TCT, and truncated by TC site to form the following structure:

T4td intron fragment II-IL12 human truncated fragment II-ev29-IL 12 human truncated fragment I-T4td intron fragment I.

TABLE 17

| | SEQ ID NO: |
|---|---|
| IL12 (human, 866 score 93.8) truncated fragment II | SEQ ID NO: 27 |
| IL12 (human, 866 score 93.8) truncated fragment I | SEQ ID NO: 28 |
| IL12 (human, 377 score 88) truncated fragment II | SEQ ID NO: 29 |
| IL12 (human, 377 score 88) truncated fragment I | SEQ ID NO: 30 |
| IL12 (human, 1021 score 88) truncated fragment II | SEQ ID NO: 31 |
| IL12 (human, 1021 score 88) truncated fragment I | SEQ ID NO: 32 |
| IL12 (human, 1285 score 88) truncated fragment II | SEQ ID NO: 33 |
| IL12 (human, 1285 score 88) truncated fragment I | SEQ ID NO: 34 |
| IL12 (human, 211 score 100) truncated fragment II | SEQ ID NO: 35 |
| IL 12 (human, 211 score 100) truncated fragment I | SEQ ID NO: 36 |

Figure 31:
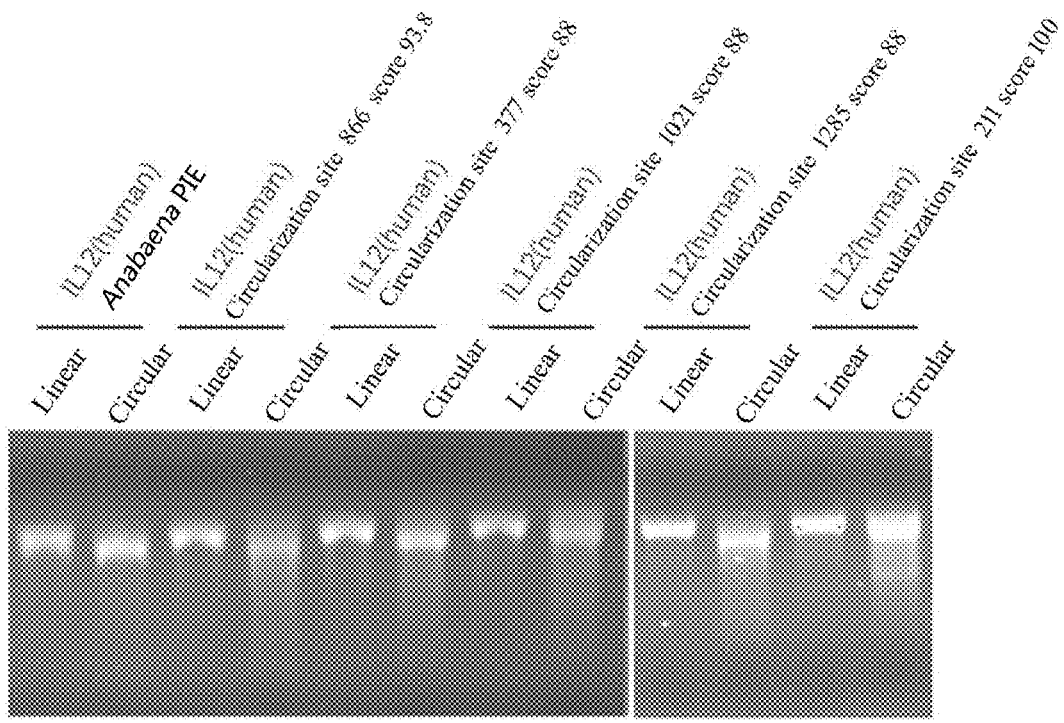
FIG. 31 shows analysis results of agarose gel electrophoresis of circular mRNAs constructed using truncated sequences of coding regions with different scores.

The two constructs were transcribed and circularized by the experimental method of Example 3 to obtain their corresponding circular mRNAs. The structure shown in FIG. 31 was obtained by denaturing agarose gel electrophoresis analysis, and the results showed as follows.

IL12 human truncated at circularization sites with different scores can be circularized, but with different circularization efficiencies. The difference of circularization efficiency may be due to different secondary structures at different open-loop positions. Therefore, it may be deduced that a small score difference of circularization site cannot properly reflect the circularization efficiency. Further evaluation is required in combination with the secondary structure in the sequence.

Example 17: Exploration of the Lowest Score Allowing for Circularization

In this embodiment, the lowest circularization score was determined by verifying circularization of truncated fragments with different scores.

Taking T4td as an example, by comparing the changed sequences at the circularization site (ribozyme recognition site) (TTGGGTCT), the circularization site sequence of eGFP sequence in Examples 6 and 7, was changed to the following base sequences with different scores for verifying circularization:

Score 100 (TTGGGTCT), score 94.2 (TCGGGTCT), score 82.4 (TAGGGTCT, ATGGGTCT), score 64.8 (AAGGGTCT, ATGGCTCT), score 47.2 (AACGGTCT, TTCATTCT), score 29.6 (AACGCTCT, AAACCGTCT, TACCCTCT).

Circularization verification was performed according to the method described in Example 7. To be specific, sequences with scores of 80 or more can be circularized with a circularization efficiency of 50% or more. In addition, the circularization test of sequences with scores of 47.2 and 64.8 showed that not all sequences can be circularized, and some sequences can be circularized but with low circularization efficiency. Further, it was difficult for the sequence with score 29.6 to circularize.

Example 18: Expression of Polypeptides Ligated in Tandem by Linker T2A

In this example, the coding regions of eGFP and firefly Luciferase were ligated in tandem by 2A peptide (T2A) encoded by a linker, and then the expression of those proteins were verified.

Specifically, according to the method of Example 3, a circular mRNA was constructed by using the Clean PIE system containing the following structure, and the circular mRNA capable of expressing eGFP and firefly Luciferase ligated in tandem by T2A was obtained.

Intron fragment II-eGFP truncated fragment II-EV29-Luciferase coding region-linker-eGFP truncated fragment I-intron fragment I, where the sequence of eGFP truncated fragment II-EV29-Luciferase coding region-linker-eGFP truncated fragment I was shown in SEQ ID NO: 40.

The obtained circular mRNAs were transfected into 293T cells by the method provided in Example 4, and the expression of eGFP and firefly Luciferase was detected by fluorescence microscope and Luciferase reporter assay kit (abcam).

FIGS. 32A through 32C show the detection results of protein expression of eGFP and firefly Luciferase expressed by circular mRNAs containing different coding regions ligated in tandem by T2A, where FIG. 32A shows the detection results of cellular immunofluorescence, FIG. 32B shows the detection results of protein expression of eGFP and firefly Luciferase, and FIG. 32C showed the structure of Clean PIE system. The results showed as follows.

As verified by the fluorescence microscope and Luciferase Reporter Assay Kit, the expression of eGFP and Luciferase was normally expressed, proving that it was feasible to link coding regions in tandem by a linker (T2A). By this method, two or more proteins can be encoded on the same circular mRNA at the same time.

Example 19: Expression of Different Target Polypeptides Ligated in Tandem by IRES In this example, the coding regions of eGFP and firefly Luciferase were ligated in tandem by IRES, and then the expression of those proteins were verified.

According to the method of Example 3, a circular mRNA was constructed by using the Clean PIE system containing the following structure, and the circular mRNA capable of expressing eGFP and firefly Luciferase ligated in tandem by IRES was obtained.

Intron fragment II-eGFP truncated fragment II-EV29-Luciferase coding region-IRES-eGFP truncated fragment I-intron fragment I, where the sequence of eGFP truncated fragment II-EV29-Luciferase coding region-IRES-eGFP truncated fragment I was shown in SEQ ID NO: 41.

The obtained circular mRNAs were transfected into 293T cells by the method provided in Example 4, and the expression of eGFP and firefly Luciferase was detected by fluorescence microscope and Luciferase reporter assay kit (abcam).

Figure 33A:
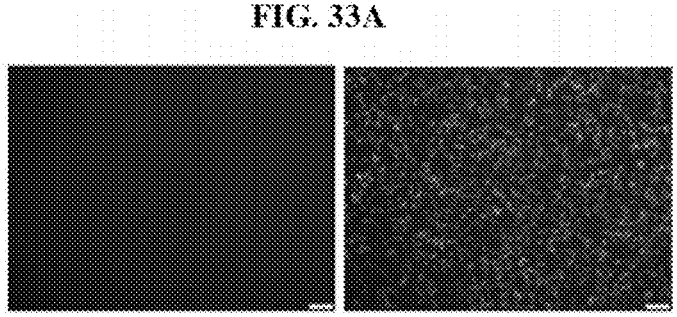
FIGS. 33A through 33C shows detection results of protein expression of eGFP and firefly Luciferase expressed by circular mRNAs containing different coding regions ligated in tandem by IRES.
Figure 33B:
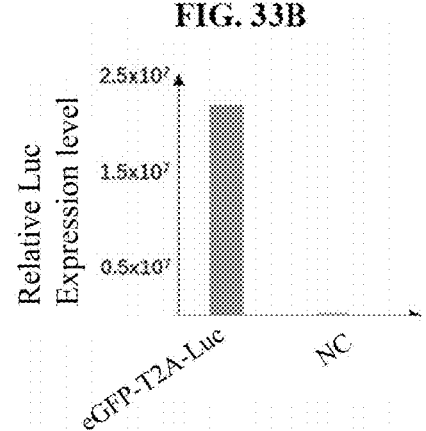
Figure 33C:
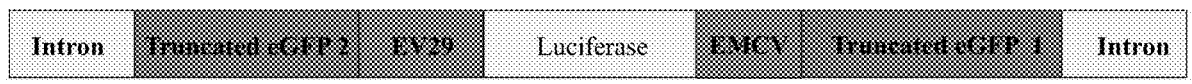

FIGS. 33A through 33C show the detection results of protein expression of eGFP and firefly Luciferase expressed by circular mRNAs containing different coding regions ligated in tandem by IRES, where FIG. 33A shows the detection results of cellular immunofluorescence, FIG. 33B shows the detection results of protein expression of eGFP and firefly Luciferase, and FIG. 33C shows the structure of Clean PIE system. The results showed as follows.

eGFP and Luciferase were ligated in tandem in the same circular mRNA by different IRES, enabling an effective circularization. As verified by the fluorescent microscope and Luciferase Reporter Assay Kit, GFP and Luciferase were normally expressed, proving that it was feasible to express different coding regions ligated in tandem by IRES. By this method, two or more proteins can be encoded on the same circular mRNA at the same time.

The above examples of the present disclosure are only for clearly illustrating the present disclosure, and are not limitations on the embodiments of the present disclosure. For those of ordinary skill in the art to which the present disclosure belongs, other changes or variations can be made on the basis of the above description. It is not necessary and impossible to exhaust all the embodiments herein. Any modification, equivalent substitution, improvement, and the like made within the spirit and principle of the present disclosure should be included within the scope of the claims of the present disclosure.

What is claimed is:

1. A recombinant nucleic acid molecule for preparing a circular RNA in vitro, the recombinant nucleic acid molecule being selected from any one of (i) to (ii):
  (i) the recombinant nucleic acid molecule comprising elements arranged in the following order in the 5' to 3' direction:
    an intron fragment II, a truncated fragment II of a coding element, a translation initiation element, a truncated fragment I of a coding element, and an intron fragment I,
    wherein the truncated fragment II is directly joined with intron fragment II without any intervening sequences, and truncated fragment I is directly joined with intron fragment I without any intervening sequences,
    wherein a 3' end of the truncated fragment I of the coding element comprises a ribozyme recognition site I that consists of a first predetermined number of nucleotides located at the 3' end of the truncated fragment I of the coding element,
    a 5' end of the truncated fragment II of the coding element comprises a ribozyme recognition site II that consists of a second predetermined number of nucleotides located at the 5' end of the truncated fragment II of the coding element,
    wherein the nucleotide sequence of the truncated fragment I of the coding element and the nucleotide sequence of the truncated fragment II of the coding element form a coding element sequence encoding at least one target polypeptide in the 5' to 3' direction; the nucleotide sequence of the truncated fragment I of the coding element corresponds to a partial sequence close to the 5' direction in the coding element sequence; and the nucleotide sequence of the truncated fragment II of the coding element corresponds to a remaining partial sequence close to the 3' direction in the coding element sequence,
    wherein the nucleotide sequence of the intron fragment I and the nucleotide sequence of the intron fragment II form an intron sequence in the 5' to 3' direction; the nucleotide sequence of the intron fragment I comprises a partial sequence close to the 5' direction in the intron sequence; and the nucleotide sequence of the intron fragment II comprises a remaining partial sequence close to the 3' direction in the intron sequence, wherein the coding element comprises a coding sequence that is generated by codon-optimization matching the coding sequence to a natural exon sequence ligated to the 5' end of the intron fragment I and/or a natural exon sequence ligated to the 3' end of the intron fragment II, wherein the coding sequence that is generated by codon-optimization is located within the ribozyme recognition site I and/or the ribozyme recognition site II, wherein a sum of the first predetermined number and the second predetermined number is not equal to 3y, wherein y≥1 and y is an integer; or
  (ii) the recombinant nucleic acid molecule comprising elements arranged in the following order in the 5' to 3' direction:
    an intron fragment III, a truncated fragment IV of a coding element, a translation initiation element, a truncated fragment III of a coding element, and an intron fragment IV, wherein the truncated fragment IV is directly joined with intron fragment III without any intervening sequences, and truncated fragment III is directly joined with intron fragment IV without any intervening sequences, wherein a 3' end of the truncated fragment III of the coding element comprises a ribozyme recognition site IV that consists of a second predetermined number of nucleotides located at the 3' end of the truncated fragment III of coding element, a 5' end of the truncated fragment IV of the coding element comprises a ribozyme recognition site III that consists of a first predetermined number of nucleotides located at the 5' end of the truncated fragment IV of coding element, wherein the nucleotide sequence of the truncated fragment III of the coding element and the nucleotide sequence of the truncated fragment IV of the coding element form a coding element sequence encoding at least one target polypeptide in the 5' to 3' direction; the nucleotide sequence of the truncated fragment III of the coding element corresponds to a partial sequence close to the 5' direction in the coding element sequence; and the nucleotide sequence of the truncated fragment IV of the coding element corresponds to a remaining partial sequence close to the 3' direction in the coding element sequence, wherein the sequence of the intron fragment III is a reverse sequence or a reverse complementary sequence of the nucleotide sequence of the intron fragment I, and the sequence of intron fragment IV is a reverse sequence or a reverse complementary sequence of the nucleotide sequence of the intron fragment II; the sequence of the ribozyme recognition site III is a reverse sequence of the nucleotide sequence of the ribozyme recognition site I, and the sequence of the ribozyme recognition site IV is a reverse sequence of the nucleotide sequence of the ribozyme recognition site II, wherein the coding element comprises a coding sequence that is generated by codon-optimization matching the coding sequence to a natural exon sequence ligated to the 5' end of the intron fragment I and/or a natural exon sequence ligated to the 3' end of the intron fragment II, wherein the coding sequence that is generated by codon-optimization is located within the ribozyme recognition site III and/or the ribozyme recognition site IV, wherein a sum of the first predetermined number and the second predetermined number is not equal to 3y, wherein y≥1 and y is an integer.

2. The recombinant nucleic acid molecule of claim 1, wherein the intron fragment I and the intron fragment II are derived from Group I intron, the ribozyme recognition site I is derived from a natural exon sequence ligated to the 5' end of the intron fragment I, and the ribozyme recognition site II is derived from a natural exon sequence ligated to the 3' end of the intron fragment II; and optionally, the Group I intron is derived from any one of the following Group I introns: phage T4 td gene, *Anabaena* tRNA$^{Leu}$, TpaCOX2, and Ptu.

3. The recombinant nucleic acid molecule of claim 1, wherein the first predetermined number of nucleotides is selected from 3 to 100 nucleotides, preferably 3 to 50 nucleotides, and more preferably 3 to 10 nucleotides; or wherein the second predetermined number of nucleotides is selected from 1 to 100 nucleotides, preferably 1 to 50 nucleotides, and more preferably 1 to 10 nucleotides.

4. The recombinant nucleic acid molecule of claim 1, wherein the translation initiation element comprises a sequence with an activity of initiating translation of an editing region; and optionally, the sequence with the activity of initiating translation of an editing region is selected from one of or a combination of two or more of the following: an IRES sequence, a 5' UTR sequence, a Kozak sequence, a sequence with m$^6$A modification, and a complementary sequence of ribosome 18S rRNA.

5. The recombinant nucleic acid molecule of claim 1, wherein the recombinant nucleic acid molecule is used for preparing a circular RNA comprising a coding element, wherein the coding element in the circular RNA comprises a coding region 1, optionally (a) at least one coding region 2, and optionally (b) at least one coding region 3;

the truncated fragment I of the coding element and the truncated fragment II of the coding element form the coding region 1, optionally (a) the at least one coding region 2, and optionally (b) the at least one coding region 3; the recombinant nucleic acid molecule comprises elements arranged in the order shown in any one of (i) to (iv) in the 5' to 3' direction:

(i) the intron fragment II, the truncated fragment II of the coding region 1, the at least one coding region 2, the translation initiation element, the truncated fragment I of the coding region 1, and the intron fragment II;

(ii) the intron fragment II, the truncated fragment II of the coding region 1, the translation initiation element, the at least one coding region 3, the truncated fragment I of coding region 1, and the intron fragment I;

(iii) the intron fragment II, the truncated fragment II of the coding region 1, the at least one coding region 2, the translation initiation element, the at least one coding region 3, the truncated fragment I of the coding region 1, and the intron fragment I;

(iv) the intron fragment II, the truncated fragment II of the coding region 1, the translation initiation element, the truncated fragment I of the coding region 1, and the intron fragment I;

alternatively, the truncated fragment III of the coding element and the truncated fragment IV of the coding element form the coding region 1, optionally (a) the at least one coding region 2, and optionally (b) the at least one coding region 3; the recombinant nucleic acid molecule comprises elements arranged in the order shown in any one of (v) to (viii) in the 5' to 3' direction:

(v) the intron fragment III, the truncated fragment IV of the coding region 1, the at least one coding region 2, the translation initiation element, the truncated fragment III of the coding region 1, and the intron fragment IV;

(vi) the intron fragment III, the truncated fragment IV of the coding region 1, the translation initiation element, the at least one coding region 3, the truncated fragment III of the coding region 1, and the intron fragment IV;

(vii) the intron fragment III, the truncated fragment IV of the coding region 1, the at least one coding region 2, the translation initiation element, the at least one coding region 3, the truncated fragment III of the coding region 1, and the intron fragment IV;

(viii) the intron fragment III, the truncated fragment IV of the coding region 1, the translation initiation element, the truncated fragment III of the coding region 1, and the intron fragment IV;

wherein the coding region 1, each coding region 2 and each coding region 3 encode any type of target polypeptides independently of one another; or
wherein the recombinant nucleic acid molecule comprises one or both elements of (i) to (ii):
(i) a linker located between the truncated fragment II of the coding region 1 and the coding region 2;
(ii) a linker located between the coding region 3 and the truncated fragment I of the coding region 1;
alternatively, the recombinant nucleic acid molecule comprises one or both elements of (iii) to (iv):
(iii) a linker located between the truncated fragment IV of the coding region 1 and the coding region 2;
(iv) a linker located between the coding region 3 and the truncated fragment III of the coding region 1;
optionally, the coding region 2 has a quantity of at least 2, and the recombinant nucleic acid molecule comprises a linker located between any two coding regions 2;
optionally, the coding region 3 has a quantity of at least 2, and the recombinant nucleic acid molecule comprises a linker located between any two coding regions 3; and
preferably, the linker is a polynucleotide encoding a 2A peptide.

6. The recombinant nucleic acid molecule of claim 1, wherein the recombinant nucleic acid molecule is used for preparing a circular RNA comprising a coding element; wherein the coding element in the circular RNA comprises a coding region 1, at least one coding region 4, and a translation initiation element located between any two adjacent coding regions;
the truncated fragment I of the coding element and the truncated fragment II of the coding element form the coding region 1, the at least one coding region 4, and the translation initiation element located between any two adjacent coding regions; or,
the truncated fragment III of the coding element and the truncated fragment IV of the coding element form the coding region 1, the at least one coding region 4, and the translation initiation element located between any two adjacent coding regions.

7. The recombinant nucleic acid molecule of claim 1, wherein the target polypeptide is a human-derived protein or non-human derived protein; and
optionally, the target polypeptide is selected from one of or a combination of two or more of the following: an antigen, an antibody, an antigen-binding fragment, a fluorescent protein, a protein with therapeutic activity, and a protein with gene-editing activity; or
wherein the recombinant nucleic acid molecule further comprises an insertion element between the truncated fragment II and the translation initiation element, or an insertion element between the truncated fragment IV and the translation initiation element; the insertion element is at least one selected from the group consisting of (i) to (iii):
(i) a transcriptional regulatory element, (ii) a translational regulatory element, and (iii) a purification element;
preferably, the insertion element is ligated to the 5' end of any translation initiation element;
optionally, the insertion element comprises a sequence selected from one of or a combination of two or more of the following:
an untranslated region sequence, a polyA sequence, an aptamer sequence, a riboswitch sequence, and a transcriptional regulator-binding sequence; or
wherein the recombinant nucleic acid molecule further comprises a 5' homologous arm and a 3' homologous arm, and the nucleotide sequence of the 5' homologous arm is complementary pairing with the nucleotide sequence of the 3' homologous arm;
the 5' homologous arm is ligated to the 5' end of the intron fragment II, and the 3' homologous arm is ligated to the 3' end of the intron fragment I; or, the 5' homologous arm is ligated to the 5' end of the intron fragment III, and the 3' homologous arm is ligated to the 3' end of the 3' intron fragment IV; or
wherein a nucleotide sequence derived from an exon is not comprised in any one of the intron fragment I, the translation initiation element, or the intron fragment II, or between any two of the intron fragment I, the truncated fragment II of the coding element, the translation initiation element, the truncated fragment I of the coding element, and the intron fragment II; or,
a reverse sequence or reverse complementary sequence of a nucleotide sequence derived from an exon is not comprised in any one of the intron fragment III, the translation initiation element, and the intron fragment IV, or between any two of the intron fragment III, the truncated fragment IV of the coding element, the translation initiation element, the truncated fragment III of the coding element, and the intron fragment IV.

8. A recombinant expression vector, comprising the recombinant nucleic acid molecule of claim 1.

9. A method for preparing a circular RNA in vitro, comprising the steps of:
transcribing the recombinant nucleic acid molecule of claim 1 to form a cyclization precursor nucleic acid molecule;
cyclizing the cyclization precursor nucleic acid to obtain the circular RNA; and
optionally, further comprising the step of purifying the circular RNA.

10. The recombinant nucleic acid molecule of claim 1, wherein during circularization, the truncated fragment I is directly joined with the truncated fragment II, without any intervening sequences.

11. The recombinant nucleic acid molecule of claim 1, wherein during circularization, the truncated fragment III is directly joined with the truncated fragment IV, without any intervening sequences.

12. The recombinant nucleic acid molecule of claim 1, wherein the recombinant nucleic acid molecule further comprises an IRES sequence that is flanked by truncated fragment I and truncated fragment II.

13. The recombinant nucleic acid molecule of claim 1, wherein during circularization, the truncated fragment I is directly joined with the truncated fragment II, without any intervening sequences, and after circularization, the truncated fragment I and the truncated fragment II form a ligation junction that is located within the coding element sequence.

14. The recombinant nucleic acid molecule of claim 1, wherein the coding element comprises a coding sequence that is not naturally-occurring.

* * * * *

SEQUENCE LISTING

```
Sequence total quantity: 80
SEQ ID NO: 1            moltype = DNA  length = 19
FEATURE                 Location/Qualifiers
misc_feature            1..19
                        note = sequence of PolyAC
source                  1..19
                        mol_type = other DNA
                        organism = synthetic construct
SEQUENCE: 1
aaaaaacaaa aaacaaaac                                                    19

SEQ ID NO: 2            moltype = DNA  length = 1542
FEATURE                 Location/Qualifiers
misc_feature            1..1542
                        note = sequence of circular RNA
source                  1..1542
                        mol_type = other DNA
                        organism = synthetic construct
SEQUENCE: 2
ggggttaaaa cagcctgtgg gttgatccca cccacagggc ccactgggcg ctagcactct    60
ggtatcacgg tacctttgtg cgcctgtttt atacttcctc ccccaactgc aacttagaag   120
taacacaaac cgatcaacag tcagcgtggc acaccagcca cgttttgatc aaacacttct   180
gttacccegg actgagtatc aatagactge tcacgeggtt gaaggagaaa acgttcgtta   240
tccggccaac tacttcgaga aacctagtaa cgccatggaa gttgtggagt gtttcgctca   300
gcactacccc agtgtagatc aggttgatga gtcaccgcat tccccacggg tgaccgtggc   360
ggtggctgcg ttggcggcct gcccatgggg aaacccatgg gacgctctta tacagacatg   420
gtgcgaaagag tctattgagc tagttggtag tcctccggcc cctgaatgcg gctaatccca   480
actgcggagc atacactctc aagccagagg gtagtgtgtc gtaatgggca actctgcagc   540
ggaaccgact actttgggtg tccgtgtttc attttattcc tatactggct gcttatggtg   600
acaattgaga gattgttacc atatagctat tggattggcc atccggtgac taacagagct   660
attatatatc ttttttgttgg gtttatacca cttagcttga aagaggttaa aactctacat   720
tacattttaa tactgaacac cgcaaaatgg tgtcaaaggg tgaggaatta ttcaccggcg   780
tggtgcctat ccttgtggaa cttgatggag atgtgaacgg acacaaattc agtgtatcag   840
gagaaggaga aggagatgca acatacggaa agctcactct taaatttatc tgcacaacag   900
gaaagctccc ggtgccttgg cctacacttg tgacaacact tacatacgga gtgcaatgct   960
tctcgcgtta ccctgatcac atgaaacaac acgatttcct caagagtgca atgcctgaag   1020
gatacgtgca agaaagaaca atcttcttca aggacgatgg aaactacaag actcgtgcag   1080
aagtgaaatt tgaaggagat acacttgtga acagaatcga acttaaagga atcgatttca   1140
aggaggatgg aaacatcctt ggacacaaac ttgaatacaa ctacaactca cacaacgtgt   1200
acatcatgge agataaacag aagaatggta tcaaagtgaa cttaagatt cgccacaaca   1260
tcgaagatgg gtctgtgcaa cttgcagatc actaccaaca gaatacgccg ataggagatg   1320
gacctgtgct tcttcctgat aaccactacc tttcaacaca atcagcactt tcaaaggacc   1380
caaacgagaa gcgagaccac atggtgcttc ttgaatttgt gacagcagca ggaatcacac   1440
ttggaatgga tgaactttac aaatgaaaaa aacaaaaaac aaaacaaaaa acaaaaaaca   1500
aaacaaaaaa caaaaaacaa aaaaaaaca aaaaacaaaa cc                        1542

SEQ ID NO: 3            moltype = AA   length = 238
FEATURE                 Location/Qualifiers
REGION                  1..238
                        note = sequence of eGFP
source                  1..238
                        mol_type = protein
                        organism = synthetic construct
SEQUENCE: 3
MVSKGEELFT GVVPILVELD GDVNGHKFSV SGEGEGDATY GKLTLKFICT TGKLPVPWPT      60
LVTTLTYGVQ CFSRYPDHMK QHDFFKSAMP EGYVQERTIF FKDDGNYKTR AEVKFEGDTL    120
VNRIELKGID FKEDGNILGH KLEYNYNSHN VYIMADKQKN GIKVNFKIRH NIEDGSVQLA    180
DHYQQNTPIG DGPVLLPDNH YLSTQSALSK DPNEKRDHMV LLEFVTAAGI LGMDELYK      238

SEQ ID NO: 4            moltype = DNA  length = 222
FEATURE                 Location/Qualifiers
misc_feature            1..222
                        note = sequence of intron region II
source                  1..222
                        mol_type = other DNA
                        organism = synthetic construct
SEQUENCE: 4
ggatcctaat acgactcact atagggagac cctcgcacag tgagcaactg acggaggttc     60
tacataaatg cctaacgact atcccttggg ggagtagggt caagtgactc gaaacgtag    120
acaacttgct ttaacaagtt ggagatatag tctgctctgc atgtgacat gcagctggat    180
ataattccgg ggtaagatta acgaccttat ctgaacataa tg                      222

SEQ ID NO: 5            moltype = DNA  length = 128
FEATURE                 Location/Qualifiers
misc_feature            1..128
                        note = sequence of intron region I
source                  1..128
                        mol_type = other DNA
```

```
                        organism = synthetic construct
SEQUENCE: 5
taattgaggc ctgagtataa ggtgacttat acttgtaatc tatctaaacg gggaacctct    60
ctagtagaca atcccgtgct aaattgtagg actaccgtca gttgctcact gtgcatcaga   120
tttctaga                                                            128

SEQ ID NO: 6            moltype = DNA   length = 163
FEATURE                 Location/Qualifiers
misc_feature            1..163
                        note = sequence of intron region II
source                  1..163
                        mol_type = other DNA
                        organism = synthetic construct
SEQUENCE: 6
ctacataaat gcctaacgac tatccctttg gggagtaggg tcaagtgact cgaaacgata    60
gacaacttgc tttaacaagt tggagatata gtctgctctg catggtgaca tgcagctgga   120
tataattccg gggtaagatt aacgacctta tctgaacata atg                     163

SEQ ID NO: 7            moltype = DNA   length = 93
FEATURE                 Location/Qualifiers
misc_feature            1..93
                        note = sequence of intron region I
source                  1..93
                        mol_type = other DNA
                        organism = synthetic construct
SEQUENCE: 7
taattgaggc ctgagtataa ggtgacttat acttgtaatc tatctaaacg gggaacctct    60
ctagtagaca atcccgtgct aaattgtagg act                                 93

SEQ ID NO: 8            moltype = DNA   length = 59
FEATURE                 Location/Qualifiers
misc_feature            1..59
                        note = sequence of homology arm
source                  1..59
                        mol_type = other DNA
                        organism = synthetic construct
SEQUENCE: 8
ggatcctaat acgactcact atagggagac cctcgcacag tgagcaactg acggaggtt     59

SEQ ID NO: 9            moltype = DNA   length = 35
FEATURE                 Location/Qualifiers
misc_feature            1..35
                        note = sequence of homology arm
source                  1..35
                        mol_type = other DNA
                        organism = synthetic construct
SEQUENCE: 9
accgtcagtt gctcactgtg catcagattt ctaga                               35

SEQ ID NO: 10           moltype = DNA   length = 742
FEATURE                 Location/Qualifiers
misc_feature            1..742
                        note = sequence of Ev29 IRES
source                  1..742
                        mol_type = other DNA
                        organism = synthetic construct
SEQUENCE: 10
ttaaaacagc ctgtgggttg atcccaccca cagggcccac tgggcgctag cactctggta    60
tcacggtacc tttgtgcgcc tgttttatac ttcctcaccc aactgcaact tagaagtaac   120
acaaaccgat caacagtcag cgtggcacac cagccacgtt ttgatcaaac acttcgttta   180
ccccggactg agtatcaata gactgctcac gcggttgaag gagaaaacgt tcgttatccg   240
gccaactact tcgagaaacc tagtaacgcc atggaagttg tggagtgttt cgctcagcac   300
taccccagtg tagatcaggt tgatgagtca ccgcattccc cacgggtgac cgtggcggtg   360
gctgcgttgg cggcctgccc atggggaaac ccatgggacg ctcttataca gacatggtgc   420
gaagagtcta ttgagctagt tggtagtcct ccggcccctg aatgcggcta atcccaactg   480
cggagcatac actctcaagc cagagggtag tgtgtcgtaa tgggcaactc tgcagcggaa   540
ccgactactt gggtgtccg tgtttcattt tattcctata ctggctgctt atggtgacaa   600
ttgagagatt gttaccatat agctattgga ttggccatcc ggtgactaac agagctatta   660
tatatctttt tgttgggttt ataccactta gcttgaaaga ggtaaaaact ctacattaca   720
ttttaatact gaacaccgca aa                                            742

SEQ ID NO: 11           moltype = DNA   length = 720
FEATURE                 Location/Qualifiers
misc_feature            1..720
                        note = sequence of eGFP
source                  1..720
                        mol_type = other DNA
                        organism = synthetic construct
SEQUENCE: 11
```

```
atggtgtcaa agggtgagga attattcacc ggcgtggtgc ctatccttgt ggaacttgat   60
ggagatgtga acggacacaa attcagtgta tcaggagaag gagaaggaga tgcaacatac  120
ggaaagctca ctcttaaatt tatctgcaca acaggaaagc tcccggtgcc ttggcctaca  180
cttgtgacaa cacttacata cggagtgcaa tgcttctcgc gttaccctga tcacatgaaa  240
caacacgatt tcttcaagag tgcaatgcct gaaggatacg tgcaagaaag aacaatcttc  300
ttcaaggacg atggaaacta caagactcgt gcagaagtga aatttgaagg agatacactt  360
gtgaacagaa tcgaacttaa aggaatcgat ttcaaggagg atggaaacat ccttggacac  420
aaacttgaat acaactacaa ctcacacaac gtgtacatca tggcagataa acagaagaat  480
ggtatcaaag tgaactttaa gattcgccac aacatcgaag atggatcagt gcaacttgca  540
gatcactacc aacagaatac gccgatagga gatggacctg tgcttcttcc tgataaccac  600
taccttttcaa cacaatcagc actttcaaag acccaaacg agaagcgaga ccacatggtg  660
cttcttgaat tgtgacagc agcaggaatc acacttggaa tggatgaact ttacaaatga  720

SEQ ID NO: 12          moltype = DNA  length = 526
FEATURE                Location/Qualifiers
misc_feature           1..526
                       note = sequence of truncated region I ofeGFP
source                 1..526
                       mol_type = other DNA
                       organism = synthetic construct
SEQUENCE: 12
atggtgtcaa agggtgagga attattcacc ggcgtggtgc ctatccttgt ggaacttgat   60
ggagatgtga acggacacaa attcagtgta tcaggagaag gagaaggaga tgcaacatac  120
ggaaagctca ctcttaaatt tatctgcaca acaggaaagc tcccggtgcc ttggcctaca  180
cttgtgacaa cacttacata cggagtgcaa tgcttctcgc gttaccctga tcacatgaaa  240
caacacgatt tcttcaagag tgcaatgcct gaaggatacg tgcaagaaag aacaatcttc  300
ttcaaggacg atggaaacta caagactcgt gcagaagtga aatttgaagg agatacactt  360
gtgaacagaa tcgaacttaa aggaatcgat ttcaaggagg atggaaacat ccttggacac  420
aaacttgaat acaactacaa ctcacacaac gtgtacatca tggcagataa acagaagaat  480
ggtatcaaag tgaactttaa gattcgccac aacatcgaag atgggt             526

SEQ ID NO: 13          moltype = DNA  length = 194
FEATURE                Location/Qualifiers
misc_feature           1..194
                       note = sequence of truncated region II of eGFP
source                 1..194
                       mol_type = other DNA
                       organism = synthetic construct
SEQUENCE: 13
ctgtgcaact tgcagatcac taccaacaga atacgccgat aggagatgga cctgtgcttc   60
ttcctgataa ccactacctt tcaaacacaat cagcactttc aaaggaccca acgagaagc  120
gagaccacat ggtgcttctt gaatttgtga cagcagcagg aatcacactt ggaatggatg  180
aactttacaa atga                                                   194

SEQ ID NO: 14          moltype = DNA  length = 4447
FEATURE                Location/Qualifiers
misc_feature           1..4447
                       note = sequence of pUC57-EV29-eGFP
source                 1..4447
                       mol_type = other DNA
                       organism = synthetic construct
SEQUENCE: 14
cgcgcgtttc ggtgatgacg gtgaaaacct ctgacacatg cagctcccgg agactgtcac   60
agcttgtctg taagcggatg ccgggagcag acaagcccgt cagggcgcgt cagcgggtgt  120
tggcgggtgt cggggctggc ttaactatgc ggcatcagag cagattgtac tgagagtgca  180
ccatatgcgg tgtgaaatac cgcacagatg cgtaaggaga aaataccgca tcaggcgcca  240
ttcgccattc aggctgcgca actgttggga agggcgatcg gtgcgggcct cttcgctatt  300
acgccagctg gcgaaagggg gatgtgctgc aaggcgatta agttgggtaa cgccagggtt  360
ttcccagtca cgacgttgta aaacgacggc cagtgaattg acgcgtattg ggatgaattc  420
ggatcctaat acgactcact atagggagac cctcgcacag tgagcaactg acggaggttc  480
tacataaatg cctaacgact atcccttgg ggagtagggt caagtgactc gaaacgatag  540
acaacttgct ttaacaagtt ggagatatag tctgctctgc atggtgacat gcagctggat  600
ataattccgg ggtaagatta acgacctat ctgaacataa tgctgtgcaa cttgcagatc  660
actaccaaca gaatacgccg ataggagatg gacctgtgct tcttcctgat aaccactacc  720
tttcaacaca atcagcactt tcaaaggacc caaacgagaa gcgagaccac atggtgcttc  780
ttgaatttgt gacagcagca ggaatcacac ttggaatgga tgaactttac aaatgagggg  840
ttaaaacagc ctgtgggttg atcccaccca cagggcccac tgggcgctag cactctgta   900
tcacggtacc tttgtgcgcc tgttttatac ttcctccccc aactgcaact tagaagtaac  960
acaaaccgat caacagtcag cgtgcacac cagccacgtt ttgatcaaac acttctgtta  1020
ccccggactg agtatcaata gactgctcac gcggttgaag gagaaaacgt tcgttatccg 1080
gccaactact tcgagaaacc tagtaacgcc atggaagttg tggagtgttt cgctcagcac 1140
tacccagtg tagatcaggt tgatgagtca ccgcattccc cacgggtgac cgtggcggtg 1200
gctgcgttgc cggcctgccc atggggaaac ccatgggacg ctcttataca gacatggtgc 1260
gaagagtcta ttgagctagt tggtagtcct ccgggccctg aatgcggcta atcccaactg 1320
cggagcatac actctcaagc cagagggtag tgtgtcgtaa tggcaactc tgcagcggaa 1380
ccgactactt ggggtgtccg tgtttcatt tattcctata ctggctgctt atggtgcaa 1440
ttgagagatt gttaccatat agctattgga ttggccatcc ggtgactaac agagctatta 1500
tatatctttt tgttgggttt ataccactta gcttgaaaga ggttaaaact ctacattaca 1560
ttttaatact gaacaccgca aaatggtgtc aaagggtgag gaattattca ccggcgtggt 1620
```

```
gcctatcctt gtggaacttg atggagatgt gaacggacac aaattcagtg tatcaggaga  1680
aggagaagga gatgcaacat acggaaagct cactcttaaa tttatctgca caacaggaaa  1740
gctcccggtg ccttggccta cacttgtgac aacacttaca tacggagtgc aatgcttctc  1800
gcgttaccct gatcacatga aacaacacga tttcttcaag agtgcaatgc ctgaaggata  1860
cgtgcaagaa agaacaatct tcttcaagga cgatggaaca tacaagactc gtgcagaagt  1920
gaaatttgaa ggagatacac ttgtgaacag aatcgaactt aaaggaatcg atttcaagga  1980
ggatggaaac atccttggac acaaacttga atacaactac aactcacaca acgtgtacat  2040
catggcagat aaacagaaga atggtatcaa agtgaacttt aagattcgcc acaacatcga  2100
agatgggtta attgaggcct gagtataagg tgacttatac ttgtaatcta tctaaacggg  2160
gaacctctct agtagacaat cccgtgctaa attgtaggac taccgtcagt tgctcactgt  2220
gcatcagatt tctagaatcc caatggcgcg ccgagcttgg ctcgagcatg gtcatagctg  2280
tttcctgtgt gaaattgtta tccgctcaca attccacaca acatacgagc cggaagcata  2340
aagtgtaaag cctggggtgc ctaatgagtg agctaactca cattaattgc gttgcgctca  2400
ctgcccgctt tccagtcggg aaacctgtcg tgccagctgc attaatgaat cggccaacgc  2460
gcggggagag gcggtttgcg tattgggcgc tgttccgctt cctcgctcac tgactcgctg  2520
cgctcggtcg ttcggctgcg gcgagcggta tcagctcact caaaggcggt aatacggtta  2580
tccacagaat caggggataa cgcaggaaag aacatgtgag caaaaggcca gcaaaggcc  2640
aggaaccgta aaaaggccgc gttgctggcg tttttccata ggctccgccc cctgacgag  2700
catcacaaaa atcgacgctc aagtcagagg tggcgaaacc cgacaggact ataaagatac  2760
caggcgtttc cccctggaag ctccctcgtg cgctctcctg ttccgaccct gccgcttacc  2820
ggatacctgt ccgcctttct cccttcggga agcgtggcgc tttctcatag ctcacgctgt  2880
aggtatctca gttcggtgta ggtcgttcgc tccaagctgg gctgtgtgca cgaaccccc  2940
gttcagcccg accgctgcgc cttatccggt aactatcgtc ttgagtccaa cccggtaaga  3000
cacgacttat cgccactggc agcagccact ggtaacagga ttagcagagc gaggtatgta  3060
ggcggtgcta cagagttctt gaagtggtgg cctaactacg gctacactag aagaacagta  3120
tttggtatct gcgctctgct gaagccagtt accttcggaa aaagagttgg tagctcttga  3180
tccggcaaac aaaccaccgc tggtagcggt ggtttttttg tttgcaagca gcagattacg  3240
cgcagaaaaa aaggatctca agaagatcct ttgatctttt ctacggggtc tgacgctcag  3300
tggaacgaaa actcacgtta agggattttg gtcatgagat tatcaaaaag gatcttcacc  3360
tagatccttt taaattaaaa atgaagtttt aaatcaatct aaagtatata tgagtaaact  3420
tggtctgaca gttagaaaaa ctcatcgagc atcaaatgaa actgcaattt attcatatca  3480
ggattatcaa taccatattt ttgaaaaagc cgtttctgta atgaaggaga aaactcaccg  3540
aggcagttcc ataggatggc aagatcctgg tatcggtctg cgattccgac tcgtccaaca  3600
tcaatacaac ctattaattt cccctcgtca aaaataaggt tatcaagtga gaaatcacca  3660
tgagtgacga ctgaatccgg tgagaatggc aaaagtttat gcatttcttt ccagacttgt  3720
tcaacaggcc agccattacg ctcgtcatca aaatcactcg catcaaccaa accgttattc  3780
attcgtgatt gcgcctgagc gaaacgaaat acgcgatcgc tgttaaaagg acaattacaa  3840
acaggaatcg aatgcaaccg gcgcaggaac actgccagcg catcaacaat attttcacct  3900
gaatcaggat attcttctaa tacctggaat gctgttttcc cagggatcgc agtggtgagt  3960
aaccatgcat catcaggagt acggataaaa tgcttgatgg tcggaagagg cataaattcc  4020
gtcagccagt ttagtctgac catctcatct gtaacatcat tggcaacgct acctttgcca  4080
tgtttcagaa acaactctgg cgcatcgggc ttcccataca atcgatagat tgtcgcacct  4140
gattgcccga cattatcgcg agcccattta tacccatata atcagcatcc atgttggaaa  4200
tttaatcgcg gcctagagca agacgtttcc cgttgaatat ggctcatact cttccttttt  4260
caatattatt gaagcattta tcaggggttat tgtctcatga gcggatacat atttgaatgt  4320
atttagaaaa ataaacaaat aggggttccg cgcacatttc cccgaaaagt gccacctgac  4380
gtctaagaaa ccattattat catgacatta acctataaaa ataggcgtat cacgaggccc  4440
ttttgtc                                                             4447
SEQ ID NO: 15           moltype = DNA  length = 2494
FEATURE                 Location/Qualifiers
misc_feature            1..2494
                        note = sequence of truncatedregion I ofspCas9
source                  1..2494
                        mol_type = other DNA
                        organism = synthetic construct
SEQUENCE: 15
atggactaca aggaccacga cggcgactac aaggaccacg acatcgacta caaggacgac   60
gatgacaaga tggcccccaa gaagaagagg aaggtgggca tccacggcgt gcccgccgcc  120
gacaagaagt acagcatcgg cctggacatc ggcaccaaca gcgtgggctg gccgtgatc  180
accgacgact acaaggtgcc cagcaagaag ttcaaggtgc tgggcaacac cgacaggcac  240
agcatcaaga gaacctgat cggcgccctg ctgttcgaca cgggcgagac cgccgaggcc  300
accaggctga gaggaccgc caggaggagg tacaccagga gaagaacag gatctgctac  360
ctgcaggaa tcttcagcaa cgagatggcc aaggtgacag acagcttctt ccacaggcta  420
gaggagagct tcctggtgga ggaggacaag aagcacgaga ggcacccat cttcggcaac  480
atcgtggacg aggtggccta ccacgagaag taccccacca tctaccacct gaggaagaag  540
ctggccgaca gcaccgacaa ggccgacctg aggctgatct acctggccct cgcccacatg  600
atcaagttca ggggccactt cctgatcgag ggcgacctga accccgacaa cagcgacgtg  660
gacaagctgt tcatccagct ggtgcagacc tacaaccagc tgttcgagga gaaccccatc  720
aacgccagca gggtggacgc caaggccatc ctgagcgcca ggctgagcaa gagcaggagg  780
ctggagaacc tgatcgccca gctgcccggc gagaagaaga acggcctgtt cggcaacctg  840
atcgccctgc tgctgggcct gacccccaac ttcaagagca cttcgacct ggccgaggac  900
gccaagctga gctgagccga ggacacctac gacgacgacc tggacaacct gctggcccag  960
atcggcgacc agtacgccga cctgttcctg gccgccaaga acctgagcga cgccatcctg 1020
ctgagcgaca tcctgagggt gaacagcgag atcaccaagg ccccttgag cgccagcatg 1080
atcaagaggt acgacgagca ccaccaggac ctgaccctgc tgaaggccct ggtgaggcag 1140
cagctgcccg agaagtacaa ggagatcttc ttcgaccaga gcaagaacgg ctacgccggc 1200
tacatcgacg gcggcgccag ccaggaggag ttctacaagt catcaagcc catcctggag 1260
aagatggacg gcaccgagga gctgctggcc agctgaaca gggaggacct gctgaggaag 1320
```

```
cagaggacct tcgacaacgg cagcatcccc caccagatcc acctgggcga gctgcacgcc  1380
atcctgagga ggcaggagga cttctacccc ttcctgaagg acaacaggga gaagatcgag  1440
aagatcctga ccttcaggat ccctactac gtgggccccc tggccagggg caacagcagg   1500
ttcgcctgga tgaccaggaa gagcgaggag accatcaccc cctggaactt cgaggaggtg  1560
gtggacaagg gcgccagcgc ccagagcttc atcgagagga tgcaacttc gacaagaac    1620
ctgcccaacg agaaggtgct gcccaagcac agcctgctgt acgagtactt caccgtgtac  1680
aacgagctga ccaaggtgaa gtacgtgacc gagggcatga ggaagcccgc cttcctgagc  1740
ggcgagcaga gaaggccat cgtggacctg ctgttcaaga ccaacaggaa ggtgaccgtg   1800
aagcagctga aggaggacta cttcaagaag atcgagtgct tcgacagcgt ggagatcagc  1860
ggcgtggagg acaggttcaa cgccagcctg ggcacctacc acgacctgct gaagatcatc  1920
aaggataagg acttcctgga caacgaggag aacgaggaca tcctggagga catcgtgctg  1980
accctgacac tgttcgagga caaggagatg atcgaggaga ggctgaagaa gtacgcccac  2040
ctgttcgacg acaaggtgat gaagcagctg aagaggagga ggtacaccgg ctggggcagg  2100
ctgagcagga agctgatcaa cggcatcagg gacaagcaga ccggcaagac catcctggac  2160
ttcctgaaga gcgacggctt cgccaacagg aacttcatgc agctgatcca cgacgacagc  2220
ctgaccttca aggaggacat ccagaaggcc caggtgagcg gccagggcga cagcctgcac  2280
gagcacatcc caacctggc cggcagcccc gccatcaaga agggcatcct gcagaccgtg  2340
aaggtggtg acgagctggt gaaggtgatg ggcaggcaca gcccgagaa catcgtgatc    2400
gagatggcca gggagaacca gaccacccag aagggccaga gaacagcag ggagaggatg   2460
aagaggatcg aggagggcat caaggagctt gggt                              2494

SEQ ID NO: 16           moltype = DNA    length = 1766
FEATURE                 Location/Qualifiers
misc_feature            1..1766
                        note = sequence of truncatedregion II ofspCas9
source                  1..1766
                        mol_type = other DNA
                        organism = synthetic construct
SEQUENCE: 16
ctgacatcct gaaggagtac cccgtggaga acacccagct gcagaacgag aagctgtacc  60
tctactacct gcagaacggc agggacatgt acgtggacca ggagctggac atcaacaggc  120
tgagcgacta cgacgtggac cacatcgtgc cccagagctt cctgaaggac gacagcatcg  180
acaacaaggt gctgaccagg agcgacaaga cagggcaa gagcgacaac gtgcccagcg   240
aggaggtggt gaagaagatg aagaactact ggaagcagct gctgaacgcc aagctgatca  300
cccaggaa gttcgacaac ctgaccaagg ccgagagggg cggcctgagc gagctggaca    360
aggccggctt catcaagagg cagctggtgg agaccaggca gatcaccaag cacgtggccc  420
agatcctgga cagcaggatg aacaccaagt acgacgagaa cgacaagctg atcagggagg  480
tgagggtgat cacccctgaag agcaagctgg tgagcgactt caggaaggac ttccagttct  540
acaaggtgag ggagatcaac aactaccacc acgcccacga cgcctacctg aacgccgtgg  600
tgggcaccgc cctgatcaag aagtacccca gctggagag cgagttcgtg tacggcgact  660
acaaggtgta cgacgtgaga aagatgatcg ccaagagcga gcaggagatc ggcaaggcca  720
ccgccaagta cttcttctac agcaacatca tgaacttctt caagaccgag atcacccctgg 780
ccaacggcga gatcaggaag aggccctga tcgagacaca cggcagacgg agcgcagatcg 840
tgtgggacaa gggcagggac ttcgccaccg tgaggaaggt gctgagcatg cccaggtga   900
acatcgtgaa gaagaccgag gtgcagaccg cggcttcag caaggagagc atcctgccca   960
agaggaacag cgacaagctg atcgccagga gaaggactg gaccccaag aagtacggcg   1020
gcttcgacag cccaccgtg gcctacagcg tgctggtgat ggcaaggtg ggaaagggca   1080
agagcaaaaa gctgaagagc gtgaaggagc tgctgggcat caccatcatg gagaggagca  1140
gcttcgagaa gaaccccatc gacttcctgg aggccaaggg ctacaaggag gtgaggaagg  1200
acctgatcat caagctgccc aagtacagcc tgttcgagct ggaaacggc aggaagagga   1260
tgctggcag cgccggcgag ctgcagaagg caacgaggt ggccctgccc agcaagtacg    1320
tgaacttcct gtacctggcc agccactacg agaagctgaa gggcagcccc gaggacaacg  1380
agcagaagca gctgttcgtg gagcagcaca gcactacct ggacgagatc atcgagcaga   1440
tcagcgagtt cagcaagagg gtgatcctgg ccgacgccaa cctggacaag gtgctgagcg  1500
cctacaacaa gcacagggac aagcccatca gggagcaggc cgagaacatc atccacctgt  1560
tcaccctgac caacctgggc gcccccgccg ccttcaagta cttcgacacc accatcgaca  1620
ggaagaggta caccagcacc aaggaggtgc tggacgccac cctgatccac cagagcatca  1680
ccggcctgta cgagaccagg atcgacctga gccagctggg cggcgactcc ggcccctcca  1740
agaagaagag gaaggtgggc ggctga                                      1766

SEQ ID NO: 17           moltype = DNA    length = 826
FEATURE                 Location/Qualifiers
misc_feature            1..826
                        note = sequence of truncatedregion I offLUC
source                  1..826
                        mol_type = other DNA
                        organism = synthetic construct
SEQUENCE: 17
atggaggacg ccaagaacat caagaagggc cctgcccctt tctaccctct ggaggacggc  60
accgccggcg agcagctgca caaggccatg aagaggtacg ccctggtgcc tggcaccatc  120
gccttcaccg acgcccacat cgaggtggac atcacctacg ccgagtactt cgagatgagc  180
gtgaggctgg ccgaggccat gaagaggtac ggcctgaaca ccaaccacag gatcgtggtg  240
tgcagcgaga cagcctgca gttcttcatg cctgtgctgg gcgccctgtt catcggcgtg  300
gccgtggccc ctgccaacga catctacaac gagagggagc tgctgaacag catgggcatc  360
agccagccta ccgtggtgtt cgtgagcaag aagggcctgc agaagatcct gaacgtgcag  420
aagaagctgc ctatcatcca gaagatcatc atcatggaca gcaagaccga ctaccagggc  480
ttccagagca tgtacacctt cgtgaccagc cacctgcctc ctggcttcaa cgagtacgac  540
ttcgtgcctg agagcttcga cagggacaag accatcgccc tgatcatgaa cagcagcggc  600
agcaccggcc tgcctaaggg cgtggccctg cctcacagga ccgcctgcgt gaggttcagc  660
```

```
cacgccaggg accctatctt cggcaaccag atcatccctg acaccgccat cctgagcgtg   720
gtgcctttcc accacggctt cggcatgttc accaccctgg gctacctgat ctgcggcttc   780
agggtggtgc tgatgtacag gttcgaggag gagctgttcc ttaggt                  826
```

```
SEQ ID NO: 18           moltype = DNA   length = 827
FEATURE                 Location/Qualifiers
misc_feature            1..827
                        note = sequence of truncatedregion II offLUC
source                  1..827
                        mol_type = other DNA
                        organism = synthetic construct
SEQUENCE: 18
ctctgcagga ctacaagatc cagagcgccc tgctggtgcc taccctgttc agcttcttcg    60
ccaagagcac cctgatcgac aagtacgacc tgagcaacct gcacgagatc gccagcggcg   120
gcgcccctct gagcaaggag gtgggcgagg ccgtggccaa gaggttccac ctgcctggca   180
tcaggcaggg ctacggcctg accgagacca ccagcgccat cctgatcacc cctgagggcg   240
acgacaagcc tggcgccgtg ggcaaggtgg tgccttttct cgaggccaag gtggtggacc   300
tggacaccgg caagaccctg ggcgtgaacc agagggggca gctgtgcgtg aggggcccta   360
tgatcatgag cggctacgtg aacaacccct aggccaccaa cgccctgatc gacaaggacg   420
gctggctgca cagcggcgac atcgcctact gggacgagga cgagcacttc ttcatcgtgg   480
acaggctgaa gagcctgatc aagtacaagg ctaccaggtg ggccctgcc gagctggaga   540
gcatcctgct gcagcaccct aacatcttcg acgccggcgt ggctgcttg cctgatgacg   600
atgctggaga gctgcctgcc gccgtggtgg tgctggagca cggcaagacc atgaccgaga   660
aggagatcgt ggactacgtg gccagccagg tgaccaccgc caagaagctg aggggcgcg   720
tggtgttcgt ggacgaggtg cctaagggcc tgaccggcaa gctggacgcc aggaagatca   780
gggagatcct gatcaaggcc aagaagggcg gcaagatcgc cgtgtga               827
```

```
SEQ ID NO: 19           moltype = DNA   length = 1351
FEATURE                 Location/Qualifiers
misc_feature            1..1351
                        note = sequence of truncatedregion I ofIL12
source                  1..1351
                        mol_type = other DNA
                        organism = synthetic construct
SEQUENCE: 19
atgagggtga ccgcccctag gaccctgatc ctgctgctga gcggcgccct ggccctcacc    60
gagacctggg ccggcagcgg aagcatgtgg gagctggaga ggacgtgta cgtggtggga   120
gtcgactgga cccctgacgc ccctggcgag accgtgaacc tgacctgcga caccctgag   180
gaggacgaca tcacctggac cagcgaccag aggcacggcg tgatcggcag cggcaagacc   240
ctgaccatca ccgtgaagga gttcctggac gccggccagt acacctgcca caagggcggc   300
gagaccctga gccactccca cctgctgctg cacaagaagg agaacggcat ctggagcacc   360
gagatcctga agaacttcaa gaacaagacc ttcctgaagt gcgaggcccc taactacagc   420
ggcaggttca cctgcagctg gctggtgcag aggaacatgg acctgaagtt caatatcaag   480
agcagcagct ccagccctga cagcagggcc gtgacctgcg gcatggcag cctgagcgcc   540
gagaaggtga ccctggacca gagggactac gagaagtaca gcgtgagctg ccaggaggac   600
gtgacctgcc ctaccgccga ggagaccctg cctatcgagc tggcccctgg agccaggcag   660
cagaacaagt acgagaacta cagcaccagc ttcttcatca gggacatcat caagcctgac   720
cctcctaaga acctgcagat gaagcctctg aagaacagcc aggtggaggt gagctggaga   780
taccctgaca gctggagcac ccctcacagc tacttcagcc tgaagttctt cgtgaggatc   840
cagaggaaga aggagaagat gaaggagacc gaggagggct gcaaccagaa gggcgccttc   900
ctggtggaga agaccagcac cgaggtgcag tgcaagggcg gcaacgtgtg cgtgcaggcc   960
caggacaggt actacaacag cagctgcagc aagtgggcct gcgtgccttg cagggtgagg  1020
agcgtgcctg gcgtgggcgt ccctggcgtg gcagggtga tccctgtgag cggccctgcc  1080
aggtgcctga ccagagcag gaacctgctg aagaccaccg acgacatggt gaagaccgcc  1140
agggagaagc tgaagcacta cagctgcacc gccgaggaca tcgaccacga ggacatcacc  1200
agggaccaga ccagcacccct gaagacctgc ctgcctctgg agctgcacaa gaacgagagc  1260
tgcctggcca ccaggggagac cagcagcacc accaggggca gctgcctgcc tcctcagaag  1320
accagcctga tgatgacccct gtgccttggg t                                1351
```

```
SEQ ID NO: 20           moltype = DNA   length = 284
FEATURE                 Location/Qualifiers
misc_feature            1..284
                        note = sequence of truncatedregion II ofIL12
source                  1..284
                        mol_type = other DNA
                        organism = synthetic construct
SEQUENCE: 20
ctatctacga ggacctgaag atgtaccaga ccgagttcca ggccatcaac gccgccctgc    60
agaaccacaa tcaccagcag atcatcctgg acaagggcat gctggtggcc atcgacgagc   120
tgatgcagag cctgaaccac aacgcgaga ccctgaggca gaagcctcct gtgggcgagg   180
ccgacccta cagggtgaag atgaagctgt gcatcctgct gcacgccttc agcaccaggg   240
tggtgaccat caacagggtg atgggctacc tgagcagcgc ctga                    284
```

```
SEQ ID NO: 21           moltype = DNA   length = 699
FEATURE                 Location/Qualifiers
misc_feature            1..699
                        note = sequence of truncatedregion I ofFLAG-con1-SPOP167-274
source                  1..699
                        mol_type = other DNA
```

```
                            organism = synthetic construct
SEQUENCE: 21
atggactaca aggacgacga cgataaggcc agcagcgccg tgctgcagaa gaagatcacc    60
gactacttcc accccaagaa gggcagcggc tctggcagcg gaagcgtgaa catcagcggc   120
cagaacacca tgaacatggt gaaggtgccc gagtgcgaca tggccgacga gctgggcgac   180
ctgtgggaga acagcaggtt caccgactgc tgcctgtgcg tggccggcca ggagttccaa   240
gcccacaagg ccatcctggc cgccaggagc cccgtgttca cgccatgtt cgagcacgag    300
atggaggaga gcaagaagaa cagagtggag atcaacgacg tggagcccga ggtgttcaag   360
gagatgatgt gcttcatcta caccggcaag gcccccaacc tggacaagat ggccgacgac   420
ctgctggccg ccgccgacaa gtacgccctg gagagactga aggtgatgtg cgaggacgac   480
ctgtgcagca acctgagcgt ggagaacgcc gccgagatcc tcatcctggc cgacctgcac   540
agcgccgacc agctgaagac ccaggccgtg gacttcatca actaccacgc cagcgacgtg   600
ctggagacca gcggctggaa gagcatggtg gtgagccacc cccacctggt ggccgaggcc   660
tacaggagcc tggccagcgc ccagtgcccc ttcttgggt                          699

SEQ ID NO: 22           moltype = DNA   length = 30
FEATURE                 Location/Qualifiers
misc_feature            1..30
                        note = sequence of truncatedregion II
                         ofFLAG-con1-SPOP167-274
source                  1..30
                        mol_type = other DNA
                        organism = synthetic construct
SEQUENCE: 22
cctcccagga agagactgaa gcagagctga                                    30

SEQ ID NO: 23           moltype = DNA   length = 20
FEATURE                 Location/Qualifiers
misc_feature            1..20
                        note = primer sequence
source                  1..20
                        mol_type = other DNA
                        organism = synthetic construct
SEQUENCE: 23
tacttgtcga tcagggtgct                                               20

SEQ ID NO: 24           moltype = DNA   length = 20
FEATURE                 Location/Qualifiers
misc_feature            1..20
                        note = primer sequence
source                  1..20
                        mol_type = other DNA
                        organism = synthetic construct
SEQUENCE: 24
tggacagcaa gaccgactac                                               20

SEQ ID NO: 25           moltype = DNA   length = 20
FEATURE                 Location/Qualifiers
misc_feature            1..20
                        note = primer sequence
source                  1..20
                        mol_type = other DNA
                        organism = synthetic construct
SEQUENCE: 25
ctgcatcagc tcgtcgatgg                                               20

SEQ ID NO: 26           moltype = DNA   length = 22
FEATURE                 Location/Qualifiers
misc_feature            1..22
                        note = primer sequence
source                  1..22
                        mol_type = other DNA
                        organism = synthetic construct
SEQUENCE: 26
tactacaaca gcagctgcag ca                                            22

SEQ ID NO: 27           moltype = DNA   length = 754
FEATURE                 Location/Qualifiers
misc_feature            1..754
                        note = sequence of truncatedregion II
                         ofFLAG-con1-SPOP167-274
source                  1..754
                        mol_type = other DNA
                        organism = synthetic construct
SEQUENCE: 27
ctttaccgac aagaccagcg ccaccgtgat ctgcaggaag aacgccagca tcagcgtgag    60
ggcccaggac aggtactaca gcagcagctg gagcgagtgg gccagcgtgc cctgcagcgg   120
cagcagcggc ggcgggggca gccccggcgg cggcagcagc aggaacctgc cgtggccac    180
ccctgatccc ggaatgttcc cttgcctgca ccacagccag aacctgctga ggccgtgag    240
```

```
caacatgctg cagaaggcca ggcagaccct ggagttctac ccctgcacca gcgaggagat   300
cgaccacgag gacatcacca aggacaagac cagcaccgtg gaggcctgtc tgcccttgga   360
gctgaccaag aacgagagct gcctgaacag cagggagacc agcttcatca ccaacggcag   420
ctgcctggcc agcaggaaga ccagcttcat gatggccctg tgcctgagca gcatctacga   480
ggacctggac atgtaccagg tggagttcaa gaccatgaac gccaagctgc tgatggaccc   540
caagaggcag atcttcctgg accagaacat gctggccgtg atcgacgagc tgatgcaggc   600
cctgaacttc aacagcgaga ccgtgcccca agagcagcc ctggaggagc ccgacttcta   660
caagaccaag atcaagctgt gcatcctgct gcacgccttc aggatcagag ccgtgaccat   720
cgacagggtg atgagctacc tgaacgccag ctga                               754

SEQ ID NO: 28          moltype = DNA   length = 866
FEATURE                Location/Qualifiers
misc_feature           1..866
                       note = sequence of truncatedregion I ofFLAG-con1-SPOP167-274
source                 1..866
                       mol_type = other DNA
                       organism = synthetic construct
SEQUENCE: 28
atgtgccacc agcagctggt gatcagctgg ttcagcctgg tgttcctggc cagccccctg    60
gtggccatct gggagctgaa gaaggacgtg tacgtggtgg agctggactg gtaccccgac   120
gcccccggcg agatggtggt gctgacctgc gacacccccg aggaggacgg catcacctgg   180
accctggacc agagcagcga ggtgctgggc agcggcaaga ccctgaccat ccaggtgaag   240
gagttcggcg acgccggcca gtacacctgc cacaagggcg cgaggtgct gagccacagc   300
ctgctgctgc tccacaagaa ggaggacggc atctggagca ccgacatcct gaaggaccag   360
aaggagccca gaacaagac cttcctgagg tgcgaggcca gaactacag cggcaggttc   420
acctgctggt ggctgaccac catcagcacc gacctgctgc tcagcgtgaa gagcagcgag   480
ggcagcagcg accccagggc gtgacctgc ggcgctgcca cattgtctgc tgaaagggtt   540
agaggcgaca caaggagta cgaatacagc gtggagtgcc aggaggacag cgcctgcccc   600
gccgccgagg agagcctgcc catcgaggtg atggtggacg ccgtgcacaa gctgaagtac   660
gagaactaca ccagcagctt cttcatcagg gacatcatca gcccgaccc tcccaagaac   720
ctgcagctga agccctgaa gaacagcagg caggtggagg tgagctggga gtaccccgac   780
acctggagca cccctcacag ctacttcagc ctgaccttct gcgtgcaggt ccagggcaag   840
agcaagcggg agaagaagga tcgggt                                        866

SEQ ID NO: 29          moltype = DNA   length = 1283
FEATURE                Location/Qualifiers
misc_feature           1..1283
                       note = sequence of truncatedregion II
                        ofFLAG-con1-SPOP167-274
source                 1..1283
                       mol_type = other DNA
                       organism = synthetic construct
SEQUENCE: 29
ctaccgacat cctgaaggac cagaaggagc ccaagaacaa gaccttcctg aggtgcgagg    60
ccaagaacta cagcggcagg ttcacctgct ggtggctgac caccatcagc accgacctga   120
ccttcagcgt gaagagcagc aggggcagca gcgaccccca gggcgtgacc tgcggcgctg   180
ccacattgtc tgctgaaagg gttagaggcg acaacaagga gtacgaatac agcgtggagt   240
gccaggagga cagcgcctgc cccgccgccg aggagagcct gcccatcgag gtgatggtga   300
acgccgtgca aagctgaag tacgagaact acaccagcag cttcttcatc agggacatca   360
tcaagcccga ccctcccaag aacctgcagc tgaagcccct gaagaacagc aggcaggtgg   420
aggtgagctg ggagtacccc gacacctgga gcacccctca gctacttc agcctgacct   480
tctgcgtgca ggtccagggc aagagcaagc gggagaagaa ggacagggtg ttcaccgaca   540
agaccagcgc caccgtgatc tgcaggaaga cgccagcat cagcgtgagg cccaggaca   600
ggtactacag cagcagctgg agcgagtggg ccagcgtgcc ctgcagcggc agcagcggcg   660
gcggggcag ccccggccgc ggcagcagca ggaacctgcc cgtggccacc cctgatcccg   720
gaatgttccc ttgcctgcac cacagcagaa acctgctgag ggccgtgagc aacatgctgc   780
agaaggccag gcagaccctg gagttctacc ccctgcacca gcgaggagatc gaccacgagg   840
acatcaccaa ggacaagacc agcaccgtgg aggcctgtct gcccttggag ctgaccaaga   900
acgagagctg cctgaacagc agggagacca gcttcatcac caacggcagc tgcctggcca   960
gcaggaagac cagcttcatg atggccctgt gcctgagcag catctacgag gacctggaga  1020
tgtaccaggt ggagttcaag accatgaacg ccaagctgct gatggacccc aagaggcaga  1080
tcttcctgga ccagaacatg ctggccgtga tcgacgagct gatgcaggcc ctgaacttca  1140
acagcgagac cgtgccccag aagagcagcc tggaggagcc cgacttctac aagaccaaga  1200
tcaagctgtg catcctgctg cacgccttca ggatcagagc cgtgaccatc gacagggtga  1260
tgagctacct gaacgccagc tga                                          1283

SEQ ID NO: 30          moltype = DNA   length = 337
FEATURE                Location/Qualifiers
misc_feature           1..337
                       note = sequence of truncatedregion I ofFLAG-con1-SPOP167-274
source                 1..337
                       mol_type = other DNA
                       organism = synthetic construct
SEQUENCE: 30
atgtgccacc agcagctggt gatcagctgg ttcagcctgg tgttcctggc cagccccctg    60
gtggccatct gggagctgaa gaaggacgtg tacgtggtgg agctggactg gtaccccgac   120
gcccccggcg agatggtggt gctgacctgc gacacccccg aggaggacgg catcacctgg   180
accctggacc agagcagcga ggtgctgggc agcggcaaga ccctgaccat ccaggtgaag   240
gagttcggcg acgccggcca gtacacctgc cacaagggcg cgaggtgct gagccacagc   300
```

```
ctgctgctgc tccacaagaa ggaggacggc atttggt                              337
```

SEQ ID NO: 31           moltype = DNA   length = 599
FEATURE                 Location/Qualifiers
misc_feature            1..599
                        note = sequence of truncatedregion II
                          ofFLAG-con1-SPOP167-274
source                  1..599
                        mol_type = other DNA
                        organism = synthetic construct
SEQUENCE: 31
```
ctagcaggaa cctgcccgtg gccacccctg atcccggaat gttcccttgc ctgcaccaca    60
gccagaacct gctgagggcc gtgagcaaca tgctgcagaa ggccaggcag accctggagt   120
tctaccccctg caccagcgag gagatcgacc acgaggacat caccaaggac aagaccagca  180
ccgtggaggc ctgtctgccc ttggagctga ccaagaacga gagctgcctg aacagcaggg   240
agaccagctt catcaccaac ggcagctgcc tggccagcag gaagaccagc ttcatgatgg   300
ccctgtgcct gagcagcatc tacgaggacc tgaagatgta ccaggtggag ttcaagacca   360
tgaacgccaa gctgctgatg gaccccaaga ggcagatctt cctggaccag aacatgctga   420
ccgtgatcga cgagctgatg caggccctga acttcaacag cgagaccgtg ccccagaaga   480
gcagcctgga ggagcccgac ttctacaaga ccaagatcaa gctgtgcatc ctgctgcacg   540
ccttcaggat cagagccgtg accatcgaca gggtgatgag ctacctgaac gccagctga   599
```

SEQ ID NO: 32           moltype = DNA   length = 1021
FEATURE                 Location/Qualifiers
misc_feature            1..1021
                        note = sequence of truncatedregion I ofFLAG-con1-SPOP167-274
source                  1..1021
                        mol_type = other DNA
                        organism = synthetic construct
SEQUENCE: 32
```
atgtgccacc agcagctggt gatcagctgg ttcagcctgg tgttcctggc cagcccctg     60
gtggccatct gggagctgaa gaaggacgtg tacgtggtgg agctggactg gtaccccgac   120
gccccggcg agatggtggt gctgacctgc gacacccccg aggaggacgg catcacctgg   180
accctggacc agagcagcga ggtgctgggc agcggcaaga ccctgaccat ccaggtgaag   240
gagttcggcg acgccggcca gtacacctgc cacaagggcg cgaggtgct gagccacagc   300
ctgctgctgc tccacaagaa ggaggacggc atctggagca ccgacatcct gaaggaccag   360
aaggagccca gaacaagac cttcctgagg tgcgaggcca gaactacag cggcaggttc    420
acctgctggt ggctgaccac catcagcacc gacctgacct tcagcgtgaa gagcagcagg   480
ggcagcagga accccaggg cgtgacctgc ggcgctgcca cattgtctgc tgaaagggtt   540
agaggcgaca acaaggagta cgaatacagc gtggagtgcc aggaggacag cgcctgcccc   600
gccgccgagg agagcctgcc catcgagtg atggtggacg ccgtgcacaa gctgaagtac   660
gagaactaca ccagcagctt cttcatcagg gacatcatca gcccgaccc tcccaagaac   720
ctgcagctga agccccgtgaa gaacagcagg caggtgaagg tgagctggga gtaccccgac   780
acctggagca ccccctcacag ctacttcagc ctgaccttct gcgtgcaggt ccagggcaag   840
agcaagcggg agaagaagga cagggtgttc accgacaaga ccagcgccac cgtgatctgc   900
aggaagaacg ccagcatcag cgtgagggcc caggacaggt actacagcag cagctggagc   960
gagtgggcca gcgtgcctg cagcggcagc agcgcggcc ggcagccc cggcggtggg       1020
t                                                                   1021
```

SEQ ID NO: 33           moltype = DNA   length = 335
FEATURE                 Location/Qualifiers
misc_feature            1..335
                        note = sequence of truncatedregion II
                          ofFLAG-con1-SPOP167-274
source                  1..335
                        mol_type = other DNA
                        organism = synthetic construct
SEQUENCE: 33
```
cttgcctggc cagcaggaag accagcttca tgatggccct gtgcctgagc agcatctacg    60
aggacctgaa gatgtaccag gtggagttca gaccatgaa cgccaagctg ctgatggacc   120
ccaagaggca gatcttcctg gaccagaaca tgctggccgt gatcgacgag ctgatgcagg   180
ccctgaactt caacagcgag accgtgcccc agaagagcag cctggaggag cccgacttct   240
acaagaccaa gatcaagctg tgcatcctgc tgcacgcctt caggatcaga gccgtgacca   300
tcgacagggt gatgagctac ctgaacgcca gctga                              335
```

SEQ ID NO: 34           moltype = DNA   length = 1285
FEATURE                 Location/Qualifiers
misc_feature            1..1285
                        note = sequence of truncatedregion I ofFLAG-con1-SPOP167-274
source                  1..1285
                        mol_type = other DNA
                        organism = synthetic construct
SEQUENCE: 34
```
atgtgccacc agcagctggt gatcagctgg ttcagcctgg tgttcctggc cagcccctg     60
gtggccatct gggagctgaa gaaggacgtg tacgtggtgg agctggactg gtaccccgac   120
gccccggcg agatggtggt gctgacctgc gacacccccg aggaggacgg catcacctgg   180
accctggacc agagcagcga ggtgctgggc agcggcaaga ccctgaccat ccaggtgaag   240
gagttcggcg acgccggcca gtacacctgc cacaagggcg cgaggtgct gagccacagc   300
ctgctgctgc tccacaagaa ggaggacggc atctggagca ccgacatcct gaaggaccag   360
```

-continued

```
aaggagccca agaacaagac cttcctgagg tgcgaggcca agaactacag cggcaggttc    420
acctgctggt ggctgaccac catcagcacc gacctgacct tcagcgtgaa gagcagcagg    480
ggcagcagcg accccagggc cgtgacctgc ggcgctgcca cattgtctgc tgaaagggtt    540
agaggcgaca caaggagta cgaatacagc gtggagtgcc aggaggacag cgcctgcccc     600
gccgccgagg agagcctgcc catcgaggtg atggtggacg ccgtgcacaa gctgaagtac    660
gagaactaca ccagcagctt cttcatcagg gacatcatca gcccgaccc tcccaagaac     720
ctgcagctga agcccctgaa gaacagcagg caggtggagg tgagctggga gtaccccgac    780
acctggagca ccctcacag ctacttcagc ctgaccttct gcgtgcaggt ccagggcaag     840
agcaagcggg agaagaagga cagggtgttc accgacaaga ccagcgccac cgtgatctgc    900
aggaagaacg ccagcatcag cgtgagggcc caggacaggt actacagcag cagctggacg    960
gagtgggcca gcgtgccctg cagcggcagc agcggcggcg gggcagccc cggcggcggc    1020
agcagcagga acctgcccgt ggccacccct gatcccggaa tgttcccttg cctgcaccac    1080
agccagaacc tgctgagggc cgtgagcaac atgctgcaga aggccaggca gaccctggag    1140
ttctacccct gcaccagcga ggagatcgac acgaggaca tcaccaagga caagaccagc     1200
accgtggagg cctgtctgcc cttggagctg accaagaacg agagctgcct gaacagcagg    1260
gagaccagct tcatcaccaa tgggt                                          1285

SEQ ID NO: 35          moltype = DNA  length = 1409
FEATURE                Location/Qualifiers
misc_feature           1..1409
                       note = sequence of truncatedregion II
                       ofFLAG-con1-SPOP167-274
source                 1..1409
                       mol_type = other DNA
                       organism = synthetic construct
SEQUENCE: 35
ctggcaagac cctgaccatc caggtgaagg agttcggcga cgccggccag tacacctgcc     60
acaagggcgg cgaggtgctg agccacagcc tgctgctgct ccacaagaag gaggacggca    120
tctggagcac cgacatcctg aaggaccaga aggagcccaa gaacaagacc ttcctgaggt    180
gcgaggccaa gaactacagc ggcaggttca cctgctgctg gctgaccacc atcagcaccg    240
acctgacctt cagcgtgaag agcagcaggg cagcagcga ccccagggc gtgacctgcg     300
gcgctgccac attgtctgct gaaagggtta gaggcgacaa caaggagtac gaatacagcg    360
tggagtgcca ggaggacagc gcctgccccg ccgccgagga gagcctgccc atcgaggtga    420
tggtggacgc cgtgcacaag ctgaagtacg agaactacac cagcagcttc ttcatcaggg    480
acatcatcaa gcccgaccct cccaagaacc tgcagctgaa gcccctgaag aacagcaggc    540
aggtggaggt gagctgggag taccccgaca cctggagcac ccctcacagc tacttcagcc    600
tgaccttctg cgtgcaggtc cagggcaaga gcaagcggga agaaggac agggtgttca     660
ccgacaagac cagcgccacc gtgatctgca ggaagaacgc cagcatcagc gtgagggccc    720
aggacagta ctacagcagc agctggagcg agtgggccag cgtgccctgc agcggcagca    780
gcggcggcgg gggcagcccc ggcggcggca gcagcaggaa cctgcccgtg ccacccctg    840
atcccggaat gttcccttgc ctgcaccaca gccagaacct gctgagggcc gtgagcaaca    900
tgctgcagaa ggccaggcag accctggagt tctacccctg caccagcgag gagatcgacc    960
acgaggacat caccaaggac aagaccagcc cgtggaggcc ctgtctgccc ttggagctga   1020
ccaagaacga gagctgcctg aacagcaggg agaccagctt catcaccaac ggcagctgcc    1080
tggccagcag gaagaccagc ttcatgatgg ccctgtgcct gagcagcatc tacgaggacc    1140
tgaagatgta ccaggtggag ttcaagacca tgaacgccaa gctgctgatg accccaaga    1200
ggcagatctt cctggaccaa aacatgctgg ccgtgatcga ctgcaggtg caggccctga    1260
acttcaacag cgagaccgtg ccccagaaga gcagcctgga ggagcccgac ttctacaaga    1320
ccaagatcaa gctgtgcatc ctgctgcacg ccttcaggat cagagccgtg accatcgaca    1380
gggtgatgag ctacctgaac gccagctga                                      1409

SEQ ID NO: 36          moltype = DNA  length = 211
FEATURE                Location/Qualifiers
misc_feature           1..211
                       note = sequence of truncatedregion I ofFLAG-con1-SPOP167-274
source                 1..211
                       mol_type = other DNA
                       organism = synthetic construct
SEQUENCE: 36
atgtgccacc agcagctggt gatcagctgg ttcagcctgg tgttcctggc agcccctg      60
gtggccatct gggagctgaa gaaggacgtg tacgtggtgg agctggactg taccccgac    120
gccccggcg agatggtggt gctgacctgc gacacccccg aggaggacgg catcacctgg    180
accctggacc agagcagcga ggtgcttggg t                                   211

SEQ ID NO: 37          moltype = RNA  length = 60
FEATURE                Location/Qualifiers
misc_feature           1..60
                       note = sequence of S1m
source                 1..60
                       mol_type = other RNA
                       organism = synthetic construct
SEQUENCE: 37
atgcggccgc cgaccagaat catgcaagtg cgtaagatag tcgcgggtcg gcggccgcat    60

SEQ ID NO: 38          moltype = DNA  length = 1464
FEATURE                Location/Qualifiers
misc_feature           1..1464
                       note = sequence of circular RNA
source                 1..1464
```

```
                        mol_type = other DNA
                        organism = synthetic construct
SEQUENCE: 38
ctgtgcaact tgcagatcac taccaacaga atacgccgat aggagatgga cctgtgcttc    60
ttcctgataa ccactacctt tcaacacaat cagcactttc aaaggaccca aacgagaagc   120
gagaccacat ggtgcttctt gaatttgtga cagcagcagg aatcacactt ggaatggatg   180
aactttacaa atgaggttat aacagcctgt gggttgatcc cacccacagg gcccactggg   240
cgctagcact ctggtatcac ggtacctttg tgcgcctgtt ttatacttcc tcccccaact   300
gcaacttaga agtaacacaa accgatcaac agtcagcgtg gcacaccagc cacgttttga   360
tcaaacactt ctgttacccc ggactgagta tcaatagact gctcacgcgg ttgaaggaga   420
aaacgttcgt tatccggcca actacttcga gaaacctagt aacgcatgg aagttgtgga    480
gtgtttcgct cagcactacc ccagtgttga tcaggttgtt gagtcaccgc attcccacg    540
ggtgtccgtg gcgtggctg cgttggcggc ctgcccatgg ggaaacccat gggacgctct    600
tatacagaca tggtgcgaag agtctattga gcttgttggt agtcctccgg ccctgaatg    660
cggctaatcc caactgcgga gcatacactc tcaagccaga gggtagtgtg tcgtattggg   720
caactctgca gcggaaccga ctactttggg tgtccgtgtt tcattttatt cctatactgg   780
ctgcttatgg tgacaattgt gagattgtta ccataaagct attggattgg ccatccggtg   840
actatcagag ctattatata tcttttgtt gggtttatac cactaagctt gaaagaggtt    900
ataactctac attacatttt aatactgaac accgcaaaat ggtgtcaaag ggtgaggaat   960
tattcaccgg cgtggtgcct atccttgtgg aacttgatgg agatgtgaac ggacacaaat  1020
tcagtgtatc aggagaagga gaaggagatg caacatacgg aaagctcact cttaaattta  1080
tctgcacaac aggaaagctc ccggtgcctt ggcctacact tgtgacaaca cttacatacg  1140
gagtgcaatg cttctcgcgt taccctgatc acatgaaaca acacgatttc ttcaagagtg  1200
caatgcctga aggatacgtg caagaaagaa caatcttctt caaggacgat ggaaactaca  1260
agactcgtgc agaagtgaaa tttgaaggag atacacttgt gaacagaatc gaacttaaag  1320
gaatcgattt caaggaggat ggaaacatcc ttggacacaa acttgaatac aactacaact  1380
cacacaacgt gtacatcatg gcagataaac agaagaatgg tatcaaagtg aactttaaga  1440
ttcgccacaa catcgaagat gggt                                         1464

SEQ ID NO: 39          moltype = DNA  length = 1639
FEATURE                Location/Qualifiers
misc_feature           1..1639
                       note = sequence of circular RNA
source                 1..1639
                       mol_type = other DNA
                       organism = synthetic construct
SEQUENCE: 39
aaaatccgtt gaccttaaac ggtcgtgtgg gttcaagtcc ctccaccccc acgccggaaa    60
cgcaatagcc gaaaaaacaa aacaaaaaaa caaaaaaaaa accaaaaacac              120
attaaaacag cctgtgggtt gatcccaccc cagggcccca ctgggcgcta gcactctggt   180
atcacggtac ctttgtgcgc ctgttttata cttcctcccc caactgcaac ttagaagtaa   240
cacaaaccga tcaacagtca gcgtggcaca ccagccacgt tttgatcaaa cacttctgtt   300
accccggact gagtatcaat agactgctca gcggttgaa ggagaaaacg ttcgttatcc    360
ggccaactac ttcgagaaac ctagtaacgc catggaagtt gtggagtgtt tcgctcagca   420
ctaccccagt gtagatcagg ttgatgagtc accgcattcc cacgggtga ccgtggcggt   480
ggctgcgttg gcgcgcctgcc catggggaaa cccatgggac gctcttatac agacatggtg   540
cgaagagtct attgagctag ttggtagtcc tccggcccc gaatgcggct aatcccaact    600
gcggagcata cactctcaag ccagagggta gtgtgtcgta atgggcaact ctgcagcgga   660
accgactact ttgggtgtcc gtgtttcatt ttattcctat actggctgct tatggtgaca   720
attgagagat tgttaccata tagctattgg attgccatc cggtgactaa cagagctatt    780
atatatcttt ttgttgggtt tataccactt agcttgaaag aggttaaaac tctacattac   840
atttaatac tgaacaccgc aaaatggtgt caaagggtga ggaattattc accggcgtgt    900
tgcctatcct tgtggaactt gatggagatg tgaacggaca caaattcagt gtatcaggag   960
aaggagaagg agatgcaaca tacggaaagc tcactcttaa atttatctgc acaacaggaa  1020
agctcccggt gccttggcct acacttgtga acacttacg atacggagtg caatgcttct    1080
cgcgttaccc tgatcacatg aaacaacacg atttcttcaa gagtgcaatg cctgaaggat  1140
acgtgcaaga agaacaatc ttcttcaagg acgatggaaa ctacaagact cgtgcagaag    1200
tgaaatttga aggagataca cttgtgaaca gaatcgaact taaggaatc gatttcaagg    1260
aggatggaaa catccttgga cacaaacttg aatacaacta caactcacac aacgtgtaca  1320
tcatggcaga taaacagaag aatggtatca aagtgaactt taagattcgc cacaacatcg  1380
aagatggatc agtgcaactt gcagatcact accaacagaa tacgccgata ggagatggac  1440
ctgtgcttct tcctgataac cactaccttt caacacaatc agcactttca aaggacccaa  1500
acgagaagcg agaccacatg gtgcttcttg aatttgtgac agcagcagga atcacacttg  1560
gaatggatga actttacaaa tgaaaaaac aaaaaacaaa acggcatatt a tgcgttaccg  1620
gcgagacgct acggactta                                               1639

SEQ ID NO: 40          moltype = DNA  length = 3267
FEATURE                Location/Qualifiers
misc_feature           1..3267
                       note = sequence of circular RNA
source                 1..3267
                       mol_type = other DNA
                       organism = synthetic construct
SEQUENCE: 40
ctgtgcaact tgcagatcac taccaacaga atacgccgat aggagatgga cctgtgcttc    60
ttcctgataa ccactacctt tcaacacaat cagcactttc aaaggaccca aacgagaagc   120
gagaccacat ggtgcttctt gaatttgtga cagcagcagg aatcacactt ggaatggatg   180
aactttacaa aggaagcgga gctactaact tcagcctgct gaagcaggct ggagacgtgg   240
aggagaaccc tggacctgga agcggggagg acgccaagaa catcaagaag ggccctgccc   300
```

```
ctttctaccc tctggaggac ggcaccgccg gcgagcagct gcacaaggcc atgaagaggt   360
acgccctggt gcctggcacc atcgccttca ccgacgccca catcgaggtg gacatcacct   420
acgccgagta cttcgagatg agcgtgaggc tggccgaggc catgaagagg tacgcctga    480
acaccaacca caggatcgtg gtgtgcagcg agaacagcct gcagttcttc atgcctgtgc   540
tgggcgccct gttcatcggc gtggccgtgg cccctgccaa cgacatctac aacgagaggg   600
agctgctgaa cagcatgggc atcagccagc ctaccgtggt gttcgtgagc aagaagggcc   660
tgcagaagat cctgaacgtg cagaagaagc tgcctatcat ccagaagatc atcatcatgg   720
acagcaagac cgactaccag ggcttccaga gcatgtacac cttcgtgacc agccacctgc   780
ctcctggctt caacgagtac gacttcgtgc ctgagagctt cgacagggac aagaccatcg   840
ccctgatcat gaacgagcag ggcagcaccg gcctgcctaa gggcgtggcc ctgcctcaca   900
ggaccgcctg cgtgaggttc agccacgcca gggaccctat cttcggcaac cagatcatcc   960
ctgacaccgc catcctgagc gtggtgcctt ccaccacgg cttcggcatg ttcaccaccc   1020
tgggctacct gatctgcggc ttcagggtgg tgctgatgta caggttcgag gaggagctgt   1080
tcctgaggag cctgcaggac tacaagatcc agagcgcct gctggtgcct accctgttca   1140
gcttcttcgc caagagcacc ctgatcgaca agtacgacct gagcaacctg cacgagatcg   1200
ccagcggcga cgcccctctg agcaaggagg tgggcgaggc cgtggccaag aggttccacc   1260
tgcctggcat caggcagggc tacggcctga ccgagaccac cagcgccatc ctgatcaccc   1320
ctgagggcga cgacaagcct ggcgccgtgg gcaaggtggt gcctttcttc gaggccaagg   1380
tggtggacct ggacaccggc aagacctg gcgtgaacca gaggggcgag ctgtgcgtga   1440
ggggccctat gatcatgagc ggctacgtga caaaccctga ggccaccaac gccctgatcg   1500
acaaggacgg ctggctgcac agcggcgaca tcgcctactg ggacgaggac gagcacttct   1560
tcatcgtgga caggctgaag agcctgatca gtacaaggg ctaccaggtg gcccctgccg   1620
agctggagag catcctgctg cagcacccta acatcttcga cgccggcgtg gctggcttgc   1680
ctgatgacga tgctgagag ctgcctgccg ccgtggtggt gctggagcac ggcaagacca   1740
tgaccgagaa ggagatcgtg gactacgtgg ccagccaggt gaccaccgcc aagaagctga   1800
ggggcgcgt ggtgttcgtg gacgaggtgc ctaagggct gaccgccaag ctggacgcca   1860
ggaagatcag ggagatcctg atcaaggcca agaaggcgg caagatcgcc gtgtgaggtt   1920
aaaacagcct gtgggttgat cccacccaca gggccactg ggcgctagca ctctggtatc   1980
acggtaccttt tgtgcgcctg ttttataactt cctccccaa ctgcaactta gaagtaacac   2040
aaaccgatca acagtcagcg tggcacacca gccacgtttt gatcaaacac ttctgttacc   2100
ccggactgag tatcaataga ctgctcacgc ggttgaagga gaaaacgttc gttatccggc   2160
caactacttc gagaaaccta gtaacgccat ggaagttgtg gagtgtttcg ctcagcacta   2220
ccccagtgta gatcaggttg atgagtcacc gcattcccca cggtgaccg tggcggtggc   2280
tgcgttggcg gcctgcccat ggggaaaccc atgggacgct cttatacaga catggtgcga   2340
agagtctatt gagctagttg gtagtcctcc ggccctgaa tgcggctaat cccaactgcg   2400
gagcatacac tctcaagcca gagggtagtg tgtcgtaatg ggcaactctg cagcggaacc   2460
gactactttg ggtgtccgtg tttcatttta ttcctatact ggctgcttat ggtgacaatt   2520
gagagattgt taccatatag ctattggatt ggccatccgg tgactaacag agctattata   2580
tatcttttg ttgggtttat accacttagc ttgaaagagg ttaaaactct acattacatt   2640
ttaatactga acaccgcaaa ggagccacca tgggctccgg cgagggcagg ggaagtcttc   2700
taacatgcgg ggacgtggag gaaaatcccg gcccaggctc cggcgtgtca agggtgagg   2760
aattattcac cggcgtggtg cctatccttg tggaacttga tggagatgtg aacggacaca   2820
aattcagtgt atcaggagaa ggagaaggag atgcaacata cggaaagctc actcttaaat   2880
ttatctgcac aacaggaaag ctcccggtgc cttggcctac acttgtgaca cacttacat   2940
acggagtgca atgcttctcg cgttaccctg atcacatgaa acaacacgat ttcttcaaga   3000
gtgcaatgcc tgaaggatac gtgcaagaaa gaacaatctt cttcaaggac gatggaaact   3060
acaagactcg tgcagaagtg aaatttgaag gatacact tgtgaacaga atcgaactta   3120
aaggaatcga tttcaaggag gatggaaaca tccttggaca caaacttgaa tacaactaca   3180
actcacacaa cgtgtacatc atggcagata acagaagaa tggtatcaaa gtgaacttta   3240
agattcgcca acacatcgaa gatgggt                                      3267

SEQ ID NO: 41          moltype = DNA   length = 3752
FEATURE                Location/Qualifiers
misc_feature           1..3752
                       note = sequence of circular RNA
source                 1..3752
                       mol_type = other DNA
                       organism = synthetic construct
SEQUENCE: 41
ctgtgcaact tgcagatcac taccaacaga atacgccgat aggagatgga cctgtgcttc   60
ttcctgataa ccactacctt tcaacacaat cagcactttc aaaggaccca acgagaagc    120
gagaccacat ggtgcttctt gaatttgtga cagcagcagg aatcacactt ggaatggatg   180
aactttacaa atgaacgtta ctggccgaag ccgcttggaa caaggccggt gtgcgtttgt   240
ctatatgtta ttttccacca tattgccgtc ttttggcaat gtgagggccc ggaaacctgg   300
ccctgtcttc ttgacgagca ttcctagggg tctttcccct ctcgccaaag gaatgcaagg   360
tctgttgaat gtcgtgaagg aagcagttcc tctggaagct tcttgtagac aaacaacgtc   420
tgtagcgacc ctttgcaggc agcggaaccc ccacctggc gacaggtgcc tctgcggcca   480
aaagccacgt gtatacgata cacctgcaaa ggcggcacac cccagtgcc acgttgtgag   540
ttggatagtt gtggaaagag tcaaatggct ctcctcaagc tgattcaaca ggggctgaa    600
ggatgcccag aagtacccc attgtatggg atctgatctg gggcctcggt gcacatgctt   660
tacatgtgtt cagtcgaggt taaaaaacgt ccaggcccc cgaaccacgg ggacgtggtt    720
ttccttgaa aaacacgatg ataatatggc acaaccatg gaggacgcca agaacatcaa   780
gaagggcccc gccccttttct acccctctgga ggacggcacc gccggcagc agctgcacaa   840
ggcatgaaga ggtacggccc tggtgcctgg caccatcgcc ttcaccgacg ccaccatcga   900
ggtggacatc acctacgccg agtacttcga gatgagcgtg aggctggccg aggccatgaa   960
gaggtacggg ctgaacacca accacaggat cgtggtgtgc agcgagaaca gcctgcagtt   1020
cttcatgcct gtgctgggcg ccctgttcat cggcgtggcc gtggcccctg ccaacgacat   1080
ctacaacgag agggagctgc tgaacagcat gggcatcagc agcctaccg tggtgttcgt   1140
gagcaagaag ggcctgcaga gatcctgaa cgtgcagaag aagctgccta tcatccagaa   1200
```

```
gatcatcatc atggacagca agaccgacta ccagggcttc cagagcatgt acaccttcgt  1260
gaccagccac ctgcctcctg gcttcaacga gtacgacttc gtgcctgaga gcttcgacag  1320
ggacaagacc atcgccctga tcatgaacag cagcggcagc accggcctgc ctaagggcgt  1380
ggccctgcct cacaggaccg cctgcgtgag gttcagccac gccagggacc ctatcttcgg  1440
caaccagatc atccctgaca ccgccatcct gagcgtggtg cctttccacc acggcttcgg  1500
catgttcacc accctgggct acctgatctg cggcttcagg gtggtgctga tgtacaggtt  1560
cgaggaggag ctgttcctga ggagcctgca ggactacaag atccagagcg ccctgctggt  1620
gcctaccctg ttcagcttct tcgccaagag caccctgatc gacaagtacg acctgagcaa  1680
cctgcacgag atcgccagcg cggcgcccc tctgagcaag gaggtgggcg aggccgtggc  1740
caagaggttc cacctgcctg gcatcaggca gggctacggc ctgaccgaga ccaccagcgc  1800
catcctgatc accctgagg gcgacgacaa gcctggcgcc gtgggcaagg tggtgccttt  1860
cttcgaggcc aagtggtgg acctggacac cggcaagacc ctgggcgtga accagagggg  1920
cgagctgtgc gtgaggggcc ctatgatcat gagcggctac gtgaacaacc ctgaggccac  1980
caacgccctg atcgacaagg acggctggct gcacagcggc gacatcgcct actgggacga  2040
ggacgagcac ttcttcatcg tggacaggct gaagagcctg atcaagtaca agggctacca  2100
ggtggcccct gccgagctgg agagcatcct gctgcagcac cctaacatct tcgacgccgg  2160
cgtggctggc ttgcctgatg acgatgctgg agagctgcct gccgccgtgg tggtgctgga  2220
gcacggcaag accatgaccg agaaggagat cgtggactac gagcagcc aggtgaccac  2280
cgccaagaag ctgaggggcg gcgtggtgtt cgtggacgag gtgcctaagg gcctgaccgg  2340
caagctggac gccaggaaga tcaggtgagat cctgatcaag gccaagaagg gcggcaagat  2400
cgccgtgtga ggttaaaaca gcctgtgggt tgatcccacc cacagggccc actgggcgct  2460
agcactctgg tatcacggta cctttgtgcg cctgtttat acttcctccc ccaactgcaa  2520
cttagaagta acacaaaccg atcaacagtc agcgtggcac accagccacg ttttgatcaa  2580
acacttctgt taccccggac tgagtatcaa tagactgctc acgcgttga aggagaaaac  2640
gttcgttatc cggccaacta cttcgagaaa cctagtaacg ccatggaagt tgtggagtgt  2700
ttcgctcagc actaccccag tgtagatcag gttgatgagt caccgcattc cccacgggtg  2760
accgtggcgg tggctgcgtt ggcggcctgc ccatggggaa acccatggga cgctcttata  2820
cagacatggt gcgaagagtc tattgagcta gttggtagtc ctccggcccc tgaatgcggc  2880
taatcccaac tgcggagcat acactctcaa gccagagggt agtgtgtcgt aatgggcaac  2940
tctgcagcga aaccgactac tttgggtgtc cgtgtttcat tttattccta tactggctgg  3000
ttatggtgac aattgagaga ttgttaccat atagctattg gattggccat ccggtgacta  3060
acagagctat tatatatctt tttgttgggt ttataccact tagcttgaaa gaggttaaaa  3120
ctctacatta cattttaata ctgaacaccg caaaatgggc tccggcgagg cagggggaag  3180
tcttctaaca tgcggggacg tggaggaaaa tcccggccca ggctccggcg tgtcaaaggg  3240
tgaggaatta ttcaccggcg tggtgcctat ccttgtggaa cttgatggag atgtgaaccgg  3300
acacaaattc agtgtatcag gagaaggaga aggagatgca acatacggaa agctcactct  3360
taaatttatc tgcacaacag gaaagctccc ggtgccttgg cctacacttg tgacaacact  3420
tacatacgga gtgcaatgct tctcgcgtta ccctgatcac atgaaacaac acgatttctt  3480
caagagtgca atgcctgaag gatacgtgca agaaagaaca atcttcttca aggacgatgg  3540
aaactacaag actcgtgcag aagtgaaatt tgaaggagat acacttgtga acagaatcga  3600
acttaaagga atcgatttca aggaggatgg aaacatcctt ggacaaaac ttgaatacaa  3660
ctacaactca cacaacgtgt acatcatggc agataaacag aagaatggta tcaaagtgaa  3720
ctttaagatt cgccacaaca tcgaagatgg gt                                 3752

SEQ ID NO: 42           moltype = DNA   length = 20
FEATURE                 Location/Qualifiers
misc_feature            1..20
                        note = primer sequence
source                  1..20
                        mol_type = other DNA
                        organism = synthetic construct
SEQUENCE: 42
tgggaggatt ctgcattacc                                                  20

SEQ ID NO: 43           moltype = DNA   length = 18
FEATURE                 Location/Qualifiers
misc_feature            1..18
                        note = primer sequence
source                  1..18
                        mol_type = other DNA
                        organism = synthetic construct
SEQUENCE: 43
cagcatcgct ggttgaga                                                    18

SEQ ID NO: 44           moltype = DNA   length = 20
FEATURE                 Location/Qualifiers
misc_feature            1..20
                        note = primer sequence
source                  1..20
                        mol_type = other DNA
                        organism = synthetic construct
SEQUENCE: 44
ctcccggcac agaagtgtat                                                  20

SEQ ID NO: 45           moltype = DNA   length = 20
FEATURE                 Location/Qualifiers
misc_feature            1..20
                        note = primer sequence
source                  1..20
```

```
                            mol_type = other DNA
                            organism = synthetic construct
SEQUENCE: 45
cttcctctgc ctctggtttg                                               20

SEQ ID NO: 46               moltype = DNA   length = 20
FEATURE                     Location/Qualifiers
misc_feature                1..20
                            note = primer sequence
source                      1..20
                            mol_type = other DNA
                            organism = synthetic construct
SEQUENCE: 46
ccatctctgt cctccatgag                                               20

SEQ ID NO: 47               moltype = DNA   length = 20
FEATURE                     Location/Qualifiers
misc_feature                1..20
                            note = primer sequence
source                      1..20
                            mol_type = other DNA
                            organism = synthetic construct
SEQUENCE: 47
atttctgctc tgacaacctc                                               20

SEQ ID NO: 48               moltype = DNA   length = 20
FEATURE                     Location/Qualifiers
misc_feature                1..20
                            note = primer sequence
source                      1..20
                            mol_type = other DNA
                            organism = synthetic construct
SEQUENCE: 48
tgcaaaatgg gacagaaaga                                               20

SEQ ID NO: 49               moltype = DNA   length = 20
FEATURE                     Location/Qualifiers
misc_feature                1..20
                            note = primer sequence
source                      1..20
                            mol_type = other DNA
                            organism = synthetic construct
SEQUENCE: 49
tgattcagaa gcgagtgtgc                                               20

SEQ ID NO: 50               moltype = DNA   length = 20
FEATURE                     Location/Qualifiers
misc_feature                1..20
                            note = primer sequence
source                      1..20
                            mol_type = other DNA
                            organism = synthetic construct
SEQUENCE: 50
accaaataca ggagccatgc                                               20

SEQ ID NO: 51               moltype = DNA   length = 20
FEATURE                     Location/Qualifiers
misc_feature                1..20
                            note = primer sequence
source                      1..20
                            mol_type = other DNA
                            organism = synthetic construct
SEQUENCE: 51
gcgatttcct tcttttgcag                                               20

SEQ ID NO: 52               moltype = DNA   length = 20
FEATURE                     Location/Qualifiers
misc_feature                1..20
                            note = primer sequence
source                      1..20
                            mol_type = other DNA
                            organism = synthetic construct
SEQUENCE: 52
cgtctcctac cagaccaagg                                               20

SEQ ID NO: 53               moltype = DNA   length = 20
FEATURE                     Location/Qualifiers
misc_feature                1..20
                            note = primer sequence
```

```
source                  1..20
                        mol_type = other DNA
                        organism = synthetic construct
SEQUENCE: 53
ccaaagtaga cctgcccaga                                           20

SEQ ID NO: 54           moltype = DNA  length = 20
FEATURE                 Location/Qualifiers
misc_feature            1..20
                        note = primer sequence
source                  1..20
                        mol_type = other DNA
                        organism = synthetic construct
SEQUENCE: 54
taccccagg agaagattcc                                            20

SEQ ID NO: 55           moltype = DNA  length = 20
FEATURE                 Location/Qualifiers
misc_feature            1..20
                        note = primer sequence
source                  1..20
                        mol_type = other DNA
                        organism = synthetic construct
SEQUENCE: 55
gccatctttg gaaggttcag                                           20

SEQ ID NO: 56           moltype = DNA  length = 2514
FEATURE                 Location/Qualifiers
misc_feature            1..2514
                        note = sequence of circular RNA
source                  1..2514
                        mol_type = other DNA
                        organism = synthetic construct
SEQUENCE: 56
ttaaaacagc ctgtgggttg atcccaccca cagggcccac tgggcgctag cactctggta   60
tcacggtacc tttgtgcgcc tgttttatac ttcctccccc aactgcaact tagaagtaac  120
acaaaccgat caacagtcag cgtggcacac agccacgtt ttgatcaaac acttctgtta   180
ccccggactg agtatcaata gactgctcac gcggttgaag gagaaaacgt tcgttatccg   240
gccaactact tcgagaaacc tagtaacgcc atggaagttg tggagtgttt cgctcagcga   300
taccccagtg tagatcaggt tgatgagtca ccgcattccc cacgggtgac cgtggcggtg   360
gctgcgttgg cggcctgccc atggggaaac ccatgggacg ctcttataca gacatggtgc   420
gaagagtcta ttgagctagt tggtagtcct ccggcccctg aatgcggcta atcccaactg   480
cggagcatac actctcaagc cagagggtag tgtgtcgtaa tgggcaactc tgcagcgaa   540
ccgactactt tgggtgtccg tgttttcattt tattcctata ctggctgctt atggtgacaa   600
ttgagagatt gttaccatat agctattgga ttggccatcc ggtgactaac agagctatta   660
tatatctttt tgttgggttt ataccactta gcttgaaaga ggttaaaact ctacattaca   720
ttttaatact gaacaccgca aaatgtagga cgccaagaac atcaagaagg gccctgcccc   780
tttctacccct ctggaggacg gcaccgccgg cgagcagctg cacaaggcca tgaagaggta   840
cgccctggtg cctggcacca tcgccttcac cgacgcccac atcgaggtgg acatcaccta   900
cgccgagtac ttcgagatga gcgtgaggct ggccgaggcc atgaagaggt acggcctgaa   960
caccaaccac aggatcgtgg tgtgcagcga gaacagcctg cagttcttca tgcctgtgct  1020
gggcgccctg ttcatcggcg tggccgtggc ccctgccaac gacatctaca acgagaggga  1080
gctgctgaac agcatgggca tcagccagcc taccgtggtg ttcgtgagca gaagggcct   1140
gcagaagatc ctgaacgtgc agaagaagct gcctatcatc cagaagatca tcatcatgga  1200
cagcaagacc gactaccagg gcttccagag catgtacacc ttcgtgacca gccacctgcc  1260
tcctggcttc aacgagtacg acttcgtgcc tgagagcttc gacagggaca agaccatcgc  1320
cctgatcatg aacagcagcg gcagcaccgg cctgcctaag ggcgtggccc tgcctcacag  1380
gaccgcctgc gtgaggttca gccacgccag ggacccatc ttcggcaacc agatcatccc   1440
tgacaccgcc atcctgagcg tggtgccttt ccaccacgtc ttcggcatgt tcaccaccct  1500
gggctacctg atctgcggct tcagggtggt gctgatgtac aggttcgagg aggagctgtt  1560
cctgaggagc ctgcaggact acaagatcca gagcgccctg ctggtgccta ccctgttcag  1620
cttcttcgcc aagagcaccc tgatcgacaa gtacgacctg agcaacctgc acgagatcgc  1680
cagcggcggc gcccctctga gcaaggaggt gggcgaggcc gtggccaaga gttccacct   1740
gcctggcatc aggcagggct acggcctgac cgagaccacc agcgccatcc tgatcaccc   1800
tgagggcgac gacaagcctg cgcgcgtggg caaggtggtg cctttcttcg aggccaaggt  1860
ggtggacctg gacaccggca agaccctggg cgtgaaccag aggggcgagc tgtgcgtgag  1920
gggccctatg atcatgagcg gctacgtgaa caacccgag gccaccaacg ccctgatcga   1980
caaggacggc tggctgcaca gcggcgacat cgcctactgg gacgaggacg agcacttctt  2040
catcgtggac aggctgaaga gcctgatcaa gtacaaggc taccaggtgg cccctgccga   2100
gctggagagc atcctgctgc agcacccctaa catcttcgac gccggcgtgg ctggcttgcc  2160
tgatgacgat gctggagagc tgcctgccgc cgtggtggtg ctggagcacg caagaccat   2220
gaccgagaag gagatcgtgg actacgtggc cagccaggtg accaccgcca agaagctgag  2280
gggcggcgtg gtgttcgtgg acgaggtgcc taagggcctg accggcaagc tggacgccag  2340
gaagatcagg gagatctga tcaaggccaa gaagggcggc aagatctgtg atgata       2400
ataggctgga gcctcggtgg ccatgcttct tgccccttgg gcctccccc agccctcct    2460
cccttcctg cacccgtacc cccgtggtct ttgaataaag tctgagtggg cggc         2514

SEQ ID NO: 57           moltype = DNA  length = 2536
FEATURE                 Location/Qualifiers
```

```
misc_feature            1..2536
                        note = sequence of circular RNA
source                  1..2536
                        mol_type = other DNA
                        organism = synthetic construct
SEQUENCE: 57
ttaaaacagc ctgtgggttg atcccaccca cagggcccac tgggcgctag cactctggta    60
tcacggtacc tttgtgcgcc tgttttatac ttcctccccc aactgcaact tagaagtaac   120
acaaaccgat caacagtcag cgtggcacac cagccacgtt ttgatcaaac acttctgtta   180
ccccggactg agtatcaata gactgctcac gcggttgaag gagaaaacgt tcgttatccg   240
gccaactact tcgagaaacc tagtaacgcc atggaagttg tggagtgttt cgctcagcac   300
tacccagtg tagatcaggt tgatgagtca ccgcattccc cacgggtgac cgtggcggtg   360
gctgcgttgg cggcctgccc atggggaaac ccatgggacg ctcttataca gacatggtgc   420
gaagagtcta ttgagctagt tggtagtcct ccggcccctg aatgcggcta atcccaactg   480
cggagcatac actctcaagc cagagggtag tgtgtcgtaa tgggcaactc tgcagcggaa   540
ccgactactt tgggtgtccg tgtttcattt tattcctata ctggctgctt atggtgacaa   600
ttgagagatt gttaccatat agctattgga ttggccatcc ggtgactaac agagctatta   660
tatatctttt tgttgggttt ataccactta gcttgaaaga ggttaaaact ctacattaca   720
ttttaatact gaacaccgca aaatggagga cgccaagaac atcaagaagg gcctgccccc   780
tttctaccct ctgaggacg gcaccgccgg cgagcagctg cacaaggcca tgaagaggta   840
cgccctggtg cctggcacca tcgccttcac cgacgcccac atcgaggtgg acatcaccta   900
cgccgagtac ttcgagatga gcgtgaggct ggccggcgaa atggaagagt acggcctgaa   960
caccaaccac aggatcgtgg tgtgcagcga aacagcctg cagttcttca tgcctgtgct  1020
gggcgccctg ttcatcggcg tggccgtggc ccctgccaac gacatctaca acgagaggga  1080
gctgctgaac agcatgggca tcagccagcc taccgtggtg ttcgtgagca agaagggcct  1140
gcagaagatc ctgaacgtgc agaagaagct gcctatcatc cagaagatca tcatcatgga  1200
cagcaagacc gactaccagg gcttccagag catgtacacc ttcgtgacca gccacctgcc  1260
tcctggcttc aacgagtacg acttcgtgcc tgagagcttc gacagggaca agaccatcgc  1320
cctgatcatg aacagcagcg gcagcaccgg cctgcctaag ggcgtggccc tgcctcacag  1380
gaccgcctgc gtgaggttca gccacgccag ggaccctgag ttcggcaacc agatcatccc  1440
tgacaccgcc atcctgagcg tggtgccttt ccaccacgtc ttcggcatgt tcaccaccct  1500
gggctacctg atctgcggct tcagggtggt gctgatgtac aggttcgagg aggagctgtt  1560
cctgaggagc ctgcaggact acaagatcca gagcgccctg ctggtgccta cccctgttcag  1620
cttcttcgcc aagagcaccc tgatcgacaa gtacgaccgc agcaacctgc acgagatccg  1680
cagcggcggc gcccctctga gcaagaggt gggcgaggcc gtggccaaga ggttccacct  1740
gcctggcatc aggcagggct acggcctgac cgagaccacc agcgcatcc tgatcacccc  1800
tgagggcgac gacaagcctg gcgccgtggg caaggtggtg cctttcttcg aggccaaggt  1860
ggtggacctg gacaccggca agaccctggg cgtgaaccag aggggcgagc tgtgcgtgag  1920
gggccctatg atcatgagcg gctacgtgaa caacccgac gccaccaacg ccctgatcga  1980
caaggacggc tggctgcaca gcggcgacat cgcctactgg gacgaggacg agcacttctt  2040
catcgtggac aggctgaaga gcctgatcaa gtacaagggc taccaggtgg ccctgccga  2100
gctggagagc atcctgctgc agcaccctaa catcttcgac gccggcgtgg ctggcttgcc  2160
tgatgacgat gctggagagc tgcctgccgc cgtggtggtg ctggagcacg gcaagaccat  2220
gaccgagaag gagatcgtgg actacgtggc cagccaggtg accaccgcca agaagctgag  2280
gggcggcgtg tgttcgtgg acgaggtgcc taagggcctg accggcaagc tggacgccag  2340
gaagatcagg gagatcctga tcaaggccaa gaagggcggc aagatccgcg tgtgatgata  2400
ataggctgga gcctcggtgg ccatgcttct tgccccttgg gcctcccccc agcccctcct  2460
cccccttcctg cacccgtacc ccccaaacac cattgtcaca ctccagtggt ctttgaataa  2520
agtctgagtg ggcggc                                                  2536

SEQ ID NO: 58          moltype = DNA    length = 2580
FEATURE                Location/Qualifiers
misc_feature           1..2580
                       note = sequence of circular RNA
source                 1..2580
                       mol_type = other DNA
                       organism = synthetic construct
SEQUENCE: 58
ttaaaacagc ctgtgggttg atcccaccca cagggcccac tgggcgctag cactctggta    60
tcacggtacc tttgtgcgcc tgttttatac ttcctccccc aactgcaact tagaagtaac   120
acaaaccgat caacagtcag cgtggcacac cagccacgtt ttgatcaaac acttctgtta   180
ccccggactg agtatcaata gactgctcac gcggttgaag gagaaaacgt tcgttatccg   240
gccaactact tcgagaaacc tagtaacgcc atggaagttg tggagtgttt cgctcagcac   300
tacccagtg tagatcaggt tgatgagtca ccgcattccc cacgggtgac cgtggcggtg   360
gctgcgttgg cggcctgccc atggggaaac ccatgggacg ctcttataca gacatggtgc   420
gaagagtcta ttgagctagt tggtagtcct ccggcccctg aatgcggcta atcccaactg   480
cggagcatac actctcaagc cagagggtag tgtgtcgtaa tgggcaactc tgcagcggaa   540
ccgactactt tgggtgtccg tgtttcattt tattcctata ctggctgctt atggtgacaa   600
ttgagagatt gttaccatat agctattgga ttggccatcc ggtgactaac agagctatta   660
tatatctttt tgttgggttt ataccactta gcttgaaaga ggttaaaact ctacattaca   720
ttttaatact gaacaccgca aaatggagga cgccaagaac atcaagaagg gcctgccccc   780
tttctaccct ctgaggacg gcaccgccgg cgagcagctg cacaaggcca tgaagaggta   840
cgccctggtg cctggcacca tcgccttcac cgacgcccac atcgaggtgg acatcaccta   900
cgccgagtac ttcgagatga gcgtgaggct ggccggcgaa atggaagagt acggcctgaa   960
caccaaccac aggatcgtgg tgtgcagcga aacagcctg cagttcttca tgcctgtgct  1020
gggcgccctg ttcatcggcg tggccgtggc ccctgccaac gacatctaca acgagaggga  1080
gctgctgaac agcatgggca tcagccagcc taccgtggtg ttcgtgagca agaagggcct  1140
gcagaagatc ctgaacgtgc agaagaagct gcctatcatc cagaagatca tcatcatgga  1200
cagcaagacc gactaccagg gcttccagag catgtacacc ttcgtgacca gccacctgcc  1260
```

-continued

```
tcctggcttc aacgagtacg acttcgtgcc tgagagcttc gacagggaca agaccatcgc  1320
cctgatcatg aacagcagcg gcagcaccgg cctgcctaag ggcgtggccc tgcctcacag  1380
gaccgcctgc gtgaggttca gccacgccag ggacccatct tcggcaacc  agatcatccc  1440
tgacaccgcc atcctgagcg tggtgccttt ccaccacggc ttcggcatgt tcaccaccct  1500
gggctacctg atctgcggct tcagggtggt gctgatgtac aggttcgagg aggagctgtt  1560
cctgaggagc ctgcaggact acaagatcca gagcgccctg ctggtgccta ccctgttcag  1620
cttcttcgcc aagagcaccc tgatcgacaa gtacgacctg agcaacctgc acgagatcgc  1680
cagcggcggc gcccctctga gcaaggaggt gggcgaggcc gtggccaaga ggttccacct  1740
gcctggcatc aggcagggct acggcctgac cgagaccacc agcgccatcc tgatcacccc  1800
tgagggcgac gacaagcctg gcgccgtggg caaggtggtg cctttcttcg aggccaaggt  1860
ggtggacctg gacaccggca agaccctggg cgtgaaccag aggggcgagc tgtgcgtgag  1920
gggccctatg atcatgagcg gctacgtgaa caacccgag gccaccaacg ccctgatcga  1980
caaggacggc tggctgcaca gcggcgacat cgcctactgg gacgaggacg agcacttctt  2040
catcgtggac aggctgaaga gcctgatcaa gtacaagggc taccaggtgg ccctgccga   2100
gctggagagc atcctgctgc agcacccctaa catcttcgac gccggcgtgg ctggcttgcc  2160
tgatgacgat gctggagagc tgcctgccgc cgtggtggtg ctggagcacg gcaagaccat  2220
gaccgagaag gagatcgtgg actacgtggc cagccaggtg accaccgcca agaagctgag  2280
gggccgcctg gtgttcgtgg acgaggtgcc taagggcctg accggcaagc tggacgccag  2340
gaagatcagg gagatcctga tcaaggccaa gaagggcggc aagatcgccg tgtgatgata  2400
atagcaaaca ccattgtcac actccagctg gagcctcggt ggccatgctt cttgcccctt  2460
gggcccaaac accattgtca cactccatcc ccccagcccc tcctcccctt cctgcacccg  2520
taccccccaa acaccattgt cacactccag tggtctttga ataaagtctg agtgggcggc  2580
```

SEQ ID NO: 59        moltype = DNA  length = 2754
FEATURE              Location/Qualifiers
misc_feature         1..2754
                     note = sequence of circular RNA
source               1..2754
                     mol_type = other DNA
                     organism = synthetic construct
SEQUENCE: 59

```
ttaaaacagc ctgtgggttg atcccaccca cagggcccac tgggcgctag cactctggta  60
tcacggtacc tttgtgcgcc tgttttatac ttcctccccc aactgcaact tagaagtaac  120
acaaaccgat caacagtcag cgtggcacac cagcacgtt ttgatcaaac acttctgtta  180
ccccggactg agtatcaata gactgctcac gcggttgaag gagaaaacgt tcgttatccg  240
gccaactact tcgagaaacc tagtaacgcc atggaagttg tggagtgttt cgctcagcac  300
tacccccagt tagatcaggt tgatgagtca ccgcattccc cacgggtgac cgtggcggtg  360
gctgcgttgg cggcctgccc atggggaaac ccatgggacg ctcttataca gacatggtgc  420
gaagagtcta ttgagctagt tggtagtcct ccggcccctg aatgcggcta atccaactg   480
cggagcatac actctcaagc cagagggtag tgtgtcgtaa tgggcaactc tgcagcggaa  540
ccgactactt tgggtgtccg tgtttcattt tattcctata ctggctgctt atggtgacaa  600
ttgagagatt gttaccatat agctattgga ttggccatcc ggtgactaac agagctatta  660
tatctttt tgttgggttt ataccactta gcttgaaaga ggtaaaact ctacattaca   720
ttttaatact gaacaccgca aaatggagga cgccaagaac atcaagaagg gccctgcccc  780
tttctacccct ctggaggacg gcaccgccgg cgagcagctg cacaaggcca tgaagaggta  840
cgccctggtg cctggcacca tcgccttcac cgacgcccac atcgaggtgg acatcaccta  900
cgccgagtac ttcgagatga gcgtgaggct ggccgaggtg atgaaggct acggcctgaa  960
caccaaccac aggatcgtgg tgtgcagcga aacagcctg cagttcttca tgcctgtgct  1020
gggcgccctg ttcatcggcg tggccgtggc ccctgccaac gacatctaca acgagaggga  1080
gctgctgaac agcatgggca tcagccagcc taccgtggtg ttcgtgagca agaagggcct  1140
gcagaagatc ctgaacgtgc agaagaagct gcctatcatc cagaagatca tcatcatgga  1200
cagcaagacc gactaccagg gcttccagag catgtacacc ttcgtgacca gccacctgcc  1260
tcctggcttc aacgagtacg acttcgtgcc tgagagcttc gacagggaca agaccatcgc  1320
cctgatcatg aacagcagcg gcagcaccgg cctgcctaag ggcgtggccc tgcctcacag  1380
gaccgcctgc gtgaggttca gccacgccag ggacccatct tcggcaacc  agatcatccc  1440
tgacaccgcc atcctgagcg tggtgccttt ccaccacggc ttcggcatgt tcaccaccct  1500
gggctacctg atctgcggct tcagggtggt gctgatgtac aggttcgagg aggagctgtt  1560
cctgaggagc ctgcaggact acaagatcca gagcgccctg ctggtgccta ccctgttcag  1620
cttcttcgcc aagagcaccc tgatcgacaa gtacgacctg agcaacctgc acgagatcgc  1680
cagcggcggc gcccctctga gcaaggaggt gggcgaggcc gtggccaaga ggttccacct  1740
gcctggcatc aggcagggct acggcctgac cgagaccacc agcgccatcc tgatcacccc  1800
tgagggcgac gacaagcctg gcgccgtggg caaggtggtg cctttcttcg aggccaaggt  1860
ggtggacctg gacaccggca agaccctggg cgtgaaccag aggggcgagc tgtgcgtgag  1920
gggccctatg atcatgagcg gctacgtgaa caacccgag gccaccaacg ccctgatcga  1980
caaggacggc tggctgcaca gcggcgacat cgcctactgg gacgaggacg agcacttctt  2040
catcgtggac aggctgaaga gcctgatcaa gtacaagggc taccaggtgg ccctgccga   2100
gctggagagc atcctgctgc agcacccctaa catcttcgac gccggcgtgg ctggcttgcc  2160
tgatgacgat gctggagagc tgcctgccgc cgtggtggtg ctggagcacg gcaagaccat  2220
gaccgagaag gagatcgtgg actacgtggc cagccaggtg accaccgcca agaagctgag  2280
gggccgcctg gtgttcgtgg acgaggtgcc taagggcctg accggcaagc tggacgccag  2340
gaagatcagg gagatcctga tcaaggccaa gaagggcggc aagatcgccg tgtgatgata  2400
atagatgcgc cgccgaccat gaatcatgca agtgcgtaag atagtcgcgg tcggcggcc   2460
gcatgctgga gcctcggtgg ccatgcttct tgccccttgg gccatgcggc cgccgaccag  2520
aatcatgcaa gtgcgtaaga tagtcgcggg tcggcggcc   2580
gcggccgcca accagaatca tgcaagtgcg taagatagtc gcgggtcggc ggccgcatct   2640
ccccttcctg cacccgtacc cccatgcggc cgccgaccag aatcatgcaa gtgcgtaaga  2700
tagtcgcggg tcggcggccg catgtggtct ttgaataaag tctgagtggg cggc         2754
```

SEQ ID NO: 60        moltype = AA  length = 4

```
FEATURE              Location/Qualifiers
REGION               1..4
                     note = sequence of amino acid unit
source               1..4
                     mol_type = protein
                     organism = synthetic construct
SEQUENCE: 60
MVSK                                                                         4

SEQ ID NO: 61        moltype = AA  length = 4
FEATURE              Location/Qualifiers
REGION               1..4
                     note = sequence of amino acid unit
source               1..4
                     mol_type = protein
                     organism = synthetic construct
SEQUENCE: 61
VSKG                                                                         4

SEQ ID NO: 62        moltype = AA  length = 4
FEATURE              Location/Qualifiers
REGION               1..4
                     note = sequence of amino acid unit
source               1..4
                     mol_type = protein
                     organism = synthetic construct
SEQUENCE: 62
SKGE                                                                         4

SEQ ID NO: 63        moltype = AA  length = 4
FEATURE              Location/Qualifiers
REGION               1..4
                     note = sequence of amino acid unit
source               1..4
                     mol_type = protein
                     organism = synthetic construct
SEQUENCE: 63
ELYK                                                                         4

SEQ ID NO: 64        moltype =   length =
SEQUENCE: 64
000

SEQ ID NO: 65        moltype = DNA  length = 12
FEATURE              Location/Qualifiers
misc_feature         1..12
                     note = codon sequence
source               1..12
                     mol_type = other DNA
                     organism = synthetic construct
SEQUENCE: 65
ttttcggtct ct                                                               12

SEQ ID NO: 66        moltype = DNA  length = 12
FEATURE              Location/Qualifiers
misc_feature         1..12
                     note = codon sequence
source               1..12
                     mol_type = other DNA
                     organism = synthetic construct
SEQUENCE: 66
attttggtcg ag                                                               12

SEQ ID NO: 67        moltype = DNA  length = 12
FEATURE              Location/Qualifiers
misc_feature         1..12
                     note = codon sequence
source               1..12
                     mol_type = other DNA
                     organism = synthetic construct
SEQUENCE: 67
actttggtca at                                                               12

SEQ ID NO: 68        moltype = DNA  length = 12
FEATURE              Location/Qualifiers
misc_feature         1..12
                     note = codon sequence
source               1..12
                     mol_type = other DNA
```

```
                                    -continued

SEQUENCE: 68
ggttcggtcc ag                                                           12

SEQ ID NO: 69          moltype = DNA   length = 12
FEATURE                Location/Qualifiers
misc_feature           1..12
                       note = codon sequence
source                 1..12
                       mol_type = other DNA
                       organism = synthetic construct SEQUENCE: 69
ttttcggtca gt                                                           12

SEQ ID NO: 70          moltype = DNA   length = 12
FEATURE                Location/Qualifiers
misc_feature           1..12
                       note = codon sequence
source                 1..12
                       mol_type = other DNA
                       organism = synthetic construct SEQUENCE: 70
actggggtcg tt                                                           12

SEQ ID NO: 71          moltype = DNA   length = 12
FEATURE                Location/Qualifiers
misc_feature           1..12
                       note = codon sequence
source                 1..12
                       mol_type = other DNA
                       organism = synthetic construct SEQUENCE: 71
tatggggtcc ag                                                           12

SEQ ID NO: 72          moltype =       length =
SEQUENCE: 72
000

SEQ ID NO: 73          moltype = DNA   length = 12
FEATURE                Location/Qualifiers
misc_feature           1..12
                       note = codon sequence
source                 1..12
                       mol_type = other DNA
                       organism = synthetic construct SEQUENCE: 73
attctgggtc at                                                           12

SEQ ID NO: 74          moltype = DNA   length = 12
FEATURE                Location/Qualifiers
misc_feature           1..12
                       note = codon sequence
source                 1..12
                       mol_type = other DNA
                       organism = synthetic construct SEQUENCE: 74
actctgggta tg                                                           12

SEQ ID NO: 75          moltype = DNA   length = 12
FEATURE                Location/Qualifiers
misc_feature           1..12
                       note = codon sequence
source                 1..12
                       mol_type = other DNA
                       organism = synthetic construct SEQUENCE: 75
acgctgggta tg                                                           12

SEQ ID NO: 76          moltype = DNA   length = 12
FEATURE                Location/Qualifiers
misc_feature           1..12
                       note = codon sequence
source                 1..12
                       mol_type = other DNA
                       organism = synthetic construct SEQUENCE: 76
atcctgggtc at                                                           12

SEQ ID NO: 77          moltype = DNA   length = 12
```

```
FEATURE              Location/Qualifiers
misc_feature         1..12
                     note = codon sequence
source               1..12
                     mol_type = other DNA
                     organism = synthetic construct
SEQUENCE: 77
accctgggta tg                                                     12

SEQ ID NO: 78        moltype = DNA  length = 12
FEATURE              Location/Qualifiers
misc_feature         1..12
                     note = codon sequence
source               1..12
                     mol_type = other DNA
                     organism = synthetic construct
SEQUENCE: 78
atactgggtc at                                                     12

SEQ ID NO: 79        moltype = DNA  length = 12
FEATURE              Location/Qualifiers
misc_feature         1..12
                     note = codon sequence
source               1..12
                     mol_type = other DNA
                     organism = synthetic construct
SEQUENCE: 79
acactgggta tg                                                     12

SEQ ID NO: 80        moltype = DNA  length = 13
FEATURE              Location/Qualifiers
misc_feature         1..13
                     note = sequence of ribozyme recognition site
source               1..13
                     mol_type = other DNA
                     organism = synthetic construct
SEQUENCE: 80
acgtcttaac caa                                                    13
```